(12) United States Patent
Basilion et al.

(10) Patent No.: US 12,144,863 B2
(45) Date of Patent: *Nov. 19, 2024

(54) PSMA TARGETED CONJUGATE COMPOUNDS AND USES THEREOF

(71) Applicant: CASE WESTERN RESERVE UNIVERSITY, Cleveland, OH (US)

(72) Inventors: James P. Basilion, Cleveland, OH (US); Xinning Wang, Cleveland, OH (US); Natalie Walker, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 98 days.

This patent is subject to a terminal disclaimer.

(21) Appl. No.: 17/555,958

(22) Filed: Dec. 20, 2021

(65) Prior Publication Data

US 2022/0378926 A1 Dec. 1, 2022

Related U.S. Application Data

(63) Continuation of application No. 17/029,731, filed on Sep. 23, 2020, now Pat. No. 11,202,836, which is a continuation-in-part of application No. PCT/US2019/023901, filed on Mar. 25, 2019.

(60) Provisional application No. 62/647,267, filed on Mar. 23, 2018.

(51) Int. Cl.
| | |
|---|---|
| A61K 47/00 | (2006.01) |
| A61K 31/704 | (2006.01) |
| A61K 38/05 | (2006.01) |
| A61K 47/64 | (2017.01) |
| A61P 35/00 | (2006.01) |

(52) U.S. Cl.
CPC ........ *A61K 47/6425* (2017.08); *A61K 31/704* (2013.01); *A61K 38/05* (2013.01); *A61P 35/00* (2018.01)

(58) Field of Classification Search
CPC .. A61K 47/6425; A61K 31/704; A61K 38/05; A61P 35/00
See application file for complete search history.

(56) References Cited

U.S. PATENT DOCUMENTS

| | | |
|---|---|---|
| 3,909,093 A | 9/1975 | Lundberg |
| 6,479,470 B1 | 11/2002 | Kozikowski et al. |
| 6,528,499 B1 | 3/2003 | Kozikowski et al. |
| 7,038,078 B2 | 5/2006 | Aldrich et al. |
| 7,381,745 B2 | 6/2008 | Kozikowski et al. |
| 7,408,079 B2 | 8/2008 | Pomper et al. |
| 8,078,264 B2 | 12/2011 | Basilion |
| 8,227,634 B2 | 7/2012 | Pomper et al. |
| 8,609,721 B2 | 12/2013 | Kozikowski et al. |
| 8,778,305 B2 | 7/2014 | Pomper et al. |
| 8,907,058 B2 | 12/2014 | Low et al. |
| 9,056,841 B2 | 6/2015 | Pomper et al. |
| 9,192,302 B2 | 11/2015 | Basilion |
| 9,193,763 B2 | 11/2015 | Low et al. |
| 9,226,981 B2 | 1/2016 | Pomper et al. |
| 9,271,653 B2 | 3/2016 | Basilion |
| 9,314,538 B2 | 4/2016 | Satpayev et al. |
| 9,371,360 B2 | 6/2016 | Pomper et al. |
| 9,694,091 B2 | 7/2017 | Pomper et al. |
| 9,776,977 B2 | 10/2017 | Pomper et al. |
| 9,861,713 B2 | 1/2018 | Pomper et al. |
| 9,884,132 B2 | 2/2018 | Pomper et al. |
| 9,889,199 B2 | 2/2018 | Basilion et al. |
| 9,925,273 B2 | 3/2018 | Pereira et al. |
| 9,951,324 B2 | 4/2018 | Low et al. |
| 10,011,657 B2 | 7/2018 | Gish et al. |
| 10,029,023 B2 | 7/2018 | Pomper et al. |
| 10,039,845 B2 | 8/2018 | Pomper et al. |
| 10,046,054 B2 | 8/2018 | Low et al. |
| RE47,103 E | 10/2018 | Morrison |
| 10,188,754 B2 | 1/2019 | Yang et al. |
| 10,207,005 B2 | 2/2019 | Basilion et al. |
| 10,232,058 B2 | 3/2019 | Pomper et al. |
| 10,363,313 B2 | 7/2019 | Basilion et al. |
| 10,369,113 B2 | 8/2019 | Chandran et al. |
| 10,406,240 B2 | 9/2019 | Low et al. |
| 10,426,850 B2 | 10/2019 | Yu et al. |
| 10,434,194 B2 | 10/2019 | Basilion et al. |
| 10,485,878 B2 | 11/2019 | Low et al. |
| 10,500,292 B2 | 12/2019 | Pomper et al. |
| 10,517,956 B2 | 12/2019 | Low et al. |
| 10,517,957 B2 | 12/2019 | Low et al. |
| 10,557,128 B2 | 2/2020 | Low et al. |
| 10,596,259 B2 | 3/2020 | Savariar et al. |
| 10,624,969 B2 | 4/2020 | Low et al. |

(Continued)

FOREIGN PATENT DOCUMENTS

| | | |
|---|---|---|
| WO | 2008/057437 A1 | 5/2008 |
| WO | 2010/0018230 A2 | 2/2010 |

(Continued)

OTHER PUBLICATIONS

U.S. Appl. No. 16/573,570, filed Sep. 17, 2019, U.S. Non-Final Rejection dated Jun. 10, 2022, 24 pgs.
U.S. Appl. No. 16/901,874, filed Jun. 15, 2020, U.S. Non-Final Rejection dated Aug. 18, 2022, 13 pgs.
Agnes et al., An Optical Probe for Noninvasive Molecular Imaging of Orthotopic Brain Tumors Overexpressing Epidermal Growth Factor Receptor, Mol Cancer Ther, vol. 11(10): OF1-0F10, (published on line Jul. 17, 2012).
Bennike {Development of a Novel Peptide Based Probe for Tumour Imaging, Aalborg University, Thesis {Jun. 2011 ), 92 pages.
Cheng et al. Highly Efficient Drug Delivery with Gold Nanoparticle Vectors for in Vivo Photodynamic Therapy of Cancer. J. Am. Chem. Soc. 2008, 130, 10643-10647.
Choi et al. Mechanism of active targeting in solid tumors with transferrin-containing gold nanoparticles. Proc Natl Acad Sci USA. Jan. 19, 2010;107(3):1235-1240.

(Continued)

*Primary Examiner* — Jeanette M Lieb
(74) *Attorney, Agent, or Firm* — Tarolli, Sundheim, Covell & Tummino LLP

(57) ABSTRACT

PSMA targeted conjugate compounds, pharmaceutical compositions comprising these compounds, methods for treating and detecting cancers in a subject, methods for identifying cancer cells in a sample are described herein.

25 Claims, 18 Drawing Sheets

(56) References Cited

U.S. PATENT DOCUMENTS

| | | | |
|---|---|---|---|
| 10,624,970 B2 | 4/2020 | Low et al. |
| 10,624,971 B2 | 4/2020 | Low et al. |
| 10,646,581 B2 | 5/2020 | Low et al. |
| 10,653,806 B2 | 5/2020 | Pomper et al. |
| 10,660,971 B2 | 5/2020 | Li |
| 10,683,272 B2 | 6/2020 | Ray et al. |
| 10,688,198 B2 | 6/2020 | Ray et al. |
| 10,709,794 B2 | 7/2020 | Basilion et al. |
| 10,717,750 B2 | 7/2020 | Pomper et al. |
| 10,722,593 B2 | 7/2020 | Vining et al. |
| 10,736,974 B2 | 8/2020 | Pomper et al. |
| 10,744,206 B2 | 8/2020 | Li |
| 2006/0222595 A1 | 10/2006 | Mukherjee et al. |
| 2007/0160617 A1 | 7/2007 | Ma et al. |
| 2008/0193381 A1 | 8/2008 | Babich et al. |
| 2008/0213377 A1 | 9/2008 | Bhatia et al. |
| 2009/0011004 A1 | 1/2009 | Lutz et al. |
| 2009/0061010 A1 | 3/2009 | Zale et al. |
| 2009/0297615 A1 | 12/2009 | Wang et al. |
| 2009/0304803 A1 | 12/2009 | Hasan |
| 2010/0026068 A1 | 2/2010 | Yoo et al. |
| 2010/0183504 A1 | 7/2010 | Chen |
| 2010/0324008 A1 | 12/2010 | Low et al. |
| 2010/0329983 A1 | 12/2010 | Stewart |
| 2011/0165079 A1 | 7/2011 | Lu et al. |
| 2011/0262347 A1 | 10/2011 | Ruoslahti et al. |
| 2011/0268660 A1 | 11/2011 | Danikas et al. |
| 2012/0282632 A1 | 11/2012 | Chiu et al. |
| 2012/0323164 A1 | 12/2012 | Kenney et al. |
| 2013/0289520 A1 | 10/2013 | Febvay et al. |
| 2013/0315834 A1 | 11/2013 | Praveen et al. |
| 2014/0220143 A1 | 8/2014 | Dhar et al. |
| 2014/0286969 A1 | 9/2014 | Tschoepe et al. |
| 2015/0056132 A1 | 2/2015 | Dennis et al. |
| 2015/0366968 A1 | 12/2015 | Basilion |
| 2016/0067341 A1 | 3/2016 | Low et al. |
| 2018/0106809 A1 | 4/2018 | Dennis et al. |
| 2019/0010237 A1 | 1/2019 | Reilly et al. |
| 2019/0099431 A1 | 4/2019 | Gish et al. |
| 2019/0111150 A1 | 4/2019 | Singh et al. |
| 2019/0262417 A1 | 8/2019 | Leanna et al. |
| 2019/0328898 A1 | 10/2019 | Torgov et al. |
| 2019/0328911 A1 | 10/2019 | Krol et al. |
| 2020/0199245 A1 | 6/2020 | Liu et al. |
| 2020/0215200 A1 | 7/2020 | Allan et al. |
| 2020/0276331 A1 | 9/2020 | Coumans |
| 2020/0282072 A1 | 9/2020 | Tschoepe et al. |

FOREIGN PATENT DOCUMENTS

| | | |
|---|---|---|
| WO | 2011/106639 A1 | 9/2011 |
| WO | 2012/016713 A2 | 2/2012 |
| WO | 2014127365 A1 | 8/2014 |

OTHER PUBLICATIONS

Craig et al., Langmuir, vol. 24:10282-10292 (2008) {Year: 2008}.

DeJesus, Synthesis of [64Cu]Cu-NOTA-Bn-GE11 for PET Imaging of EGFR-Rich Tumors, Current Radiopharmaceuticals, vol. 5(1):15-18 {Jan. 2012}.

Ikeda, Masato, et al., "Supramolecular hydrogel capsule showing prostate specific antigen-responsive function for :; ensing and targeting prostate cancer cells", Chem. Sci., 2010, 1, 491-498.

Ikuta et al. The effect of molecular structure on the anticancer drug release rate from prodrug nanoparticles. 2015,51, 12835-12838.

Kularatne, Sumith A., et al., "Synthesis and Biological Analysis of Prostate-Specific Membrane Antigen-Targeted Anticancer Prodrugs", Journal of Medicinal Chemistry, vol. 53, No. 21, Nov. 11, 2010, pp. 7767-7777, KP055103918.

Li et al. Identification and characterization of a novel peptide ligand of epidermal growth factor receptor for targeted delivery of therapeutics. The FASEB J. 2005 19(14):1978-1984.

Liu et al. {Spacer length effects on in vitro imaging and surface accessibility of fluorescent inhibitors of prostate specific membrane antigen, Bioorganic & Medicinal Letters, vol. 21 :7013-7016.

Otsuka et al. PEGylated nanoparticles for biological and pharmaceutical applications. vol. 55, Issue 3, Feb. 24, 2003, pp. 403-419.

Samia et al. Semiconductor Quantum Dots for Photodynamic Therapy. J. Am. Chem. Soc. 2003, 125:15736.

Song et al. (Peptide Ligand-mediated liposome distribution and targeting to EGFR expressing tumor in vivo, International Journal of Pharmaceutics, vol. 363:155-161 (pub online Jul. 23, 2008).

Steichen et al. A review of current nanoparticle and targeting moieties for the delivery of cancer therapeutics. Feb. 14, 2013; 48(3): 416-427.

Vagner et al., Bioorganic & Medicinal Chemistry Letter, vol. 14:211-215 (2004).

Applicant: Case Western Reserve University; "PSMA Targeted Conjugate Compounds and Uses Thereof"; PCT International Application No. PCT/US2019/023901; Filed: Mar. 25, 2019; PCT International Search Report; Authorized Officer: shane thomas; Date of Completion: May 3, 2019; 8 pgs.

MC-Val-Cit-PABC

PSMA TARGETED CONJUGATE COMPOUNDS AND USES THEREOF

RELATED APPLICATION

This application is a Continuation-in-Part of PCT/US2019/023901, filed Mar. 25, 2019, which claims priority from U.S. Provisional Application No. 62/647,267, filed Mar. 23, 2018, the subject matter of which is incorporated herein by reference in its entirety.

TECHNICAL FIELD

This application relates to prostate-specific membrane antigen (PSMA) targeted conjugate compounds and to their use in compositions for targeting, imaging, and treating cancer.

BACKGROUND

Prostate-specific membrane antigen (PSMA) is a 120 kDa protein expressed in prostate tissues and was originally identified by reactivity with a monoclonal antibody designated 7E11-C5 (Horoszewicz et al., 1987, Anticancer Res. 7:927-935; U.S. Pat. No. 5,162,504). PSMA is characterized as a type II transmembrane protein sharing sequence identity with the transferrin receptor (Israeli et al., 1994, Cancer Res. 54:1807-1811). PSMA is a glutamate carboxy-peptidase that cleaves terminal carboxy glutamates from both the neuronal dipeptide N-acetylaspartylglutamate (NAAG) and gamma-linked folate polyglutamate. That is, expression of PSMA cDNA confers the activity of N-acetylated a-linked acidic dipeptidase or "NAALADase" activity (Carter et al., 1996, PNAS 93:749-753).

PSMA is expressed in increased amounts in prostate cancer, and elevated levels of PSMA are detectable in the sera of these patients (Horoszewicz et al., 1987, supra; Rochon et al., 1994, Prostate 25:219-223; Murphy et al., 1995, Prostate 26:164-168; and Murphy et al., 1995, Anticancer Res. 15:1473-1479). As a prostate carcinoma marker, PSMA is believed to serve as a target for imaging and cytotoxic treatment modalities for prostate cancer. Prostate carcinogenesis, for example, is associated with an elevation in PSMA abundance and enzymatic activity of PSMA. PSMA antibodies, particularly indium-111 labeled and tritium labeled PSMA antibodies, have been described and examined clinically for the diagnosis and treatment of prostate cancer. PSMA is expressed in prostatic ductal epithelium and is present in seminal plasma, prostatic fluid and urine.

Recent evidence suggests that PSMA is also expressed in tumor associated neovasculature of a wide spectrum of malignant neoplasms including conventional (clear cell) renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma. (Chang et al. (1999) Cancer Res. 59, 3192-3198).

SUMMARY

Embodiments described herein relate to PSMA targeted conjugate compounds, pharmaceutical compositions comprising these compounds, methods for treating and detecting cancers (e.g., prostate cancer) in a subject using these PSMA targeted conjugate compounds, and methods for identifying cancer cells (e.g., prostate cancer cells) in a sample using these compounds.

In some embodiments, the compound can include the general formula (I):

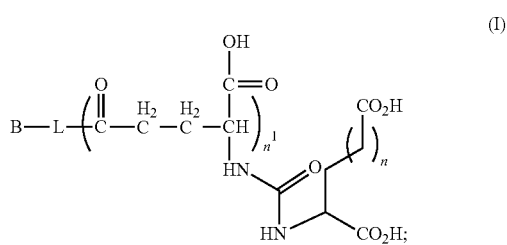

wherein n and $n^1$ are each independently 1, 2, 3, or 4;

L is an optionally substituted aliphatic or heteroaliphatic linking group;

B has the following formula:

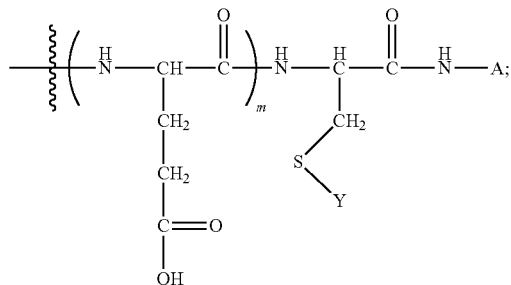

m is 1, 2, 3, or 4;

A is H or

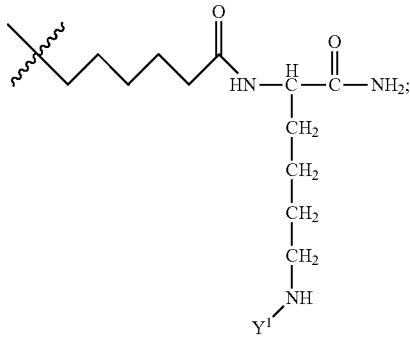

and

Y and $Y^1$ are each independently selected from at least one of a detectable moiety, therapeutic agent, or a theranostic agent that is directly or indirectly linked to, respectively, the thiol group of B and the amine group of A.

Other embodiments relate to a composition for diagnosing and/or treating cancer, the composition comprising a prostate specific membrane antigen (PSMA) targeted conjugate compound that includes general formula (I):

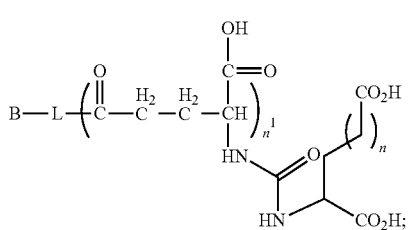

(I)

wherein n and $n^1$ are each independently 1, 2, 3, or 4;

L is an optionally substituted aliphatic or heteroaliphatic linking group;

B has the following formula:

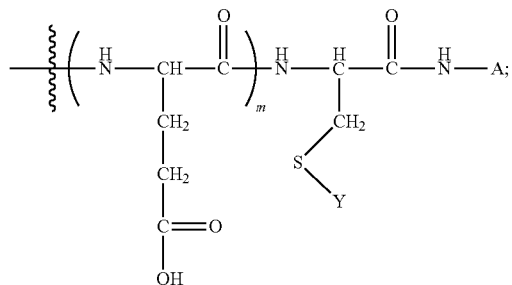

m is 1, 2, 3, or 4;

A is H or

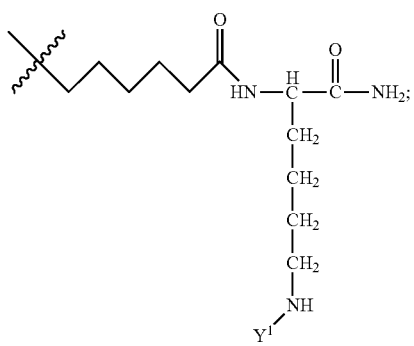

and

Y and $Y^1$ are each independently selected from at least one of a detectable moiety, therapeutic agent, or a theranostic agent that is directly or indirectly linked to, respectively, the thiol group of B and the amine group of A.

Another embodiment relates to a composition for treating prostate cancer in a subject, the composition comprising a PSMA targeted conjugate compound having the general formula:

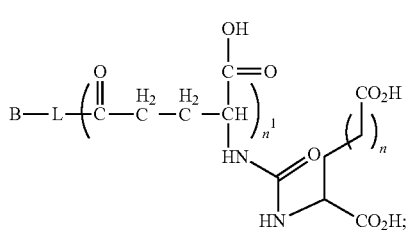

(I)

wherein n and $n^1$ are each independently 1, 2, 3, or 4;

L is an optionally substituted aliphatic or heteroaliphatic linking group;

B has the following formula:

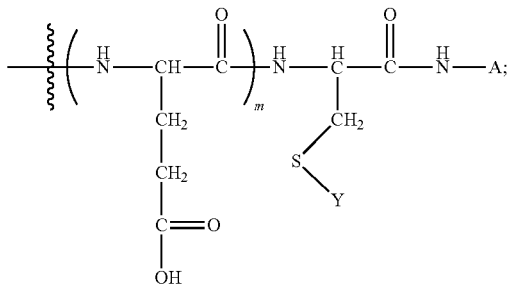

m is 1, 2, 3, or 4;

A is H or

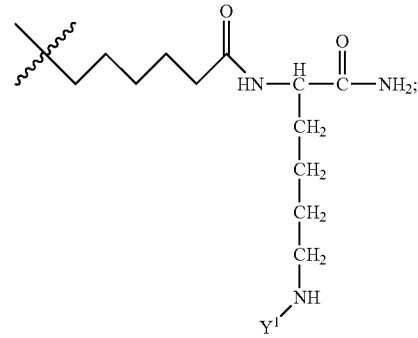

and

Y and $Y^1$ are each independently selected from at least one of a detectable moiety, therapeutic agent, or a theranostic agent that is directly or indirectly linked to, respectively, the thiol group of B and the amine group of A.

Still other embodiments relate to a method of treating cancer, such as prostate cancer, in a subject. The method includes administering to the subject a therapeutically effective amount of a composition that includes a prostate specific membrane antigen (PSMA) targeted conjugate compound having the general formula (I):

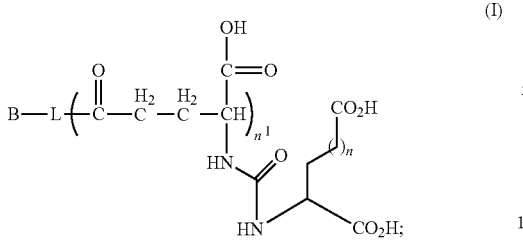

wherein n and $n^1$ are each independently 1, 2, 3, or 4;
L is an optionally substituted aliphatic or heteroaliphatic linking group;
B has the following formula:

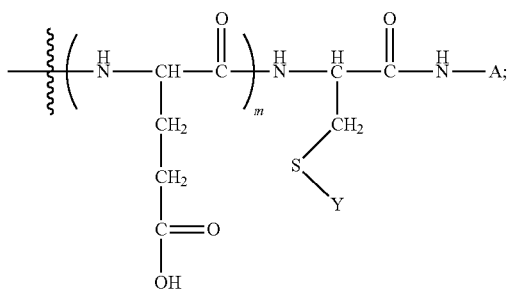

m is 1, 2, 3, or 4;
A is H or

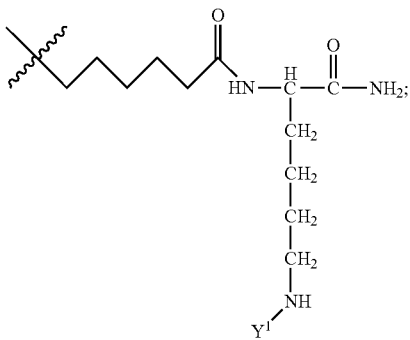

and
Y and $Y^1$ are each independently selected from at least one of a detectable moiety, therapeutic agent, or a theranostic agent that is directly or indirectly linked to, respectively, the thiol group of B and the amine group of A. The therapeutic agent can be an anti-cancer agent, such as doxorubicin or monomethylauristatin E (MMAE).

BRIEF DESCRIPTION OF THE DRAWINGS

The following is a brief description of the drawings which are presented for the purpose of illustrating the invention and not for the purpose of limiting them.

DETAILED DESCRIPTION

Figure 1:
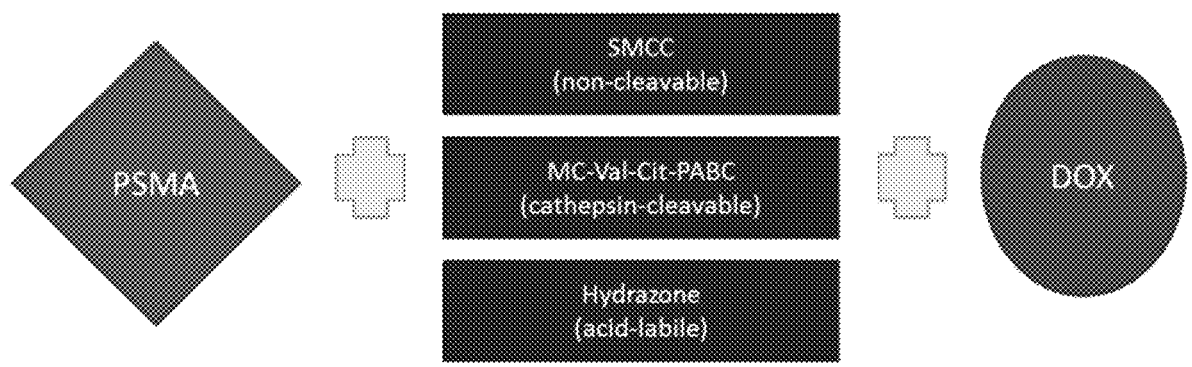
FIG. 1 illustrates a schematic showing an outline of structures of three PSMA-1-Doxorubicin Prodrug Conjugates.

All scientific and technical terms used in this application have meanings commonly used in the art unless otherwise specified. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

As used herein, the term "sample" can refer to a specimen or culture obtained from any source, as well as clinical, research, biological and environmental samples. Biological samples may be obtained from animals (including humans) and encompass cells, fluids, solids, tissues, and organs, and whole organisms.

As used herein, the term "subject" can refer to any animal including, but not limited to, humans and non-human animals (e.g., rodents, arthropods, insects, fish (e.g., zebrafish)), non-human primates, ovines, bovines, ruminants, lagomorphs, porcines, caprines, equines, or canines felines, aves, etc.).

As used herein, the terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

As used herein, the terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term can also include peptides and polypeptide fragments, motifs and the like, glycosylated polypeptides, and all "mimetic" and "peptidomimetic" polypeptide forms.

"PSMA" refers to Prostate Specific Membrane Antigen, a potential carcinoma marker that has been hypothesized to serve as a target for imaging and cytotoxic treatment modalities for cancer.

As used herein, the term "small molecule" can refer to lipids, carbohydrates, polynucleotides, polypeptides, or any other organic or inorganic molecules.

As used herein, the term "imaging probe" can refer to a biological or chemical moiety that may be used to detect, image, and/or monitor the presence and/or progression of a cell cycle, cell function/physiology, condition, pathological disorder and/or disease.

As used herein, the terms "treating" or "treatment" of a disease can refer to executing a treatment protocol to eradicate at least one diseased cell. Thus, "treating" or "treatment" does not require complete eradication of diseased cells.

As used herein, the term "nanoparticle" refers to any particle having a diameter of less than 1000 nanometers (nm). In some embodiments, nanoparticles can be optically or magnetically detectable. In some embodiments, intrinsically fluorescent or luminescent nanoparticles, nanoparticles that comprise fluorescent or luminescent moieties, plasmon resonant nanoparticles, and magnetic nanoparticles are among the detectable nanoparticles that are used in various embodiments. In general, the nanoparticles should have dimensions small enough to allow their uptake by eukaryotic cells. Typically, the nanoparticles have a longest straight dimension (e.g., diameter) of 200 nm or less. In some embodiments, the nanoparticles have a diameter of 100 nm or less. Smaller nanoparticles, e.g., having diameters of 50 nm or less, e.g., about 1 nm to about 30 nm or about 1 nm to about 5 nm, are used in some embodiments.

As used herein, an "effective amount" can refer to that amount of a therapeutic agent that results in amelioration of symptoms or a prolongation of survival in the subject and relieves, to some extent, one or more symptoms of the disease or returns to normal (either partially or completely) one or more physiological or biochemical parameters associated with or causative of the disease.

As used herein, therapeutic agents can include any agent (e.g., molecule, drug, pharmaceutical composition, etc.) capable of preventing, inhibiting, or arresting the symptoms and/or progression of a disease.

Embodiments described herein relate to PSMA targeted conjugate compounds, as well as pharmaceutical compositions comprising these conjugate compounds, methods for treating and detecting cancers, such as prostate cancer, in a subject using these compounds, and methods for identifying cancer cells in a sample using these compounds.

Using a modified PSMA-1 peptide ligand, PSMA ligands (PSMA-1(Cys)) have been developed that include a terminal cysteine residue that allows for coupling of the thiol group to maleimide linkers and/or the cysteine residue amine group to a carbon linker to create PSMA targeted compounds conjugated to one or more detectable moiety, therapeutic agent, or a theranostic agent. It has been shown that PSMA targeted compounds conjugated to anti-cancer agents can increase uptake of the conjugate compound in PSMA expressing cells while also improving cell killing compared to agents administered alone. In addition, PSMA targeted conjugate compounds described herein can decrease off-target toxicity of the therapeutic agent, or a theranostic agent administered (e.g., systemically) to a subject.

Pathological studies indicate that PSMA is expressed by virtually all prostate cancers, and its expression is further increased in poorly differentiated, metastatic, and hormone-refractory carcinomas. Higher PSMA expression is also found in cancer cells from castration-resistant prostate cancer patients. Increased PSMA expression is reported to correlate with the risk of early prostate cancer recurrence after radical prostatectomy. In addition to being overexpressed in prostate cancer (PCa), PSMA is also expressed in the neovasculature of neoplasms including but not limited to conventional (clear cell) renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma.

In some embodiments, the PSMA targeted conjugate compounds described herein, can selectively recognize PSMA-expressing tumors, cancer cells, and/or cancer neovasculature in vivo and be used to deliver a therapeutic agent, detectable moiety, and/or theranostic agent to the PSMA-expressing tumors, cancer cells, and/or cancer neovasculature to treat and/or detect the PSMA-expressing tumors, cancer cells, and/or cancer neovasculature in a subject.

In some embodiments, the PSMA expressing cancer that is treated and/or detected is prostate cancer. In other embodiments, the cancer that is treated and/or detected can include malignant neoplasms, such a conventional (clear cell) renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma.

In some embodiments, the compound can include a PSMA targeted conjugate compound that has the general formula (I):

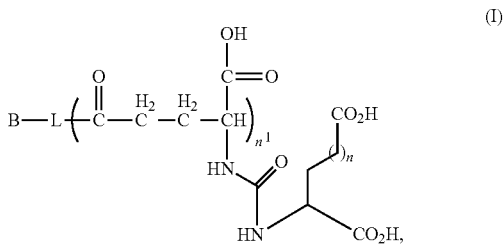

wherein:

n and $n^1$ are each independently 1, 2, 3, or 4;

L is an optionally substituted aliphatic or heteroaliphatic linking group;

B has the following formula:

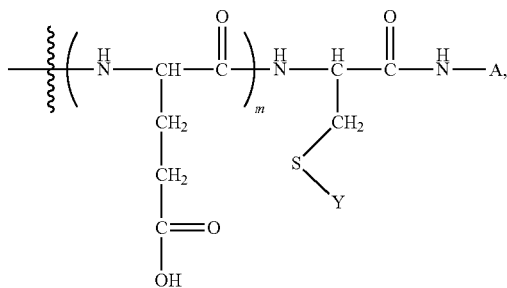

m is 1, 2, 3, or 4;

A is H or

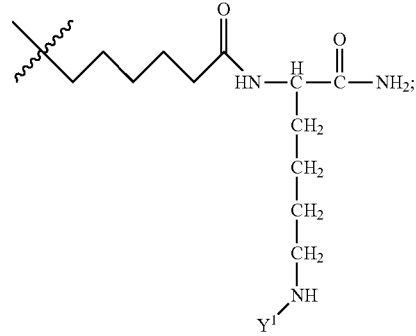

and

Y and $Y^1$ are each independently selected from at least one of a detectable moiety, therapeutic agent, or a theranostic agent that is directly or indirectly linked to, respectively, the thiol group of B and the amine group of A.

In other embodiments, Y and $Y^1$ can each independently be selected from the group consisting of an imaging agent, anticancer agent, and combinations thereof that is directly or indirectly linked to, respectively, the thiol group of B and the amine group of A.

In other embodiments, L can be an optionally substituted aliphatic or heteroaliphatic group that includes at least one ring selected from the group consisting of an optionally substituted 4 to 7 membered nonaromatic heterocyclic ring and an optionally substituted C4-C7 cycloalkyl ring.

An aliphatic group is a straight chained, branched or cyclic non-aromatic hydrocarbon, which is completely saturated or which contains one or more units of unsaturation. An alkyl group is a saturated aliphatic group. Typically, a straight chained or branched aliphatic group has from 1 to about 10 carbon atoms, preferably from 1 to about 4, and a cyclic aliphatic group has from 3 to about 10 carbon atoms, preferably from 3 to about 8. An aliphatic group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms. C1-C4 straight chained or branched alkyl or alkoxy groups or a C3-C8 cyclic alkyl or alkoxy group (preferably C1-C4 straight chained or branched alkyl or alkoxy group) are also referred to as a "lower alkyl" or "lower alkoxy" groups; such groups substituted with —F, —Cl, —Br, or —I are "lower haloalkyl" or "lower haloalkoxy" groups; a "lower hydroxyalkyl" is a lower alkyl substituted with —OH; and the like.

Optional substituents for a substitutable atom in alkyl, cycloalkyl, aliphatic, cycloaliphatic, heterocyclic, benzylic, aryl, or heteroaryl groups described herein are those substituents that do not substantially interfere with the activity of the disclosed compounds. A "substitutable atom" is an atom that has one or more valences or charges available to form one or more corresponding covalent or ionic bonds with a substituent. For example, a carbon atom with one valence available (e.g., —C(—H)═) can form a single bond to an alkyl group (e.g., —C(-alkyl)═), a carbon atom with two valences available (e.g., —C(H$_2$)—) can form one or two single bonds to one or two substituents (e.g., —C(alkyl)(Br))—, —C(alkyl)(H)—) or a double bond to one substituent (e.g., —C═O)—), and the like. Substitutions contemplated herein include only those substitutions that form stable compounds.

For example, suitable optional substituents for substitutable carbon atoms include —F, —Cl, —Br, —I, —CN, —NO$_2$, —OR$^a$, —C(O)R$^a$, —OC(O)R$^a$, —C(O)OR$^a$, —SR$^a$, —C(S)R$^a$, —OC(S)R$^a$, —C(S)OR$^a$, —C(O)SR$^a$, —C(S)SR$^a$, —S(O)R$^a$, —SO$_2$R$^a$, —SO$_3$R$^a$, —POR$^a$R$^b$, PO$_2$R$^a$R$^b$, —PO$_3$R$^a$R$^b$, —PO$_4$R$^a$R$^b$, —P(S)R$^a$R$^b$, —P(S)OR$^a$R$^b$, —P(S)O$_2$R$^a$R$^b$, —P(S)O$_3$R$^a$R$^b$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), —C(NR$^c$)—N(R$^a$R$^b$), —NR$^d$—C(NR$^c$)—N(R$^a$R$^b$), —NR$^a$N(R$^a$R$^b$), —CRC═CR$^a$R$^b$, —C═CR$^a$, ═O, ═S, ═CR$^a$R$^b$, ═NR$^a$, ═NOR$^a$, ═NNR$^a$, optionally substituted alkyl, optionally substituted cycloalkyl, optionally substituted aliphatic, optionally substituted cycloaliphatic, optionally substituted heterocyclic, optionally substituted benzyl, optionally substituted aryl, and optionally substituted heteroaryl, wherein R$^a$—R$^d$ are each independently —H or an optionally substituted aliphatic, optionally substituted cycloaliphatic, optionally substituted heterocyclic, optionally substituted benzyl, optionally substituted aryl, or optionally substituted heteroaryl, or, —N(R$^a$R$^b$), taken together, is an optionally substituted heterocyclic group. Also contemplated are isomers of these groups.

Suitable substituents for nitrogen atoms having two covalent bonds to other atoms include, for example, optionally substituted alkyl, optionally substituted cycloalkyl, optionally substituted aliphatic, optionally substituted cycloaliphatic, optionally substituted heterocyclic, optionally substituted benzyl, optionally substituted aryl, optionally substituted heteroaryl, —CN, —NO$_2$, —OR$^a$, —C(O)R$^a$, —OC(O)R$^a$, —C(O)OR$^a$, —SR$^a$, —S(O)R$^a$, —SO$_2$R$^a$, —SO$_3$R$^a$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), and the like.

Suitable substituents for nitrogen atoms having three covalent bonds to other atoms include —OH, alkyl, and alkoxy (preferably C1-C4 alkyl and alkoxy). Substituted ring nitrogen atoms that have three covalent bonds to other ring atoms are positively charged, which is balanced by counteranions such as chloride, bromide, fluoride, iodide, formate, acetate and the like. Examples of other suitable counter anions are provided in the section below directed to suitable pharmacologically acceptable salts.

In some embodiments, B can have the following formula:

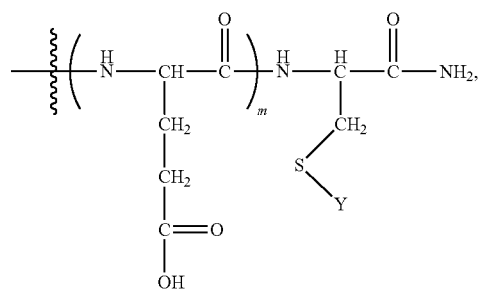

wherein m is 1, 2, 3, or 4; and

Y can include at least one of a detectable moiety, therapeutic agent, or theranostic agent that is directly or indirectly linked to the thiol group of B.

In some embodiments, B can have the following formula:

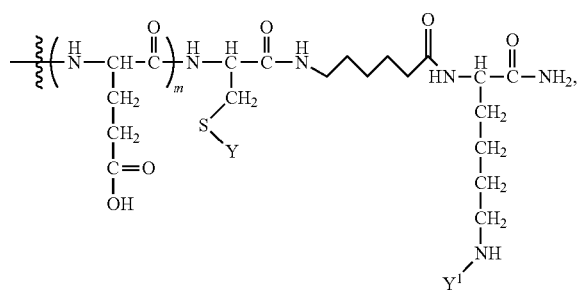

wherein m is 1, 2, 3, or 4; and

Y and Y$^1$ are each independently selected from at least one of a detectable moiety, therapeutic agent, or a theranostic agent that is directly or indirectly linked to, respectively, the thiol group and the amine group.

In other embodiments, the compound can have the general formula:

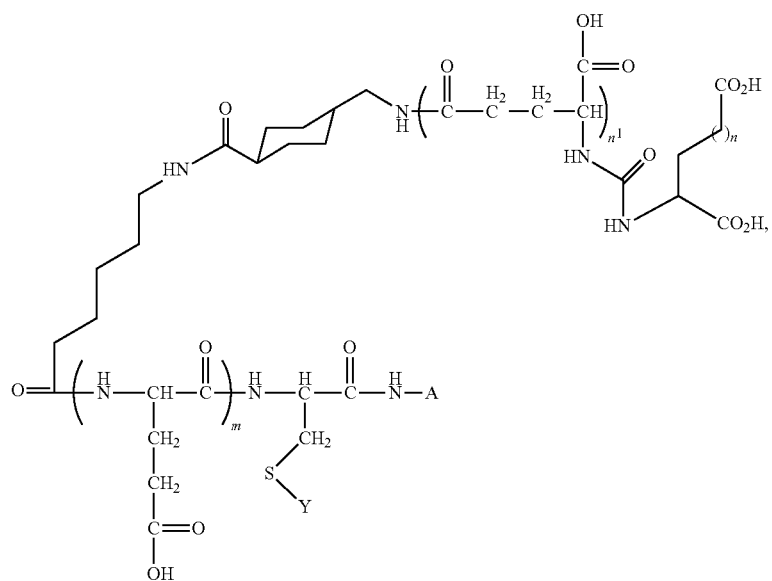

wherein m, n and $n^1$ are each independently 1, 2, 3, or 4;
A is H or

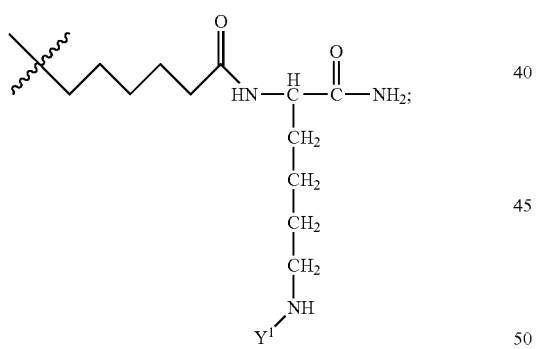

and

Y and $Y^1$ are each independently selected from at least one of a detectable moiety, therapeutic agent, or a theranostic agent that is directly or indirectly linked to, respectively, the thiol group of B and the amine group of A.

In certain embodiments, the PSMA targeted conjugated compound can have the general formula:

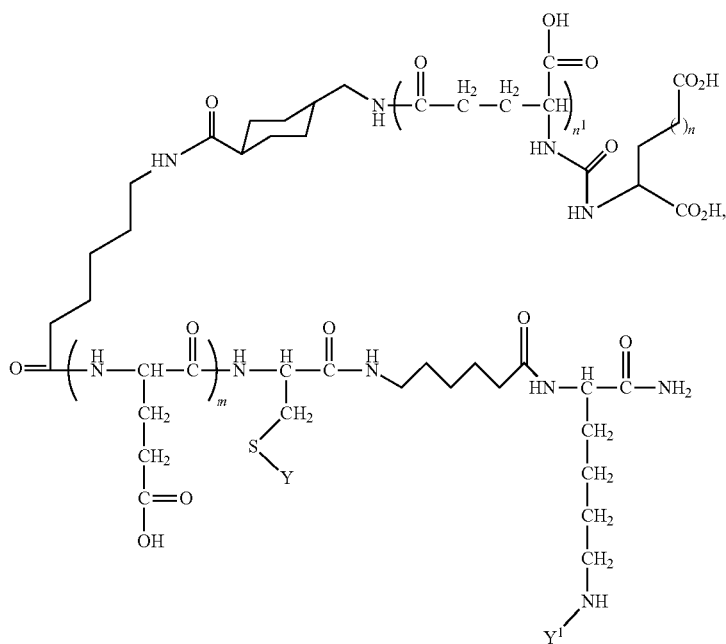

wherein m, n, and $n^1$ are independently 1, 2, 3, or 4; and Y and $Y^1$ are each independently selected from at least one of a detectable moiety, therapeutic agent, or a theranostic agent that is directly or indirectly linked to, respectively, the thiol group and the amine group.

In some embodiments, a therapeutic, imaging and/or a theranostic agent can be coupled directly or indirectly to the PSMA targeted compound via a linker. The linker can include a heterobifunctional linker capable of conjugating to the cysteine residue of the PSMA targeted compound via a maleimide group that is sulfhydryl (thiol; —SH) reactive.

In some embodiments, the heterobifunctional linker can include a protease cleavable or acid-labile linker. In particular embodiments, the detectable moiety, the therapeutic agent, or the theranostic agent can be coupled directly or indirectly to the PSMA targeted compound via an acid-labile linker, such as a 4-(4-maleimidomethyl)cyclohexane-1-carboxyl hydrazide (MMCCH) linker. The MMCCH linker includes a hydrazine bond that can be cleaved to release the detectable moiety, therapeutic agent, or the theranostic agent coupled to the PSMA targeted compound. In alternative embodiments, the detectable moiety, the therapeutic agent, or the theranostic agent can be coupled directly or indirectly to the PSMA targeted portion of the compound (PSMA-1 (Cys)) via a non-cleavable linker, such as Succinimidyl 4-(N-maleimidomethyl)cyclohexane-1-carboxylate (SMCC).

In other embodiments, the detectable moiety, therapeutic agent, or the theranostic agent can be coupled directly or indirectly to the PSMA targeted portion of the compound (PSMA-1(Cys)) via a protease cleavable linker. The protease cleavable linker can include a MC-Val-Cit-PABC protease cleavable linker where the Valine-Citrulline-PABC portion is protease cleaveable.

In some embodiments, the PSMA targeted conjugate compounds described herein are prepared by coupling a "vc-MMAE" linker-drug combination construct to the thiol group of the cysteine residue of the PSMA targeted compound. The vc-MMAE construct is also referred to as the linker-drug mc-vc-PABC-MMAE. The construct utilizes a maleimidocaproyl (mc) spacer, a protease-sensitive dipeptide, valine-citrulline (vc), a self-immolative spacer, para-amino benzyloxycarbonyl (PABC), and the antimitotic agent, monomethyl auristatin E (MMAE). The mc spacer provides enough room for the vc group to be recognized by the lysosomal cysteine protease cathepsin B in a PSMA expressing cell, which cleaves the citrulline-PABC amide bond. The resultant PABC-substituted MMAE is not a stable intermediate and spontaneously undergoes a 1,6-elimination with a loss of p-iminoquinone methide and carbon dioxide (self-immolation) leaving MMAE as the product to exert anti-mitotic effects.

In some embodiments, the PSMA targeted conjugate compound can include a detectable moiety directly or indirectly coupled to B. Examples of detectable moieties include, but are not limited to: various ligands, imaging agents, contrast agents, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, chelating groups, and biotin, digoxigenin or other haptens and proteins for which antisera or monoclonal antibodies are available.

In some embodiments, radionuclides can include atomic isotopes such as $^{99m}Tc$, $^{111}In$, $^{123}I$, $^{124}I$, $^{131}I$, $^{67}Ga$, $^{201}Tl$, $^{125}I$, $^{18}F$, $^{11}C$, $^{76}Br$, $^{124}I$, $^{68}Ga$, $^{82}Rb$, $^{13}N$, $^{64}Cu$, $^{90}Y$, $^{188}R$, T(tritium), $^{32}P$, $^{35}S$, $^{153}Sm$, $^{89}Sr$, $^{211}At$, and $^{89}Zr$. These isotopes can be directly or indirectly coupled to the PSMA ligand.

Fluorescence labeling agents or infrared labeling agents include those known to the art, many of which are commonly commercially available, such as ALEXA 350, PACIFIC BLUE, MARINA BLUE, ACRIDINE, EDANS, COUMARIN, BODIPY 493/503, CY2, BODIPY FL-X, DANSYL, ALEXA 488, FAM, OREGON GREEN, RHODAMINE GREEN-X, TET, ALEXA 430, CAL GOLD, BODIPY R6G-X, JOE, ALEXA 532, VIC, HEX, CAL ORANGE™, ALEXA 555, BODIPY 564/570, BODIPY TMR-X, QUASAR. 570, ALEXA 546, TAMRA, RHODAMINE RED-X, BODIPY 581/591, CY3.5, CY5.5, ROX, ALEXA 568, CAL RED, BODIPY TR-X, ALEXA 594, BODIPY 630/650-X, PULSAR 650, BODIPY 630/665-X, ALEXA 647, IR700, IR800, and QUASAR 670. Fluorescence labeling agents can include other known fluorophores, or proteins known to the art, for example, green fluorescent protein. The fluorescence labeling agents can be directly or indirectly coupled to the PSMA ligands, administered to a subject or a sample, and the subject/sample examined by fluorescence spectroscopy or imaging to detect the labeled compound. In some embodiments, the fluorescence labeling agent can include a cyanine monosuccinimidyl ester.

In some embodiments, the fluorescence labeling agent can include the cyanine monosuccinimidyl ester, CY5.5. A CY5.5 fluorescence labeling agent can be coupled to the amine group of lysine linked to the PSMA ligand via a carbon spacer arm linker. A carbon spacer arm can include a standard (C6) or a longer spacer arm, such as a (C12) spacer arm. For example, the carbon spacer arm can be a C6, C7, C8, C9, C10, C11, or C12 spacer arm.

Chelating groups (with or without a chelated metal group) can include those disclosed in U.S. Pat. No. 7,351,401, which is herein incorporated by reference in its entirety.

Near infrared imaging groups are disclosed in, for example, Tetrahedron Letters 49(2008) 3395-3399; Angew. Chem. Int. Ed. 2007, 46, 8998-9001; Anal. Chem. 2000, 72, 5907; Nature Biotechnology vol 23, 577-583; Eur Radiol (2003) 13: 195-208; and Cancer 67: 1991 2529-2537, which are herein incorporated by reference in their entirety.

Quantum dots, e.g., semiconductor particles, can be employed as described in Gao, et al "In vivo cancer targeting and imaging with semiconductor quantum dots", Nature Biotechnology, 22, (8), 2004, 969-976, the entire teachings of which are incorporated herein by reference. The PSMA ligands described herein can be coupled to the quantum dots, administered to a subject or a sample, and the subject/sample examined by spectroscopy or imaging to detect the labeled compound.

Magnetic resonance imaging (MRI) contrast agents can include positive contrast agents and negative contrast agents. The PSMA ligands described herein can be coupled to the MRI agents, administered to a subject or a sample, and the subject/sample examined by MRI or imaging to detect the labeled compound. Positive contrast agents (typically appearing predominantly bright on MRI) can include typically small molecular weight organic compounds that chelate or contain an active element having unpaired outer shell electron spins, e.g., gadolinium, manganese, iro, or the like. Typical contrast agents include gadopentetate dimeglumine, gadoteridol, gadoterate meglumine, mangafodipir trisodium, gadodiamide, and others known to the art. Negative contrast agents (typically appearing predominantly dark on MRI) can include small particulate aggregates comprised of superparamagnetic materials, for example, particles of superparamagnetic iron oxide (SPIO). Negative contrast agents can also include compounds that lack the hydrogen atoms associated with the signal in MRI imaging, for example, perfluorocarbons (perfluorochemicals).

In some embodiments, a PSMA targeted conjugate compound that is coupled to a fluorescence labeling agent or infrared agent can have the following general formula:

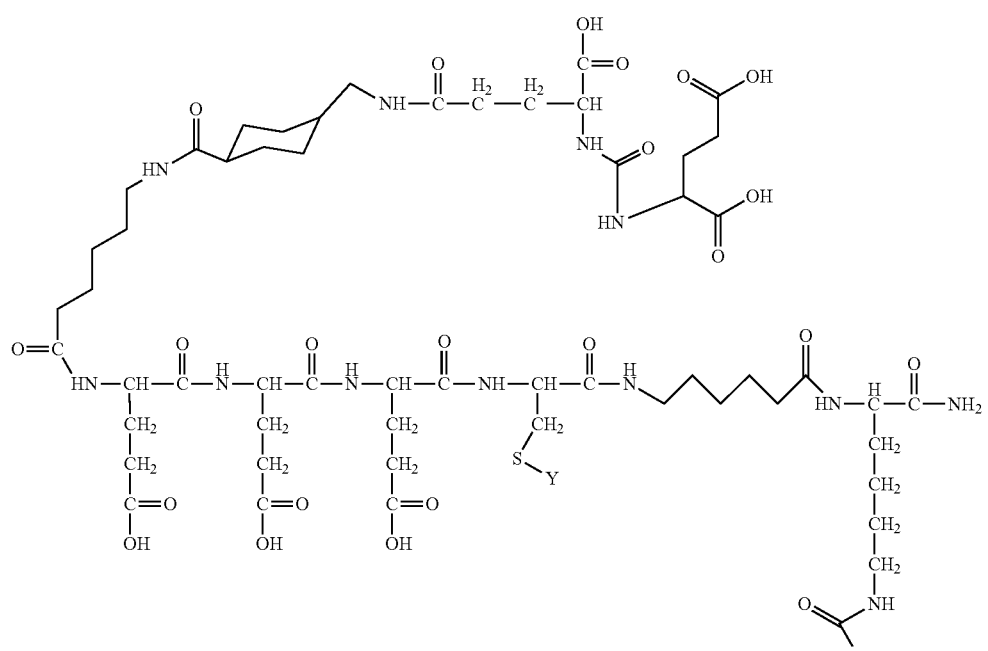

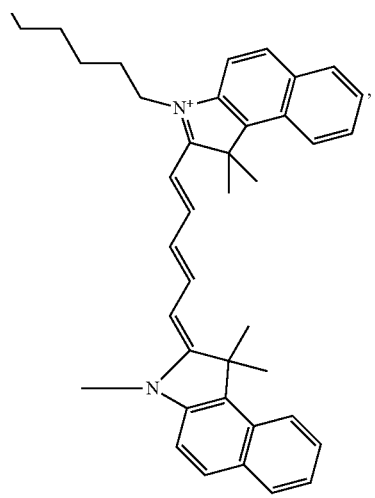

wherein Y is selected from at least one of a detectable moiety, therapeutic agent, or theranostic agent that is directly or indirectly linked to the thiol group. This PSMA targeted conjugate compound can be prepared by linking the cysteine residue of the PSMA ligand to a lysine residue via a C6 linker, which then allows for coupling a detectable moiety, therapeutic agent, or theranostic agent, for example, the fluorescence labeling agent, CY5.5 to the amine on the lysine amino acid.

In some embodiments, a PSMA targeted conjugate compound that is coupled to a fluorescence labeling agent and a therapeutic agent can have the formula:

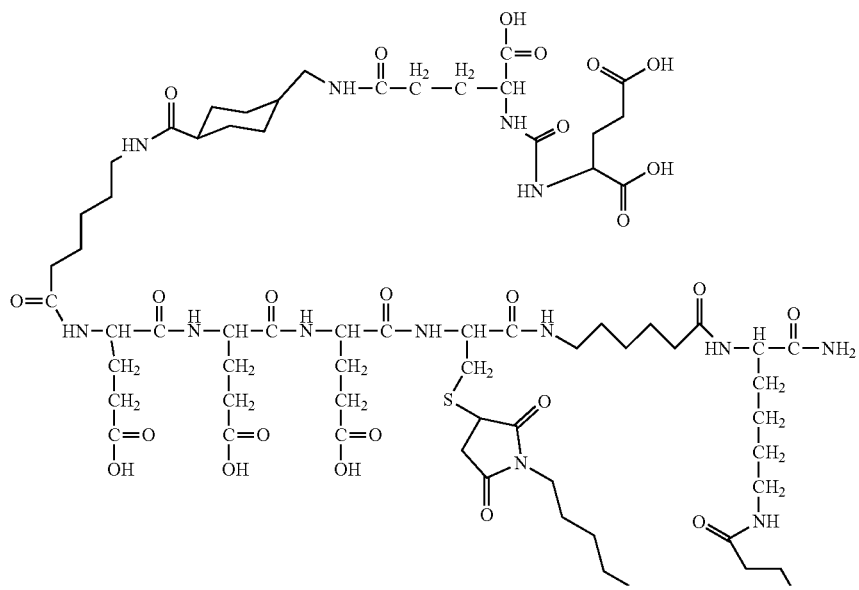

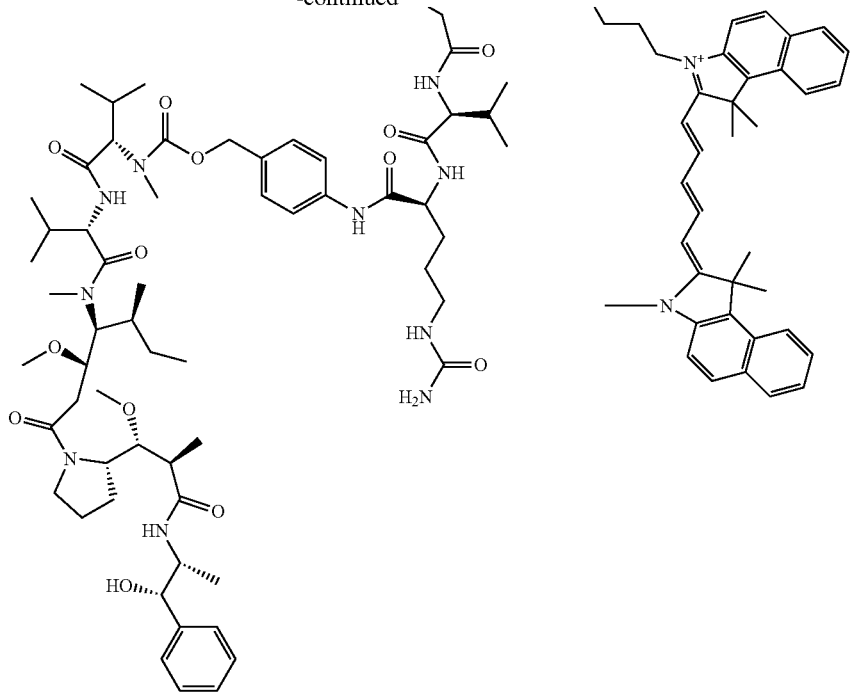

In some aspects, the PSMA ligands coupled to a detectable moiety described herein may be used in conjunction with non-invasive imaging techniques for in vivo imaging, such as magnetic resonance spectroscopy (MRS) or imaging (MRI), or gamma imaging, such as positron emission tomography (PET) or single-photon emission computed tomography (SPECT), to determine the location or distribution of cancer cells. The term "in vivo imaging" refers to any method, which permits the detection of a labeled PSMA targeted conjugate compound, as described above. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of molecular probe along with a large excess of unlabeled, but otherwise chemically identical compound.

For purposes of in vivo imaging, the type of detection instrument available is a major factor in selecting a given detectable moiety. For instance, the type of instrument used will guide the selection of the stable isotope. The half-life should be long enough so that it is still detectable at the time of maximum uptake by the target, but short enough so that the host does not sustain deleterious effects.

The PSMA targeted conjugate compounds coupled to a detectable moiety described herein can be administered to the subject by, for example, systemic, topical, and/or parenteral methods of administration. These methods include, e.g., injection, infusion, deposition, implantation, or topical administration, or any other method of administration where access to the tissue desired. In one example, administration can be by intravenous injection in the subject. Single or multiple administrations of the probe can be given. "Administered", as used herein, means provision or delivery is in an amount(s) and for a period of time(s) effective to label cancer cells in the subject.

The PSMA targeted conjugate compounds coupled to a detectable moiety described herein can be administered to a subject in a detectable quantity of a pharmaceutical composition containing the PSMA targeted conjugate compounds coupled to a detectable moiety described herein or a pharmaceutically acceptable water-soluble salt thereof, to a patient. A "detectable quantity" means that the amount of the detectable compound that is administered is sufficient to enable detection of binding of the compound to the cancer cells. An "imaging effective quantity" means that the amount of the detectable compound that is administered is sufficient to enable imaging of binding of the compound to the cancer cells.

The PSMA targeted conjugate compounds coupled to a detectable moiety described herein administered to a subject can be used to determine the presence, location, and/or distribution of cancer cells, i.e., PSMA expressing cancer cells or PSMA expressing neovasculature of the cancer cells, in an organ or body area of a patient. The presence, location, and/or distribution of the PSMA ligands coupled to a detectable moiety in the animal's tissue, e.g., brain tissue, can be visualized (e.g., with an in vivo imaging modality described above). "Distribution" as used herein is the spatial property of being scattered about over an area or volume. In this case, "the distribution of cancer cells" is the spatial property of cancer cells being scattered about over an area or volume included in the animal's tissue, e.g., prostate tissue. The distribution of the PSMA targeted conjugate compounds coupled to a detectable moiety may then be correlated with the presence or absence of cancer cells in the tissue. A distribution may be dispositive for the presence or absence of a cancer cells or may be combined with other factors and symptoms by one skilled in the art to positively detect the presence or absence of migrating or dispersing cancer cells, cancer metastases or define a tumor margin in the subject.

In some embodiments, the PSMA targeted conjugate compounds coupled to a detectable moiety may be administered to a subject to assess the distribution prostate cells in a subject and correlate the distribution to a specific location. Surgeons routinely use stereotactic techniques and intra-operative MRI (iMRI) in surgical resections. This allows them to specifically identify and sample tissue from distinct regions of the tumor such as the tumor edge or tumor center. Frequently, they also sample regions of prostate on the tumor margin that are outside the tumor edge that appear to be grossly normal but are infiltrated by dispersing tumor cells upon histological examination.

The PSMA targeted conjugate compounds coupled to a detectable moiety can be used in intra-operative imaging techniques to guide surgical resection and eliminate the "educated guess" of the location of the tumor by the surgeon. Previous studies have determined that more extensive surgical resection improves patient survival. Thus, targeted conjugate compounds coupled to a detectable moiety that function as diagnostic molecular imaging agents have the potential to increase patient survival rates.

The PSMA targeted conjugate compounds can be used to deliver a therapeutic anti-cancer agent to a PSMA expressing cancer cell of a subject or mammal. Therefore, some embodiments relate to the administration of a PSMA targeted conjugate compound coupled to an anticancer agent to a subject having or suspected of having cancer, such as a PSMA expressing cancer for the treatment of cancer. In particular embodiments, a PSMA targeted conjugate compounds coupled to an anticancer agent can be administered to a subject having prostate cancer.

The PSMA targeted conjugate compounds can target and transiently interact with, bind to, and/or couple with a cancer cell, such as a prostate cancer cell, and once interacting with, bound to, or coupled to the targeted cell or tissue advantageously facilitate delivery of a therapeutic agent within cell by, for example, receptor mediated endocytosis. Without being bound by theory, where the PSMA targeted conjugate compound includes a therapeutic agent, it is believed that once delivered to a PSMA expressing cell, endosomal conditions can release the therapeutic agent, e.g., doxorubicin, where it travels to the nucleus, binds to DNA and exerts anti-proliferative effects.

Examples of anticancer agents that can be directly or indirectly coupled to a PSMA targeting conjugate compound as described herein can include, but are not limited to Taxol, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; elformithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon α-2a; interferon α-2b; interferon α-n1; interferon α-n3; interferon β-I a; interferon γ-T b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of anti-cancer agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; silicon phthalocyanine (PC4) sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans (GAGs); tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Still other examples of anti-cancer agents can include the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCl), Resverastatin phosphate sodium, BPR-OY-007 (National Health Research Institutes), and SSR-250411 (Sanofi).

Other examples of anti-cancer agents include alkylating agents, such as nitrogen mustards (e.g., mechlorethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomustine, semustine, streptozocin, etc.), or triazenes (decarbazine, etc.), antimetabolites, such as folic acid analog (e.g., methotrexate), or pyrimidine analogs (e.g., fluorouracil, floxuridine, Cytarabine), purine analogs (e.g., mercaptopurine, thioguanine, pentostatin, vinca alkaloids (e.g., vinblastin, vincristine), epipodophyllotoxins (e.g., etoposide, teniposide), platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, amino glutethimide).

In certain embodiments, the anti-cancer agent coupled to a PSMA targeted conjugate compound is selected from doxorubicin or monomethyl auristatin E (MMAE). In particular embodiments, the anti-cancer agent is coupled to the PSMA targeted conjugate compound. In an embodiment, a PSMA targeted conjugate compound that is coupled to a therapeutic anti-cancer agent can have the formula:

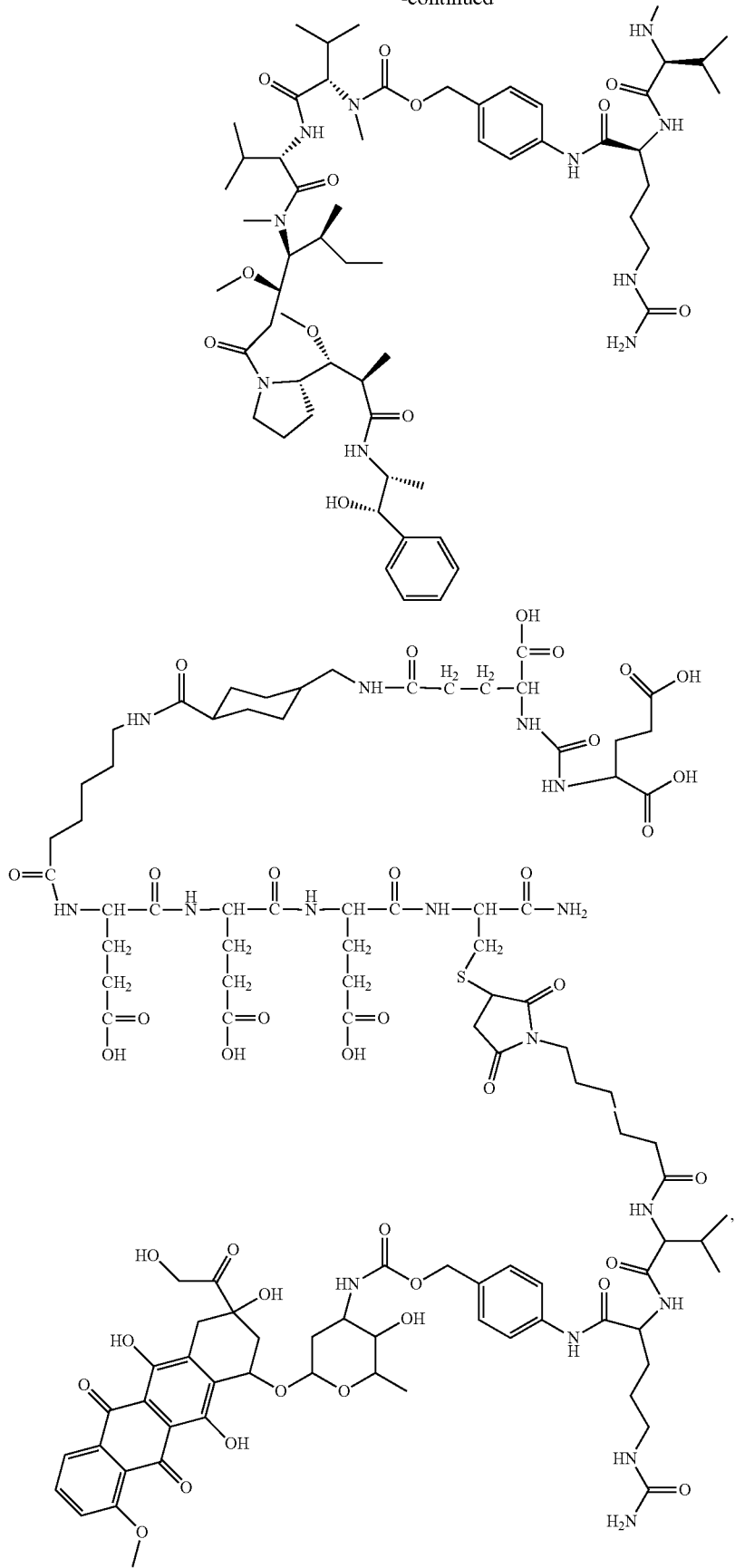

-continued

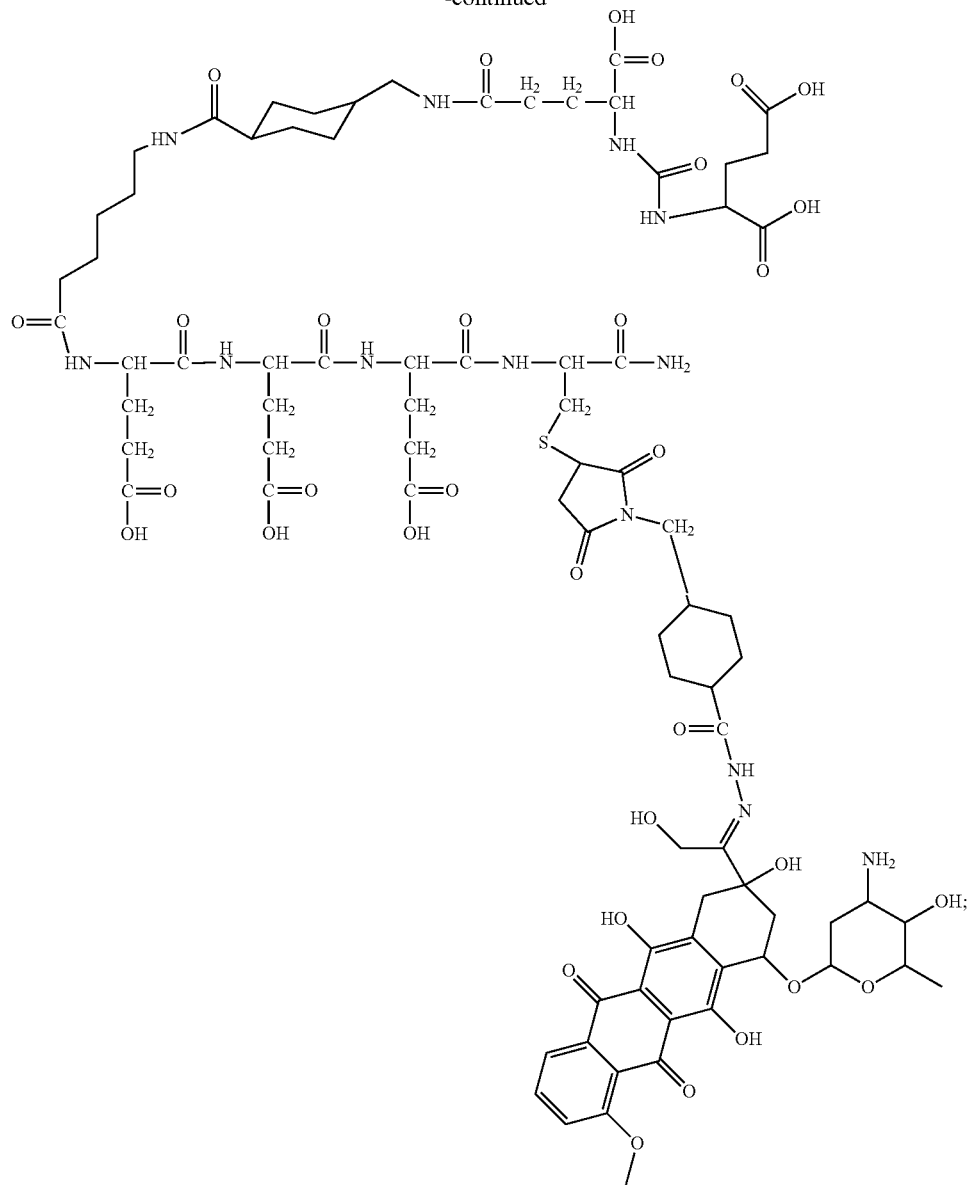 [SMILES: COc1cccc2c1C(=O)c1c(O)c3c(c(O)c1C2=O)CC(O)(/C(CO)=N/NC(=O)C1CCC(CN2C(=O)CC(SCC(NC(=O)C(CCC(=O)O)NC(=O)C(CCC(=O)O)NC(=O)C(CCC(=O)O)NC(=O)CCCCCNC(=O)C4CCC(CNC(=O)CCC(NC(=O)NC(CCC(=O)O)C(=O)O)C(=O)O)CC4)C(N)=O)C2=O)CC1)CC3OC1CC(N)C(O)C(C)O1]

or pharmaceutical salts thereof.

The PSMA targeting conjugate compounds can be administered alone as a monotherapy, or in conjunction with or in combination with one or more additional therapeutic agents. In some embodiments, a PSMA targeting conjugate compound described herein can be administered to the subject in combination with an additional anti-cancer agent. In a particular embodiment, a PSMA targeting conjugate compound is coupled to doxorubicin as described herein can be administered to the subject in combination with the anti-cancer agent docetaxel.

It will be appreciated that additional detectable moieties, therapeutic agents, and/or theranostic agents administered to a subject need not be conjugated directly or indirectly to the PSMA ligand of the PSMA targeting compound and can optionally be provided in a pharmaceutical composition or preparation with the PSMA targeting conjugate compounds described herein or in a separate pharmaceutical composition.

The term "in conjunction with" or "in combination with" indicates that the PSMA targeting conjugate compound is administered at about the same time as the additional agent. The PSMA targeting conjugate compound can be administered to the subject in need thereof as part of a pharmaceutical composition comprising the compound and a pharmaceutically acceptable carrier or excipient and, optionally, one or more additional therapeutic agents. The compound and additional therapeutic agent can be components of separate pharmaceutical compositions, which can be mixed together prior to administration or administered separately. The PSMA targeting conjugate compound can, for example, be administered in a composition containing the additional therapeutic agent, and thereby, administered contemporaneously with the agent. Alternatively, the PSMA targeting conjugate compound can be administered contemporaneously, without mixing (e.g., by delivery of the compound on the intravenous line by which the compound is also administered, or vice versa). In another embodiment, the PSMA targeting conjugate compound can be administered separately (e.g., not admixed), but within a short timeframe (e.g., within 24 hours) of administration of the compound.

The disclosed PSMA targeting conjugate compounds and additional therapeutic agents, detectable moieties, and/or theranostic agents described herein can be administered to a subject by any conventional method of drug administration, for example, orally in capsules, suspensions or tablets or by parenteral administration. Parenteral administration can include, for example, intramuscular, intravenous, intraventricular, intraarterial, intrathecal, subcutaneous, or intraperitoneal administration. The disclosed compounds can also be administered orally (e.g., in capsules, suspensions, tablets or dietary), nasally (e.g., solution, suspension), transdermally, intradermally, topically (e.g., cream, ointment), inhalation (e.g., intrabronchial, intranasal, oral inhalation or intranasal drops) transmucosally or rectally. Delivery can also be by injection into the brain or body cavity of a patient or by use of a timed release or sustained release matrix delivery systems, or by onsite delivery using micelles, gels and liposomes. Nebulizing devices, powder inhalers, and aerosolized solutions may also be used to administer such preparations to the respiratory tract. Delivery can be in vivo, or ex vivo. Administration can be local or systemic as indicated. More than one route can be used concurrently, if desired. The preferred mode of administration can vary depending upon the particular disclosed compound chosen. In specific embodiments, oral, parenteral, or systemic administration (e.g., intravenous) are preferred modes of administration for treatment.

The methods described herein contemplate either single or multiple administrations, given either simultaneously or over an extended period of time. The PSMA targeting conjugate compound (or composition containing the compound) can be administered at regular intervals, depending on the nature and extent of the inflammatory disorder's effects, and on an ongoing basis. Administration at a "regular interval," as used herein, indicates that the therapeutically effective amount is administered periodically (as distinguished from a one-time dose). In one embodiment, the PSMA targeting conjugate compound is administered periodically, e.g., at a regular interval (e.g., bimonthly, monthly, biweekly, weekly, twice weekly, daily, twice a day or three times or more often a day).

The administration interval for a single individual can be fixed, or can be varied over time, depending on the needs of the individual. For example, in times of physical illness or stress, or if disease symptoms worsen, the interval between doses can be decreased. Depending upon the half-life of the agent in the subject, the agent can be administered between, for example, once a day or once a week.

For example, the administration of the PSMA targeting conjugate compound described herein and/or the additional therapeutic agent can take place at least once on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least once on week 1, 2, 3, 4, 5, 6, 7, 8, 9, 10, 11, 12, 13, 14, 15, 16, 17, 18, 19 or 20, or any combination thereof, using single or divided doses of every 60, 48, 36, 24, 12, 8, 6, 4, or 2 hours, or any combination thereof. Administration can take place at any time of day, for example, in the morning, the afternoon or evening. For instance, the administration can take place in the morning, e.g., between 6:00 a.m. and 12:00 noon; in the afternoon, e.g., after noon and before 6:00 p.m.; or in the evening, e.g., between 6:01 p.m. and midnight.

A disclosed PSMA targeting conjugate compound and/or additional therapeutic agent can be administered in a dosage of, for example, 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day. Dosage forms (composition) suitable for internal administration generally contain from about 0.1 milligram to about 500 milligrams of active ingredient per unit. In these pharmaceutical compositions, the active ingredient will ordinarily be present in an amount of about 0.5-95% by weight based on the total weight of the composition.

The amount of disclosed PSMA targeting conjugate compound and/or additional therapeutic agent administered to the subject can depend on the characteristics of the subject, such as general health, age, sex, body weight and tolerance to drugs as well as the degree, severity and type of rejection. The skilled artisan will be able to determine appropriate dosages depending on these and other factors using standard clinical techniques.

In addition, in vitro or in vivo assays can be employed to identify desired dosage ranges. The dose to be employed can also depend on the route of administration, the seriousness of the disease, and the subject's circumstances. Effective doses may be extrapolated from dose-response curves derived from in vitro or animal model test systems. The amount of the compound can also depend on the disease state or condition being treated along with the clinical factors and the route of administration of the compound.

For treating humans or animals, the amount of disclosed PSMA targeting conjugate compound and/or additional therapeutic agent administered (in milligrams of compound per kilograms of subject body weight) is generally from about 0.1 mg/kg to about 100 mg/kg, typically from about 1 mg/kg to about 50 mg/kg, or more typically from about 1 mg/kg to about 25 mg/kg. In a preferred embodiment, the effective amount of agent or PSMA targeting conjugate compound is about 1-10 mg/kg. In another preferred embodiment, the effective amount of agent or PSMA targeting conjugate compound is about 1-5 mg/kg. The effective amount for a subject can be varied (e.g., increased or decreased) over time, depending on the needs of the subject.

The term "unit dose" refers to a physically discrete unit suitable as unitary dosage for the subject, each unit containing a predetermined quantity of active material that can produce the desired therapeutic effect in association with the required diluent; e.g., carrier or vehicle. In addition to the ingredients particularly mentioned above, the formulations of the present invention may include other agents conventional in the art having regard to the type of formulation in question.

The disclosed PSMA targeting conjugate compound and/or additional therapeutic agent described herein can be administered to the subject in conjunction with an acceptable pharmaceutical carrier or diluent as part of a pharmaceutical composition for therapy. Formulation of the PSMA targeting conjugate compound to be administered will vary according to the route of administration selected (e.g., solution, emulsion, capsule, and the like). Suitable pharmaceutically acceptable carriers may contain inert ingredients that do not unduly inhibit the biological activity of the PSMA targeting conjugate compounds. The pharmaceutically acceptable carriers should be biocompatible, e.g., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

The preparation of a pharmacological composition that contains active ingredients dissolved or dispersed therein is well understood in the art. Typically, such compositions are prepared as injectables as either liquid solutions or suspensions, however, solid forms suitable for solution, or suspensions, in liquid prior to use can also be prepared. Formulation will vary according to the route of administration selected (e.g., solution, emulsion, capsule).

A pharmaceutically acceptable carrier for a pharmaceutical composition can also include delivery systems known to the art for entraining or encapsulating drugs, such as anticancer drugs. In some embodiments, the disclosed compounds can be employed with such delivery systems including, for example, liposomes, nanoparticles, nanospheres, nanodiscs, dendrimers, and the like. See, for example Farokhzad, O. C., Jon, S., Khademhosseini, A., Tran, T. N., Lavan, D. A., and Langer, R. (2004). "Nanoparticle-aptamer bioconjugates: a new approach for targeting prostate cancer cells." Cancer Res., 64, 7668-72; Dass, C. R. (2002). "Vehicles for oligonucleotide delivery to tumours." J. Pharm. Pharmacol., 54, 3-27; Lysik, M. A., and Wu-Pong, S. (2003). "Innovations in oligonucleotide drug delivery." J. Pharm. Sci., 92, 1559-73; Shoji, Y., and Nakashima, H. (2004). "Current status of delivery systems to improve target efficacy of oligonucleotides." Curr. Pharm. Des., 10, 785-96; Allen, T. M., and Cullis, P. R. (2004). "Drug delivery systems: entering the mainstream." Science, 303, 1818-22. The entire teachings of each reference cited in this paragraph are incorporated herein by reference.

The following examples are for the purpose of illustration only and are not intended to limit the scope of the claims, which are appended hereto.

Example 1

PSMA-1 Doxorubicin Conjugates for Targeted Therapy of Prostate Cancer

In this Example we show a highly negatively-charged peptide-based PSMA receptor ligand, PSMA-1, with affinity in the nM range, can improve the efficacy and widen the therapeutic window of the commonly used chemotherapeutic agent, doxorubicin. Clinically, doxorubicin's use is not optimal due to significant toxicities including cardiotoxicity and myelosuppression, effects which may be decreased with improved tumor-targeting.

We attached PSMA-1 to doxorubicin with different linkages that can be cleaved via proteases or the acidic environment found at/within most tumors. With this prodrug strategy, demonstrated in FIG. 1 and FIG. 2, doxorubicin can dissociate from PSMA-1 inside of a cancer cell or in the extracellular milieu and exert its anti-proliferative effects freely. Further, we will exploit the inactivity of conjugated doxorubicin to decrease off target toxicity typically found with the free or liposome-incorporated drug. In summary, we show PSMA-1-Doxorubicin conjugates will be selectively taken up by PSMA-expressing prostate cancer cells, and these drugs exhibit equal or superior antineoplastic effects in vitro and in vivo compared to free doxorubicin with minimal off-target toxicity.

Figure 2:
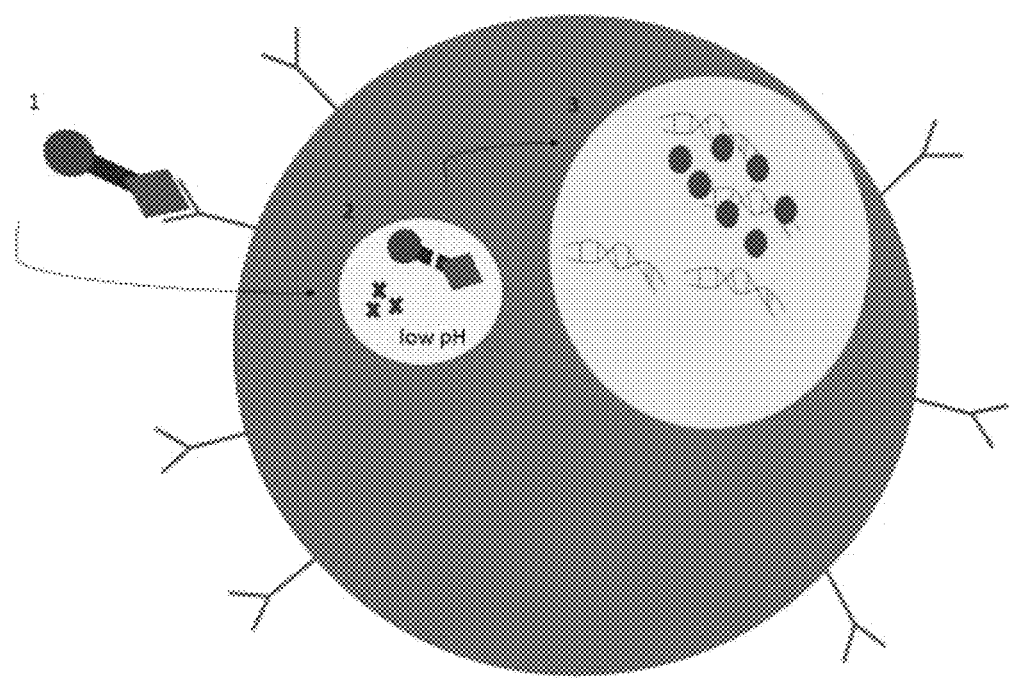
FIG. 2 illustrates proposed mechanisms for prodrug release of free doxorubicin.

FIG. 1 illustrates our reaction schema, in brief. We use a series of three linkers to join the PSMA-1 ligand to doxorubicin:

1. Non-cleavable linker, SMCC (succinimidyl 4-(N-maleimidomethyl)cyclohexane-1-carboxylate). Use of this linker does not yield a true prodrug as with the other two linkers below.

2. Protease-cleavable linker, MC-Val-Cit-PABC-PNP (Maleimidocaproyl-L-Valine-L-Citrulline-p-Aminobenzyl Alcohol p-Nitrophenyl Carbonate). This is the linker utilized in the FDA approved antibody-drug conjugate brentuximab vedotin for treatment of Hodgkin's disease, and consists of MC and PABC spacers sandwiching the cathepsin B-sensitive dipeptide, valine-citrulline. Cathepsin B cleaves the valine-citrulline bond, the PABC spacer is self-immolative, and intact doxorubicin in its native state should be released.

3. Acid-labile hydrazone linker, MMCCH (4-(4-maleimidomethyl)cyclohexane-1-carboxyl hydrazide). The hydrozone bond cleaves releasing doxorubicin in its native state.

Methods

Materials

Fmoc rink amide MBHA resin and Fmoc amino acids were purchased from Peptide International Inc, Novabiochem, and Advanced Biochemical Compounds. Doxorubicin HCl was purchased from LC Laboratories. SMCC was purchased from ThermoFisher. MC-Val-Cit-PABC-PNP was purchased from MedChem Express. MMCCH TFA was purchased from Chem-Impex International Inc. Basic solvents and laboratory supplies were purchased from ThermoFisher and Sigma Aldrich.

General Comments

Preparative high-performance liquid chromatography (HPLC) was used for all purifications, unless otherwise noted. A Shimadzu HPLC system was utilized with a UV/visible detector monitored at 220 nm. A Luna 5μ $C_{18}$(2) 100A column (250 mm×10 mm×5 m, Phenomenex, Torrance, CA) was used at a flow rate of 2.5 ml/min. Gradients and buffers as noted below.

Synthesis of PSMA-1(Cys) (Glu-CO-Glu'-Amc-Ahx-Glu-Glu-Glu-Cys-NH$_2$)

PSMA-1(Cys) was synthesized as PSMA-1 has been described before, with a substitution of cysteine in place of the terminal lysine to provide the —SH group necessary for reaction with the maleimide group of each linker. PSMA-1 (Cys) was synthesized manually using standard Fmoc chemistry. Generally, peptide was synthesized at 0.2 mmol scale starting from C-terminal Fmoc-rink amide MBHA resin.

Resin was allowed to soak in dimethylformamide (DMF) overnight before beginning synthesis. Fmoc deprotection initially and for each coupling cycle was carried out using 20% piperidine in DMF, applied to resin and shaken for 5 minutes. Coupling reactions were carried out using 3.3 equivalents of Fmoc amino acids in DMF activated with 3.3 equivalents of 2-(6-chloro-1H-benzotriazole-1-yl)-1,1,3,3-tetramethylaminium hexafluorophosphate (HCTU) and 5 equivalents of diisopropylethylamine (DIPEA) in DMF, with this mixture applied to the resin and shaken for 30 minutes. These alternating steps (deprotection, new peptide, repeat) were used to build the peptide sequence Fmoc-Glu'-Amc-Ahx-Glu-Glu-Glu-Cys(Mtt) on the resin.

The Fmoc group of N-terminal amino acid Glu' was deprotected by 20% piperidine. A chloroform solution containing 3 equivalents of H-Glu(OtBu)-OtBu mixed with 2.5 equivalents of DIPEA was prepared. The solution was then added slowly to 0.25 equivalents triphosgene in chloroform over 10 minutes at room temperature. After 15-minute incubation, the reaction blend was mixed with Glu'-Amc-Ahx-Glu-Glu-Glu-Lys on rink amide resin preswollen in chloroform with 2.5 equivalents of DIPEA. After the reaction was complete, the resin was washed with DMF and then dichloromethane and dried. The peptide was cleaved from resin by TFA/water/triisopropylsilane (950:25:25).

The cleaved peptide was purified by preparative high-performance liquid chromatography (HPLC). The gradient was 5-55% acetonitrile against 0.1% trifluoroacetic acid over 30 minutes, followed by 15 minutes of 55% acetonitrile. Peptide retention time was 21 minutes. Expected structures were confirmed by molecular weight using electrospray mass spectrometry (MS). Peptide was lyophilized and stored at −20° C.

Synthesis of PSMA-1-Doxorubicin Conjugates

Generally, each linker was reacted with an excess of doxorubicin in DMF and purified by HPLC, resulting in a maleimide-functionalized doxorubicin. Next, the cysteine tail of the PSMA ligand was reacted with the maleimide group on the linker to form the final conjugate. (Doxorubicin is light-sensitive and was handled with special care to wrap tubes in aluminum foil to prevent light exposure). The final conjugate was again purified by HPLC and lyophilized for storage at −20° C. The structures at each reaction step were confirmed using either electrospray MS or MALDI-MS. Our electrospray MS machine generally produced cleaner images and was used when available. MALDI was used in other cases or if MW of the compound exceeded 2200, the maximum electrospray capacity. Our PSMA-targeted conjugates do make use of the modified PSMA-1(Cys), but for simplicity they will be referred to as PSMA-1-Doxorubicin conjugates.

Synthesis of PSMA-1-SMCC-Dox

To produce the maleimide-functionalized doxorubicin, SMCC was dissolved in DMF with the addition of triethylamine (TEA) to adjust the solution pH to approximately 8, measured roughly with pH paper. To this, 1.1 equivalents of doxorubicin HCl was added. The mixture was allowed to mix in the dark overnight at room temperature before purification by HPLC using a gradient of 30-90% acetonitrile against 0.1% trifluoroacetic acid over 40 minutes. Retention time for unreacted doxorubicin was 13 minutes, unreacted SMCC was 23.5 minutes, and the product SMCC-Dox was 24.5 minutes.

To produce PSMA-1-SMCC-Dox, SMCC-Dox was reacted with 1.1 equivalents PSMA-1(Cys) in DMF with pH adjustment to 8 by TEA. The solution was allowed to mix overnight in dark conditions at room temperature. The same HPLC gradient was used resulting in a retention time for the final product of 17 minutes. Unreacted PSMA-1(Cys) elutes with the solvent DMF. The reaction generally went to completion with no unreacted SMCC-Dox.

Synthesis of PSMA-1-MC-Val-Cit-PABC-Dox

To produce the maleimide-functionalized doxorubicin, MC-Val-Cit-PABC-PNP was reacted with 1.1 equivalents doxorubicin HCl and 1.1 equivalents DIPEA in DMF. It was left to react on a spinner in the dark for two days at room temperature. This single reaction was purified without using HPLC. Instead, ~10× volume excess CH2Cl2 was added to the reaction mixture and this was left to sit overnight at −20 to precipitate the product MC-Val-Cit-PABC-Dox. The resultant solid was isolated by centrifugation.

To produce PSMA-1-MC-Val-Cit-PABC-Dox, the MC-Val-Cit-PABC-Dox was reacted with 1.1 equivalents of PSMA-1(Cys) in DMF with pH adjusted to 7-8 using TEA. This was allowed to spin in the dark overnight. The product was purified with HPLC using a gradient of 30-90% acetonitrile against 0.1% trifluoroacetic acid over 40 minutes. Retention time was 17 minutes. Unreacted PSMA-1(Cys) elutes with the solvent DMF. This reaction generally went to completion with no unreacted MC-Val-Cit-PABC-Dox.

Synthesis of PSMA-1-MMCCH-Dox

To produce the maleimide-functionalized doxorubicin, MMCCH TFA was reacted with 1.1 equivalents doxorubicin HCl in DMF at 50 C for 2 hours in a dark fume hood. The product was purified with HPLC using a gradient of 30-90% acetonitrile against 2 mM TEAA. A basic buffer was chosen to avoid lysis of the acid-labile linkage. Retention time of the uncreated MMCCH was 8 minutes, unreacted doxorubicin was 15 minutes, and MMCC-Dox was 19 minutes.

To produce PSMA-1-MMCCH-Dox, MMCCH-Dox was reacted with 1.1 equivalents PSMA-1(Cys) in DMF with pH adjusted to 8 using TEA. This was mixed overnight and the product purified using an HPLC gradient of 10-90% acetonitrile against 2 mM TEAA. Product retention time was 19 minutes. Unreacted PSMA-1(Cys) elutes with the solvent DMF. This reaction generally went to completion with no unreacted MMCCH-Dox.

Cell Culture

Retrovirally transfected PSMA-positive PC3pip cells and control PC3flu cells were used for all experiments. Cells were cultured at 37 C in a 5% $CO_2$, humidified atmosphere. Cultures were maintained in RPMI-1640 medium supplemented with 10% fetal bovine serum (FBS).

In Vitro Cellular Uptake Studies

PC3Pip and PC3flu cells ($1.5 \times 10^5$) were plated on coverslips and allowed to adhere for 36-48 hours. Cells were incubated in 1 µM of free doxorubicin or the various PSMA-1-Doxorubicin conjugates in RPMI media. Similar experiments are reported widely in the literature, with doses usually in the µM range because of doxorubicin's relatively dim fluorescence, at least compared with some of the commercially available dyes used in our lab. This dose was chosen to balance that relatively dim fluorescence with a goal of attempting to maintain selectivity.

The PSMA-1-Doxorubicin conjugates were not soluble in water. Stock solutions were prepared in dimethyl sulfoxide, DMSO, for short term storage. Experimental dilutions were prepared in RPMI media. An extinction coefficient of 10410 liter/(mol cm) was used, as reported in the literature, for dilution calculations using the Beer-Lambert Law after absorption was measured at 480 nm.

Next, cells were washed 3 times with RPMI media, fixed with 4% paraformaldehyde for 10 minutes, and washed twice with phosphate-buffered saline (PBS). The cells were counterstained with DAPI nuclear staining, mounted on microscope slides with a 50% mounting solution mixture of PBS and glycol, and the coverslips were sealed with clear nail polish. Fluorescent imaging was performed with Leica DM4000B fluorescence microscopy. DAPI imaging used the Blue filter with excitation/emission at 410/455 nm. Doxorubicin was imaged with the Texas Red filter with Ex/Em 587/612 nm.

Cytotoxicity Assay

PC3Pip and PC3Flu cells (2000 cells/100 µL/well) were plated in 96 well plates and rested for 24 hours to adhere to the plate surface. To each well, we added 10 µL of an 11× concentrated solution of doxorubicin or conjugate. Each drug dose was tested in groups of six wells. Dojindo CCK8 assays were used to determine relative cell survival of treated wells compared with untreated controls. This is a calorimetric assay for determination of cell viability and proliferation. A water-soluble tetrazolium salt, WST-8, is reduced by dehydrogenase activity in the cell which produces an orange dye with relative amounts quantified by absorbance. Briefly, 10 µL assay solution was added to each well, the plate was left to incubate while orange color was produced, the absorption of the solution in the plate was read at 450 nm, and the cell viabilities were calculated.

Mouse Tumor Xenograft Studies

All animal procedures were performed according to the protocols approved by the Institutional Animal Care and Use Committee (IACUC). Our approval is Case Western Reserve University IACUC #2015-0033. Athymic nude mice aged 6-8 weeks were implanted subcutaneously with 1×106 PC3Pip cells in 100 µL Matrigel on the right flank. Tumors were allowed to grow for two weeks. Mice were then treated with three doses of free doxorubicin or PSMA-1-MMCCH-Dox in PBS on day 0, 7, and 14 of the study via tail vein injection. Dose used was 2 mg/kg doxorubicin, or the equivalent molar dosage of the PSMA-targeted prodrug. Tumor dimensions were measured using calipers twice per week, and mouse weights were recorded on these days, as well. The study duration was 21 days.

Statistical Analysis

Statistical analysis was performed using student t-test with a p<0.05 meeting criteria for statistical significance. Analysis was performed using JMP Pro 13 software.

Results

Chemistry

Figure 3:
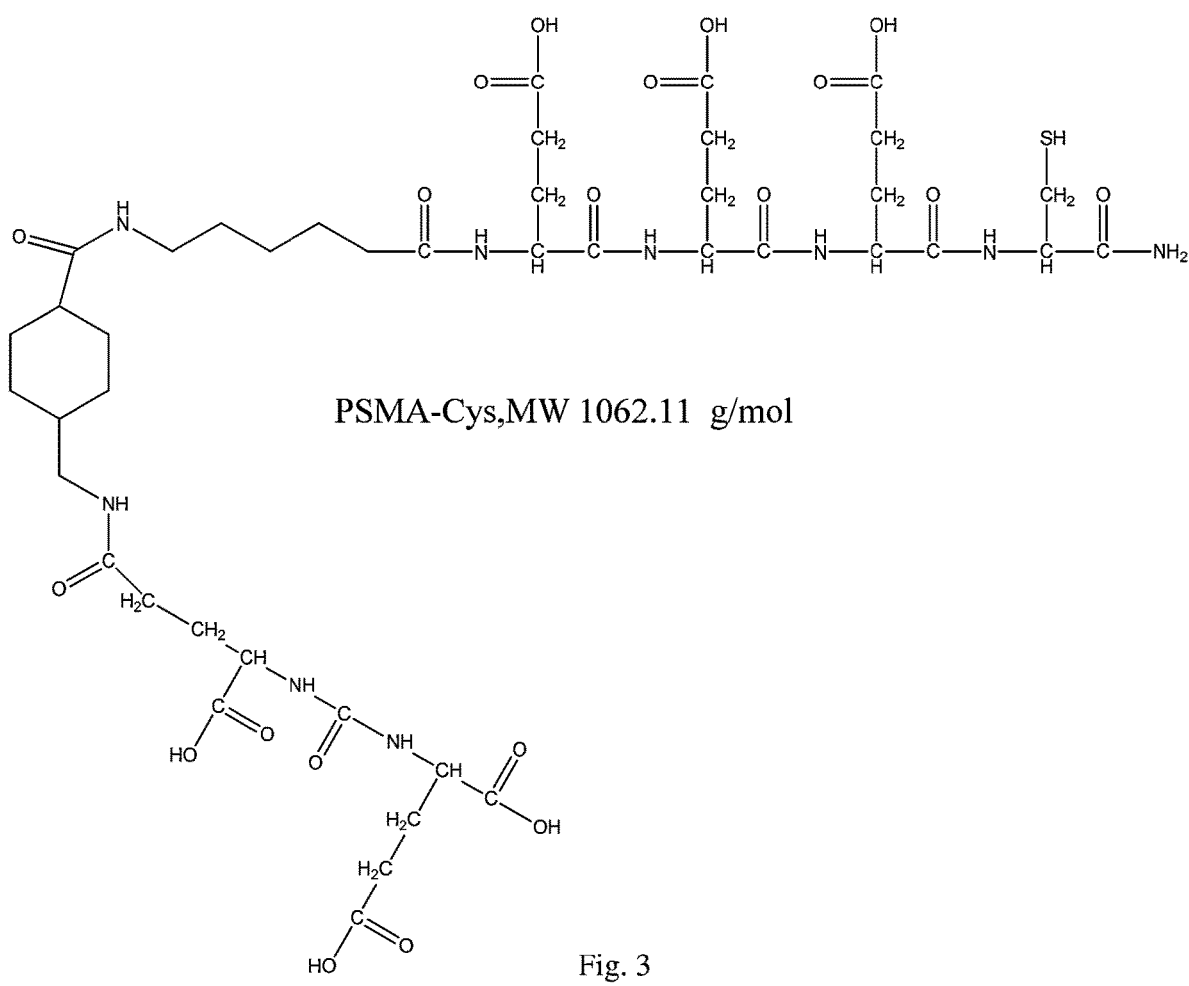
FIG. 3 illustrates a structure of PSMA-1(Cys)

PSMA-1(Cys) is a modified version of a PSMA-1 peptide ligand. It is a urea-based ligand with three glutamic acid residues providing a negative charge that has been previously shown to reduce non-specific background binding without negatively influencing PSMA affinity. The terminal cysteine allows for easy coupling of the —SH group to the maleimide in each of the linkers chosen. PSMA-1(Cys) was successfully synthesized by Fmoc chemistry by hand, with an electrospray MS peak showing 1062.4 g/mol. This was consisted with the calculated molecular weight using Chem Draw Professional of 1062.1 g/mol, as demonstrated in FIG. 3.

Figure 4:
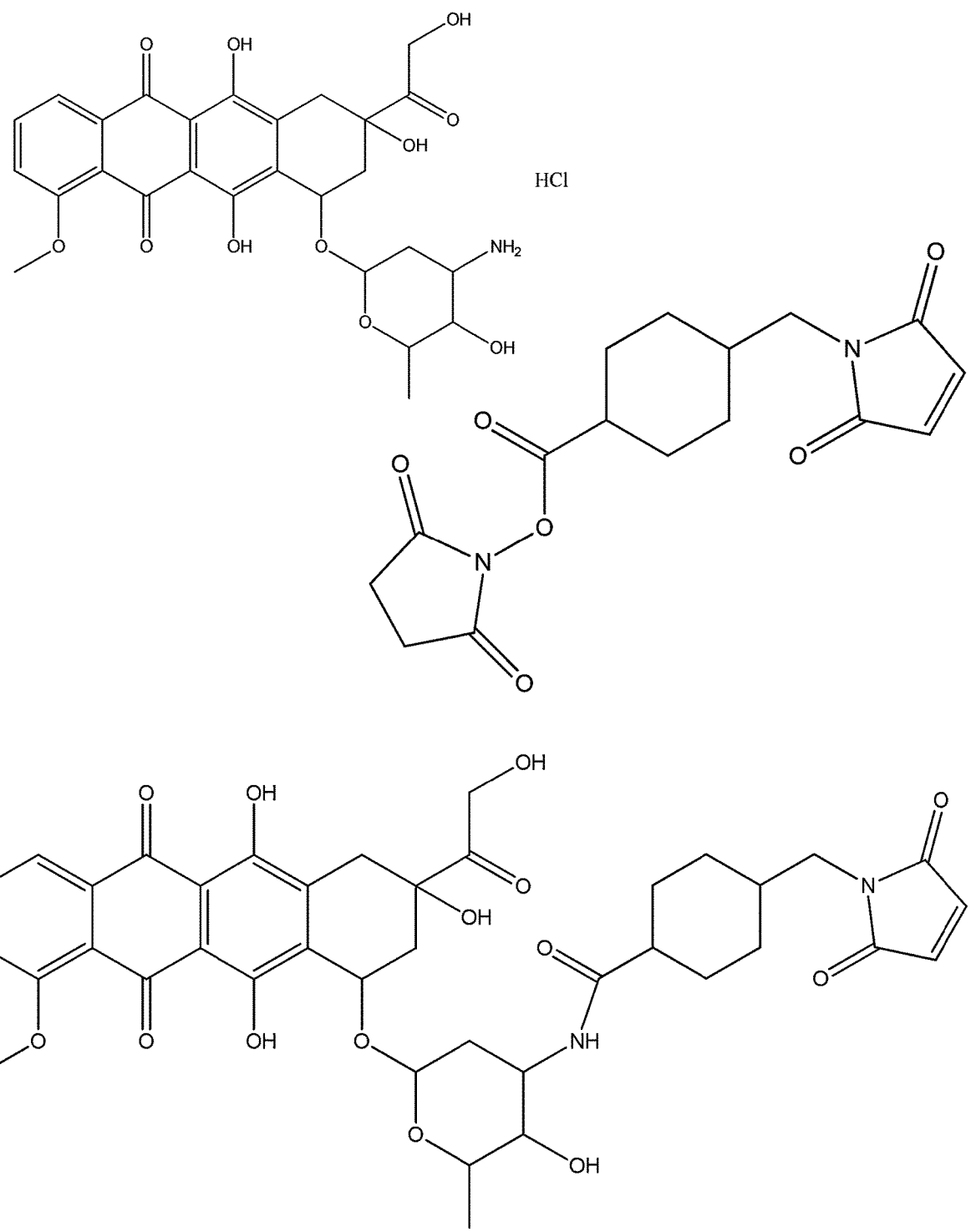
FIG. 4 illustrates the synthesis of SMCC-Dox
Figure 5:
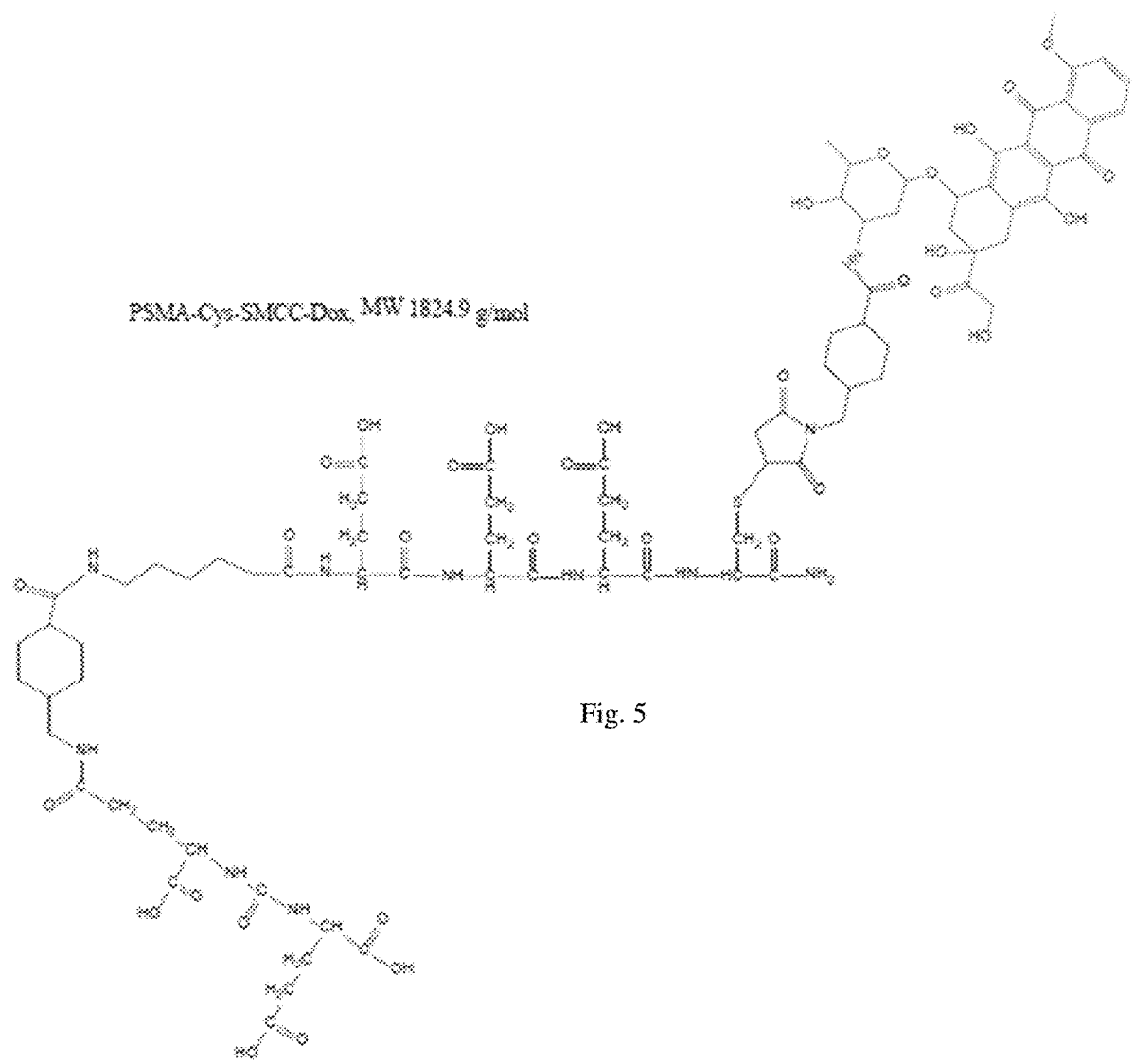
FIG. 5 illustrates the synthesis of Non-cleavable PSMA-1-SMCC-Dox.

The non-cleavable PSMA-1-SMCC-Dox conjugate was synthesized by allowing the NHS ester in SMCC to react with the —NH$_2$ present in doxorubicin. Expected molecular weight for this compound was 762.3. MALDI-MS of SMCC-Dox showed a strong peak at 785.4, consistent with MW+Na, and confirming successful conjugation. The full PSMA-1-SMCC-Dox conjugate was also successfully produced when the —SH of cysteine in the linker combined with the maleimide end of the SMCC linker. The expected molecular weight for this compound was 1824.9. See FIGS. 4 and 5.

Figure 6:
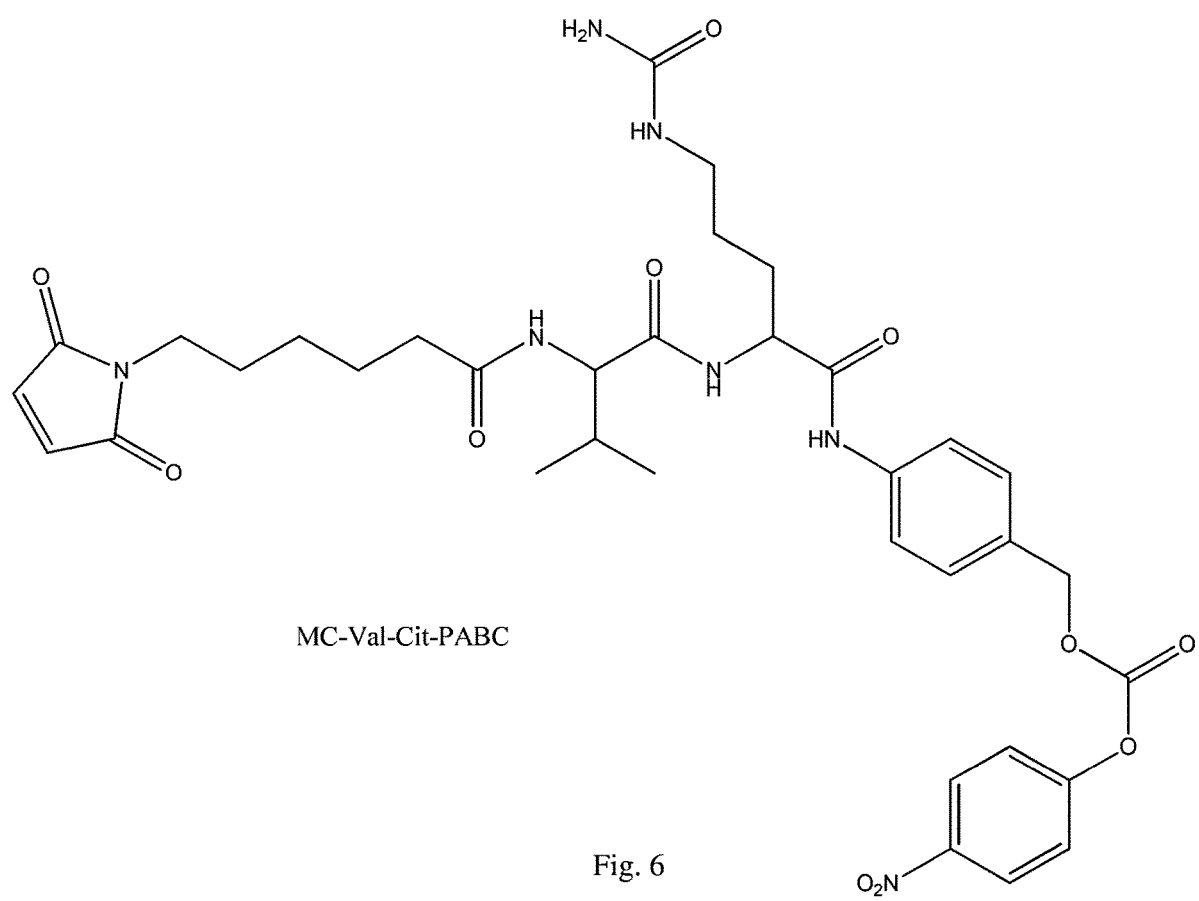
FIG. 6 illustrates the synthesis of MC-Val-Cit-PABC-Dox
Figure 7:
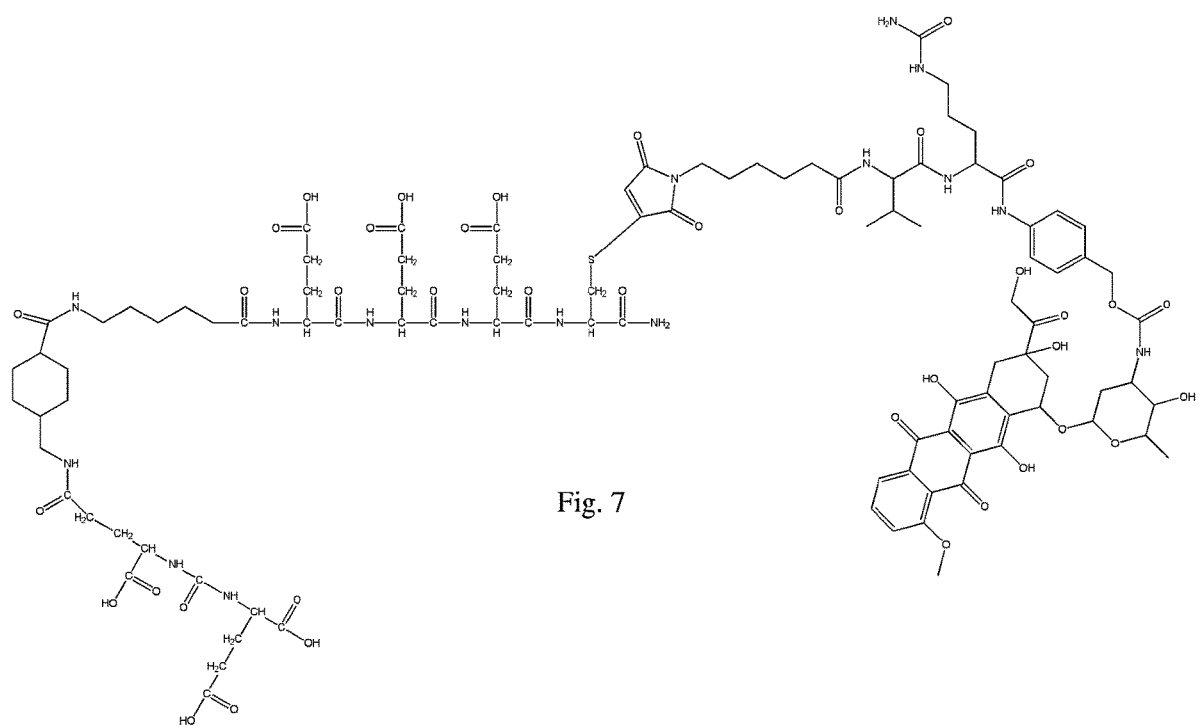
FIG. 7 illustrates the synthesis of cathepsin-cleavable PSMA-1-MC-Val-Cit-PABC-Dox

Similarly, the production of the protease-cleavable PSMA-1-MC-Val-Cit-PABC-Dox was achieved by reaction of the NHS ester group in the MC-Val-Cit-PABC-PNP linker with the amine in doxorubicin. The expected MW was 1142.2, and MALDI-MS demonstrated a peak at 1164.2, consistent with MW+Na. The —SH in PSMA-1(Cys) reacts nicely with the maleimide group of the linker to produce the final product, with MALDI-MS showing a peak at 2225.6, again consistent with MW+NA (expected MW 2204.3). See FIGS. 6 and 7 for reaction data.

Figure 8:
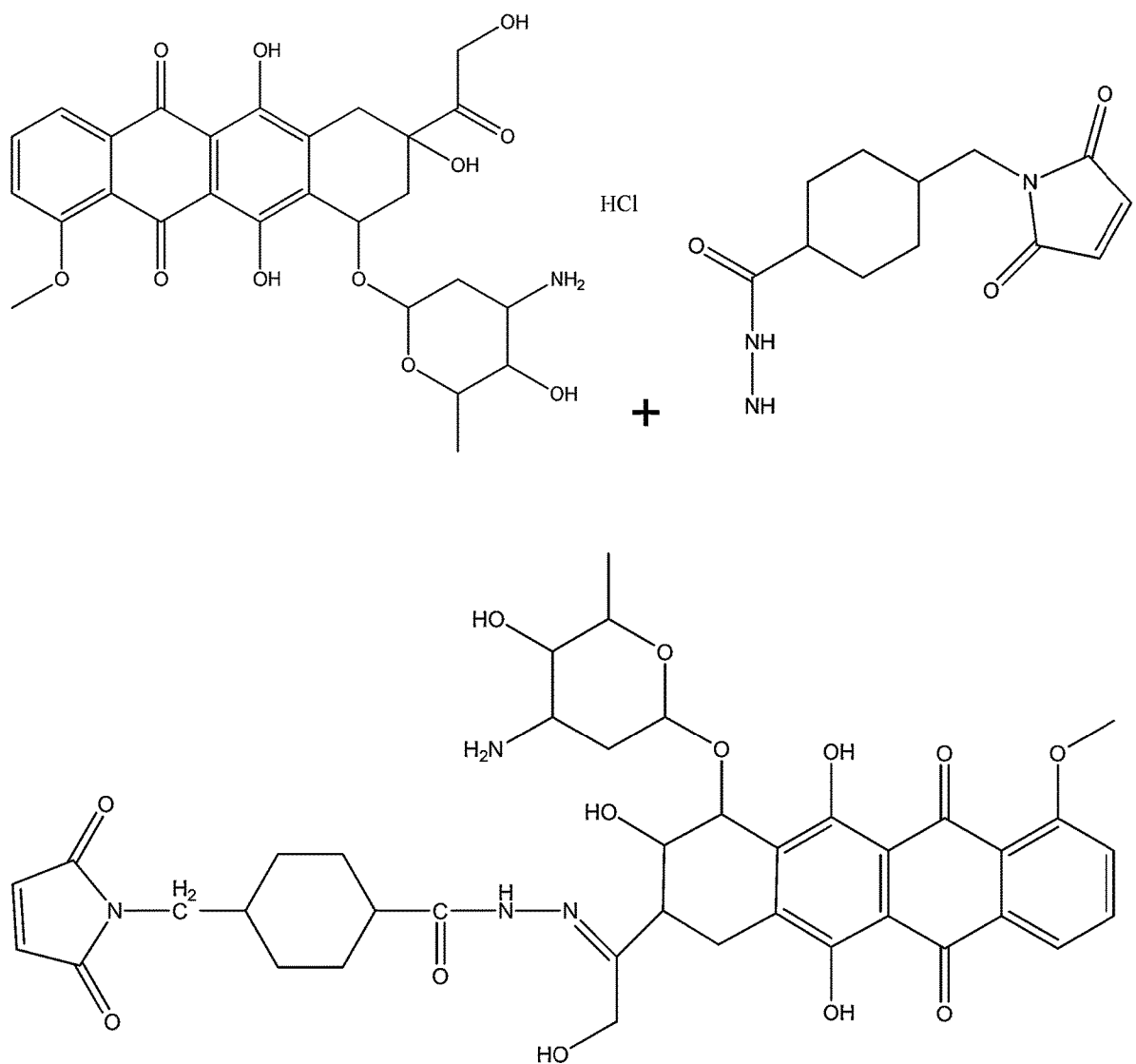
FIG. 8 illustrates the synthesis of MMCCH-Dox
Figure 9:
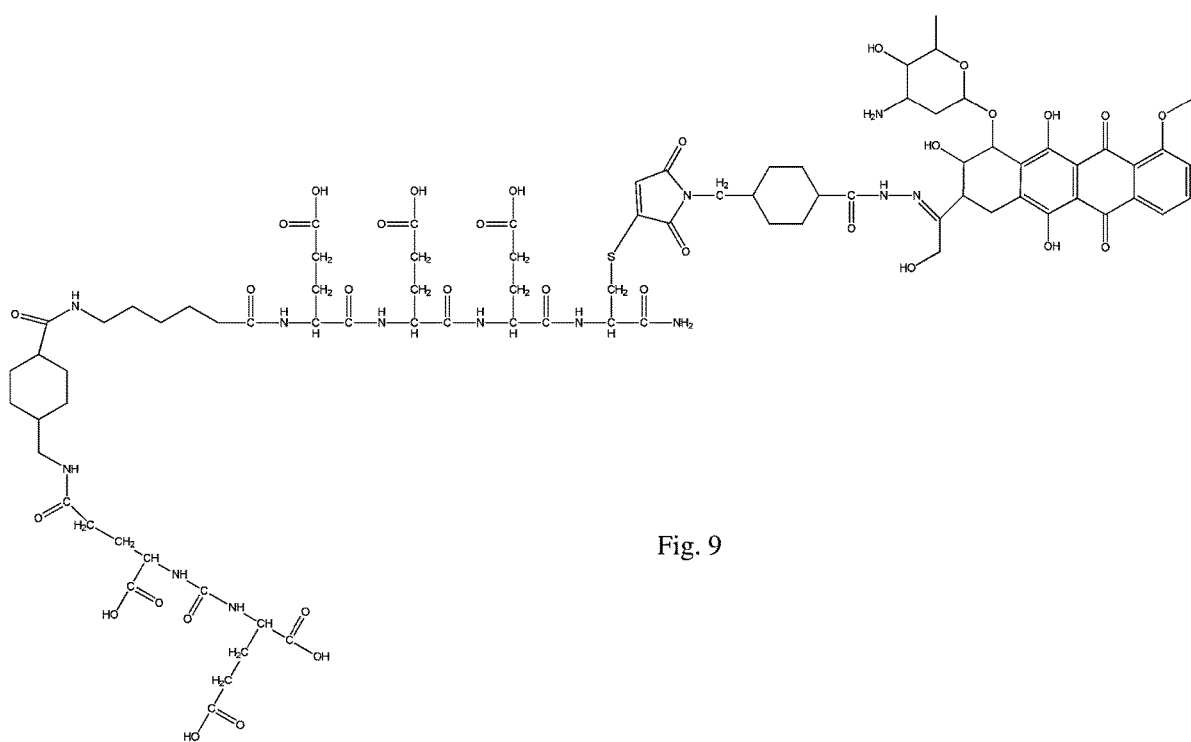
FIG. 9 illustrates synthesis of acid-labile PSMA-1-MMCCH-Dox.

The final conjugate, acid-labile PSMA-1-MMCCH-Dox, was produced by first generating MMCCH-Dox. This is another maleimide-functionalized doxorubicin, but with a hydrazone bond at the carbonyl group of doxorubicin rather than an NHS ester to amine reaction. Electrospray MS shows a peak at the expected molecular weight of 777 and a strong peak at 799, consistent with MW+Na. There are also peaks at 1553.3 consistent with a dimer and 1575.4 consistent with the dimer+Na. As above, the —SH in the PSMA ligand joins the maleimide in the MMCCH linker to produce the final product. See FIGS. 8 and 9.

Figure 10:
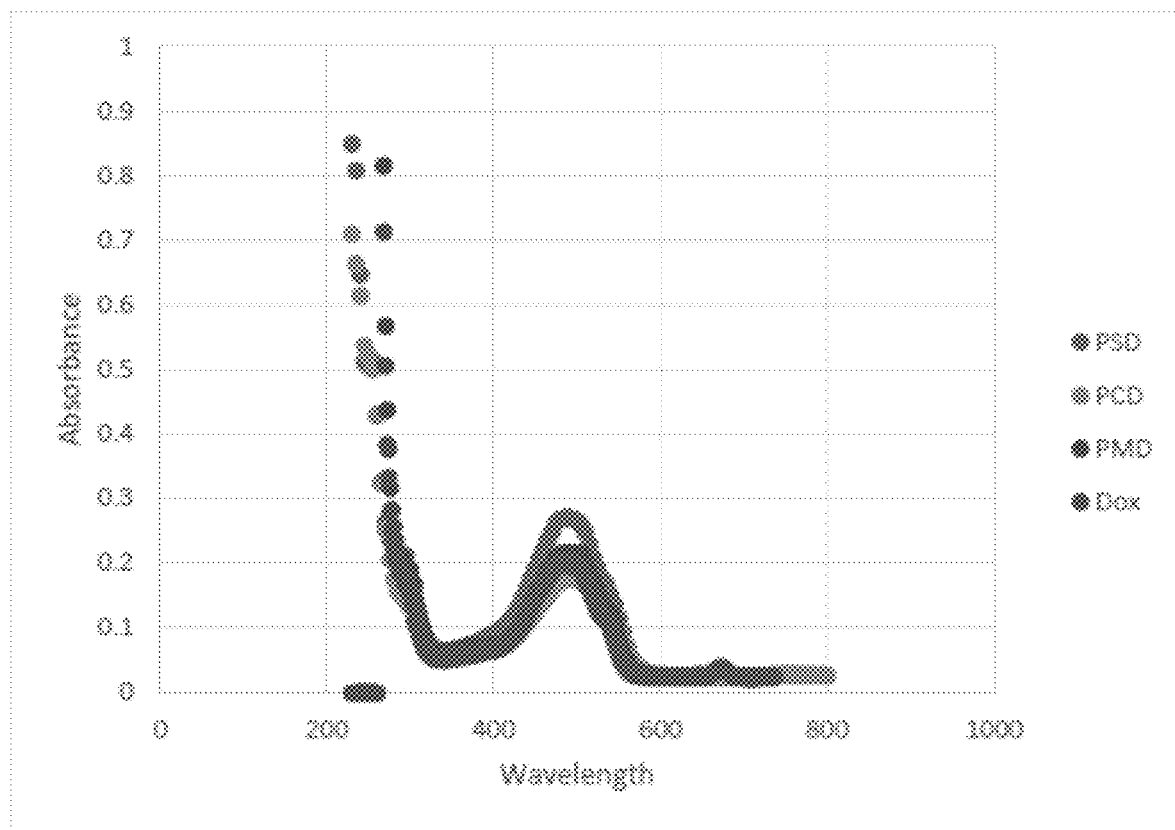
FIG. 10 illustrates absorption spectra of free doxorubicin and PSMA-Targeted conjugates. Note, absorption spectra was measured from stock dilutions and concentration is not uniform. While the absorbance values are not identical for this reason, the shape of the curve and peak absorption wavelength remains unchanged by conjugation to PSMA-1 (Cys). For brevity, PSMA-1-SMCC-Dox is labeled PSD, PSMA-1-MC-Val-Cit-PABC-Dox is labeled PCD, and PSMA-1-MMCCH-Dox is labeled PMD in this figure.

Conjugation of the PSMA-targeting ligand to doxorubicin via the three linkers tested did not influence the absorption spectra of doxorubicin. Peak absorption was seen at 480 nm for free doxorubicin and each conjugate, as demonstrated in FIG. 10.

In Vitro Cellular Uptake Studies

To determine whether the PSMA-1-Doxorubicin conjugates might be preferentially uptaken by PSMA-expressing PC3Pip cells compared to PSMA-negative PC3Flu cells, both of these cell lines were treated with 1 µM of doxorubicin or PSMA-1-Doxorubicin conjugate for either 90 minutes or 48 hours. Doxorubicin fluoresces and can therefore be visualized in cells by fluorescent microscopy. Free doxorubicin was equally seen in PC3Pip and PC3Flu cell lines, and the drug was seen primarily in the nucleus, overlying the DAPI nuclear staining in these cells. PSMA-1-SMCC-Dox demonstrated more signal in PC3Pip compared to PC3Flu cells, and as was the case with all PSMA-conjugates, the selectivity was more obvious at short cell treatment times. However, unlike free doxorubicin, the signal was seen in a spotty, endosomal type pattern. The same observations were true of PSMA-1-Val-Cit-PABC-Dox. PSMA-1-MMCCH-Dox showed similar selectivity for PC3Pip cells, but the doxorubicin signal did colocalize with the DAPI nuclear staining for this conjugate.

In Vitro Cytotoxicity

To determine whether our PSMA-1-Doxorubicin conjugates demonstrated any cytotoxic effect in vitro, and whether they may be more toxic to PSMA-expressing cells, the commercially available Dojindo CCK8 assay was used to monitor cell viability after treatment with free and PSMA-targeted doxorubicin. First, PC3Pip and PC3Flu cells were treated continuously for 48 hours with free doxorubicin, non-cleavable PSMA-1-SMCC-Dox, cathepsin-cleavable PSMA-1-MC-Val-Cit-PABC-Dox, and acid-labile PSMA-1-MMCCH-Dox. Doxorubicin exhibited potent, equal growth inhibition of PC3Pip and PC3Flu cell lines. PSMA-1-SMCC-Dox and PSMA-1-MC-Val-Cit-PABC-Dox showed essentially no growth inhibition of either cell line. PSMA-1-MMCCH-Dox, however, was significantly more toxic to PC3Pip cells compared to PC3Flu cells at all doses tested over the range 62.5-2000 nM.

The fluorescence microscopy data indicated that some PSMA-1-MMCCH-Dox does enter PC3Flu cells after long incubation periods, so the cytotoxicity assay was also repeated for free doxorubicin and the acid-labile conjugate at a slightly shorter incubation period of 24 hours in an attempt to optimize the cytotoxicity difference in the two cell lines. The cells were then provided fresh media and allowed to continue in culture for an additional 48 hours to allow for sufficient time for growth inhibition and/or cell death. The increased toxicity to PC3Pip cells compared to PC3Flu cells was again evident, at about the same magnitude, for these conditions. The drug conjugate, in vitro, was generally less toxic than free drug, especially at lower doses, which shows ratios of PSMA-1-MMCCH-Dox toxicity to free doxorubicin viability. At doses of 500 nM or more, the PSMA-1-MMCCH-Dox conjugate showed equal or superior cytotoxicity compared to free drug for PC3Pip cells, and at 1000 nM or more the targeted drug was also toxic to PC3Flu cells similarly to free doxorubicin.

Mouse Tumor Xenograft Response

Mice implanted with PSMA(+) PC3Pip flank tumors were treated with three weekly doses of 2 mg/kg of free doxorubicin, or the molar equivalent of PSMA-1-MMCC-Dox, 6.35 mg/kg. Tumor size was monitored with calipers, and toxicity was measured by mouse weight over time. Measurements were taken two times per week, day 0, 4, 7, 11, etc. until day 21. At these tested doses, all tumors grew in size with time. The mice treated with free doxorubicin exhibited more rapid tumor growth than those treated with PSMA-1-MMCCH-Dox, with growth difference reaching statistical significance through day 14 and trending toward significance through the end of the study. Additionally, mice treated with the targeted drug exhibited less weight loss, an indication of drug toxicity, over the duration of the study (1.8% vs. 17.3%, p=0.009).

In conclusion, three PSMA-1-Doxorubicin conjugates were synthesized making use of differing linker chemistries. All three were selective for PSMA(+) cell lines, but only acid-labile PSMA-1-MMCCH-Dox promoted release of free doxorubicin, allowing the drug to travel to the nucleus and exert its cytotoxic activity. This drug was tested in a flank tumor prostate cancer model, and resulted in tumor growth inhibition compared to free doxorubicin. Further, it was less toxic to the mice than free doxorubicin as determined by decreased weight loss while on treatment. It is anticipated that these agents may prove more effective while reducing significant toxicities/side effects compared with free doxorubicin for treatment of metastatic prostate cancer models in nude mice and later for treatment of human patients with prostate cancer or other PSMA-expressing tumors.

Example 2

In this Example, we used our PSMA ligand to selectively deliver the very potent microtubule disruption drug, monomethyl auristatin E (MMAE), to prostate cancer cells. Advantageously, using the PSMA ligand to selectively target a chemotherapeutic drug to PSMA was found to improve pharmacokinetics and enable more precise chemotherapy with lower side-effects. Using a prodrug strategy we developed a therapeutic small molecule, PSMA-1-VcMMAE, and a theranostic molecule, PSMA-1-VcMMAE-Cy5.5, in which the near-infrared dye Cy5.5 was incorporated in the structure to allow modification of pharmacokinetics and to follow tumor response to the treatment in mouse models. In heterotopic, orthotopic, and metastatic prostate cancer models in mice we found that both conjugates selectively and effectively inhibited PSMA-expressing tumor growth and prolonged animal survival with no obvious toxicity. PSMA-1-VcMMAE also had a much more favorable therapeutic index than either PSMA-1-VcMMAE-Cy5.5 or PSMA-ADC.

Materials and Methods

General

PSMA targeting peptide Glu-CO-Glu'-Amc-Ahx-Glu-Glu-Glu-Cys-C6-Lys (PSMA-1-Cys-C6-Lys) was synthesized by Fmoc chemistry. (S)-2-(3-((S)-5-amino-1-carboxypentyl)ureido)pentanedioic acid (Cys-CO-Glu) was custom made by Bachem Bioscience Inc. All the other chemicals were purchased from Sigma-Aldrich Inc. HPLC was performed on a Shimadzu HPLC system equipped with a SPD-20A prominence UV/visible detector and monitored at 220 nm and 254 nm. Preparative HPLC was achieved using Luna 5 m C18(2) 100A column (250 mm×10 mm×5 mm; Phenomenex) at a flow rate of 2.5 mL/min. Analytical HPLC was performed using an analytical Luna 5 m C18(2) 100A column (250 mm×4.6 mm 5 mm; Phenomenex) at a flow rate of 0.8 mL/min. The gradient used was 10% to 90% acetonitrile against 0.1% trifluoroacetic acid over 30 minutes.

Synthesis of PSMA-1-VcMMAE

PSMA-1-VcMMAE was synthesized as a prodrug by conjugating MMAE to the Cys residue in PSMA-1-Cys-C6-Lys via a maleimido caproyl valine-citruline (Vc) cathepsin-cleavable linker with a self immolative p-aminobenzyl carbamate (PABC) spacer. PSMA-1-Cys-C6-Lys (2.6 mg, 2 μmol) was dissolved in 500 μL of phosphate buffer; then 2.2 μmol of Vc-MMAE (3.0 mg) (BOC Sci.) in 500 μL of DMF was added. The pH of the reaction mixture was adjusted to 8 by triethylamine. The mixture was stirred at room temperature for 1 hour, then went through HPLC to get purified PSMA-1-VcMMAE. Yield: 4.4 mg (85%). Retention time: 16.8 min. MS ($C_{123}H_{195}N_{23}O_{37}S$), calculated: 2618.3; found: 1310.7 ([M+2H]/2), 874.1 ([M+3H]/3).

Synthesis of PSMA-1-VcMMAE-Cy5.5

PSMA-1-Cys-C6-Lys (2.6 mg, 2 μmol) was dissolved in 500 μL of phosphate buffer; then 2.2 μmol of Vc-MMAE (3.0 mg) (BOC Sci.) in 500 μL of DMF was added. The pH of the reaction mixture was adjusted to 8 by trimethylamine. After stirring at room temperature for 1 hour, Cy5.5 NHS ester 2.5 μmol in 200 μL of DMF was added. The reaction mixture was stirred overnight, then the product was purified by semi-preparative HPLC. Yield: 3.1 mg (50%). Retention time: 18.8 min. MS ($C_{163}H_{236}N_{25}O_{38}S$), calculated: 3185.8; found: 1062.2 ([M+$^3$H]/3), 796.9 ([M+4H]/4).

Synthesis of PSMA-1-McMMAE-Cy5.5

PSMA-1-McMMAE-Cy5.5 was synthesized using a non-cleavable maleimido caproyl (Mc) linker. It was synthesized in the same way as PMA-1-MMAE-Cy5.5. Yield: 45%. Retention time: 20.9 min. MS ($C_{144}H_{209}N_{20}O_{33}S$), calculated: 2780.4; found: 1041.2 ([M+H+Na]/2), 942.2 ([M+H+2Na]/3).

Cell Culture

Retrovirally transfected PSMA positive PC3pip cells and transfection control PC3flu cells were obtained from Dr. Michel Sadelain in 2000 (Laboratory of Gene Transfer and Gene Expression, Gene Transfer and Somatic Cell Engineering Facility, Memorial-Sloan Kettering Cancer Center, New York, NY). C4-2 cells were from ATCC. The cells were last sorted and checked by western blot in 2019; no genetic authentication was performed. Cells were maintained in RPMI1640 medium (Invitrogen) with 2 mM L-glutamine and 10% Fetal Bovine Serum at 37° C. and 5% $CO_2$ under a humidified atmosphere.

Competitive Binding Assay

The assay was carried as previously reported by incubation PC3pip cells with different concentrations of drug conjugates in the presence of 10 nM N—[N—[(S)-1,3-dicarboxypropyl]carbamoyl]-S-[$^3$H]-methyl-L-cysteine ($^3$H-ZJ24) (GE Healthcare Life Sciences, Pittsburgh, PA). Radioactivity of cell pellet was counted by scintillation counter. The concentration required to inhibit 50% of binding was determined (IC$_{50}$) by GraphPad Prism 3.0.

Enzymatic Cleavage of PSMA-1-MMAE-Cy5.5 by Cathepsin B

PSMA-1-VcMMAE-Cy5.5 or PSMA-1-McMMAE-Cy5.5 was added to 500 µL of activated human liver cathepsin B (Anthens Research and Technology) solution (46) to a final concentration of 2 µM and incubated at 37° C. At different time intervals, 40 µL of the solution was taken out into tubes loaded with 1 µL of 1 mM E64 protease inhibitor. The mixture was vortexed and then stored at −80° C. for future HPLC analysis to assess degradation of PSMA-1-VcMMAE-Cy5.5 or PSMA-1-McMMAE-Cy5.5. Studies were performed in triplicate.

In Vitro Cytotoxicity Assay

Cells (1,000/well) were seeded in 96-well culture plates the day before treatment. Cells were incubated with various concentrations of drugs for 72 hours and cell viability evaluated by CCK-8 (Dojindo). The concentration required to reach 50% of cell proliferation was determined (IC$_{50}$) by GraphPad Prism 3.0.

In Vitro Cellular Uptake Studies

PC3pip and PC3flu cells were seeded in µ-Slide 8-Well Chamber Slide (ibidi GmbH) at 2,000 cells/well. When cells grew to 70% confluency, PSMA-1-VcMMAE-Cy5.5 or PSMA-1-McMMAE-Cy5.5 conjugations were added at 50 nM and incubated at 37° C. for 4 hours. Cells were washed with PBS and stained with DAPI and LysoOrange (Abcam) for 30 minutes at 370 and 5% CO$_2$, after which they were washed again with PBS and filled with fresh medium. Selectivity was determined by including 20-fold excess of the PSMA-1 ligand. The uptake and localization of the drug conjugates were visualized under a Leica HyVolution SP8 confocal microscope at 40×.

Immunofluorescence Analysis of Alpha-Tubulin

Cells on coverslips at about 70% confluency were incubated with 5 nM of MMAE, PSMA-1-VcMMAE-Cy5.5 or PSMA-1-McMMAE-Cy5.5 for 24 hours. Cells were washed and fixed with 4% paraformaldehyde for 10 minutes, permeabilized with 0.1% Triton™ X-100 for 10 minutes, and blocked with 1% BSA for 1 hour at room temperature. Alpha-tubulin (B5-1-2) Alexa Fluor 488 Mouse Monoclonal Antibody (Invitrogen) was then added at 2 µg/mL in 0.1% BSA and incubated for 3 hours at room temperature. Cells were counterstained with DAPI, mounted with Fluor-Mount aqueous mounting solution, and observed under Leica DM4000B fluorescence microscopy at 40×.

In Vivo NIR Imaging Studies

Under guidelines of the animal care and use committee at Case Western Reserve University (IACUC #150033) 6 to 8-week old male Balb/cathymic nude mice were implanted subcutaneously with 1×10$^6$ of PC3flu and PC3pip on the left and right dorsum respectively. Mice received 40 nmol/kg of PSMA-1-VcMMAE-Cy5.5 or PSMA-1-McMMAE-Cy5.5 in PBS via tail vein injection when tumors reached 10 mm in diameter. Fluorescence imaging was performed using the Maestro In Vivo Imaging system (Perkin-Elmer). Multispectral images were unmixed into their component spectra (PSMA probes, autofluorescence, and background) to quantitate the average fluorescence intensity associated with the tumors using regions of interest (ROIs) around the tumors.

Maximum Tolerated Dose (MTD)

Groups of three male mice received single injections of MMAE, PSMA-1-Vc-MMAE, PSMA-1-VcMMAE-Cy5.5 or PSMA-ADC via the tail vein to determine single-dose MTD. Mice were monitored daily for 14 days. The MTD was defined as the highest dose that did not cause serious overt toxicities or 20% weight loss in any of the animals.

Heterotopic Survival Study

Male athymic nude mice were implanted subcutaneously with 1×10$^6$ of PC3pip cells under the right dorsum of the mice. When tumor size reached approximately 100 mm$^3$ (tumor volume=Length×width$^2$/2), mice received drugs through tail vein injection. Mice were treated every four days with a total of five doses. Animals were weighed and tumor size measured every other day for 90 days. Cures were defined as no tumor present at end of the 90-day study. When tumors became too large or animals were moribund they were euthanized. Five mice were used in each group.

Orthotopic Survival Study

Surgical orthotopic tumor implantation was performed as previously reported. Tumor growth/size was monitored using Siemens Acuson S2000 ultrasound scanner. When the tumors were at the appropriate size (5 mm as measured by ultrasound, approximately 2 weeks) animals were given PSMA-1-VcMMAE, PSMA-1-VcMMAE-Cy5.5, or PBS every four days with a total of 5 doses. Tumors were monitored every other day by ultrasound. Each group had five mice.

Metastatic Survival Study

Male athymic nude mice were injected into the left ventricle of the heart with 1×10$^5$ GFP labeled PC3pip cells to generate bone metastasis. One week later mice received 160 nmol/kg PSMA-1-VcMMAE-Cy5.5 or PBS every 4 days with a total of 5 doses and the progression of disease was monitored by GFP imaging. Five mice were used in each group. Statistics Student t-test was used to compare inter-group differences. Kaplan-Meier survival data were analyzed by SAS9.4 using log-rank tests. A p value <0.05 was considered statistically significant for all comparisons.

Results

A Prodrug Strategy is Crucial for Antitumor Activity

Figure 11A:
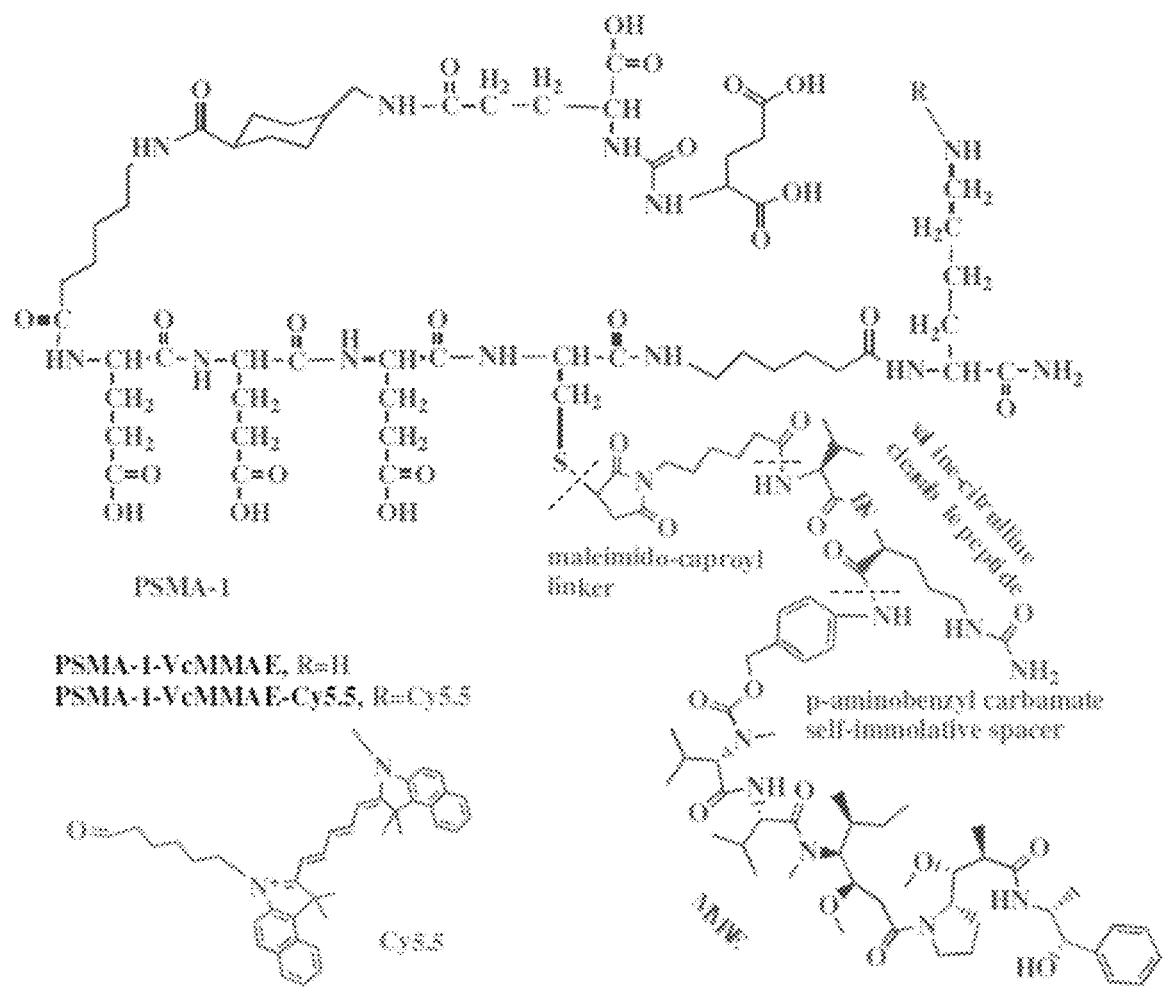
FIGS. 11(A-E) illustrate a schematic and plots showing novel PSMA-targeted drug conjugates. (A) Structure of PSMA-1-VcMMAE-Cy5.5 which has a cleavable linker. (B) Structure of PSMA-1-McMMAE-Cy5.5 which has a non-cleavable linker. (C) In vitro competition binding results of PSMA-targeted drug conjugates. Values are mean±SD of triplicates. PSMA-1-VcMMAE-Cy5.5 and PSMA-1-McMMAE-Cy5.5 showed similar binding affinity. (D) In vitro cathepsin cleavage of PSMA-targeted drug conjugates. Both conjugates were stable in PBS. In the presence of cathepsin, PSMA-1-VcMMAE-Cy5.5 decomposed rapidly, while PSMA-1-McMMAE-Cy5.5 remained stable. Values are mean±SD of triplicates. (E) In vitro cytotoxicity of PSMA-targeted drug conjugates to PSMA-positive PC3pip cells (solid lines) and PSMA negative PC3flu cells (dashed lines) after 72-hour incubation. PSMA-1-VcMMAE-Cy5.5 was much more potent than PSMA-1-McMMAE in killing PC3pip cells. Presence of cathepsin B inhibitor E64 reduced the activity of PSMA-1-VcMMAE-Cy5.5, suggesting the conjugate functioned as prodrug. Values are mean±SD of 6 replicates.

We initially synthesized two PSMA-targeted MMAE-Cy5.5 conjugates, one with a cathepsin-cleavable linker, PSMA-1-VcMMAE-Cy5.5, and the other with a non-cleavable linker, PSMA-1-McMMAE-Cy5.5, (FIGS. 11A-B) and characterized the antitumor activity of the small molecule-drug conjugates.

Figure 11B:
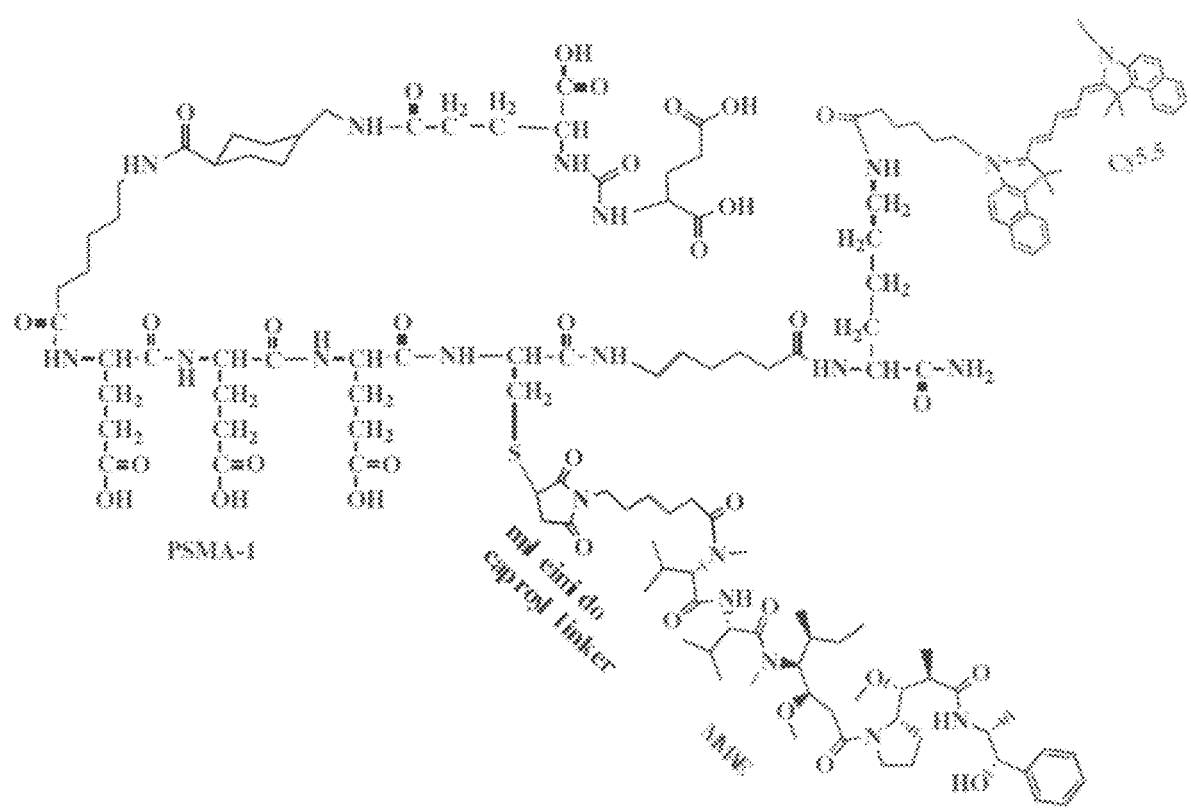
Figure 11C:
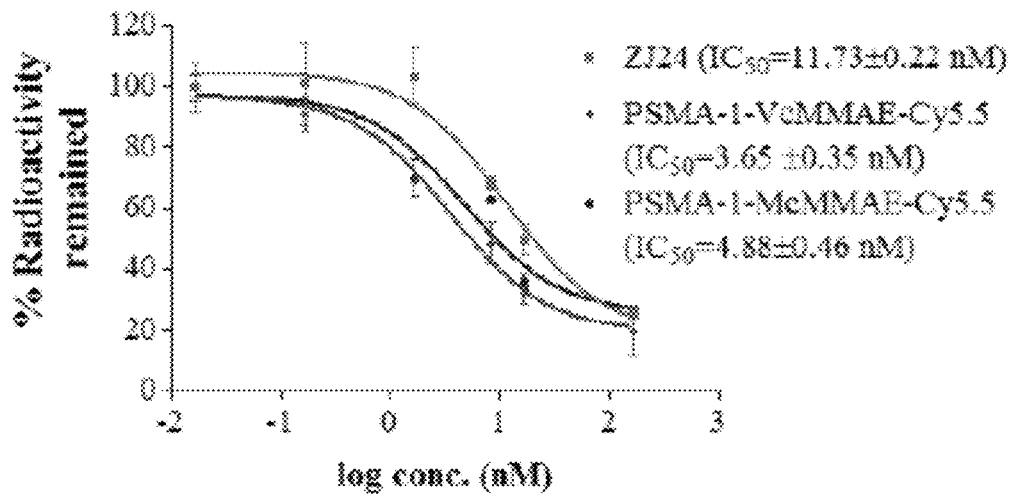

Competition binding experiments demonstrated that the complexity of the drug conjugates did not impact their binding affinity to PSMA; PSMA-1-VcMMAE-Cy5.5 showed an IC$_{50}$ of 3.65 nM and PSMA-1-McMMAE-Cy5.5 had an IC$_{50}$ of 4.88 nM, both similar to unconjugated PSMA-1, IC$_{50}$=2.30 nM and significantly lower than the parent ZJ24 ligand, IC$_{50}$=11.73 nM (FIG. 11C).

Figure 11D:
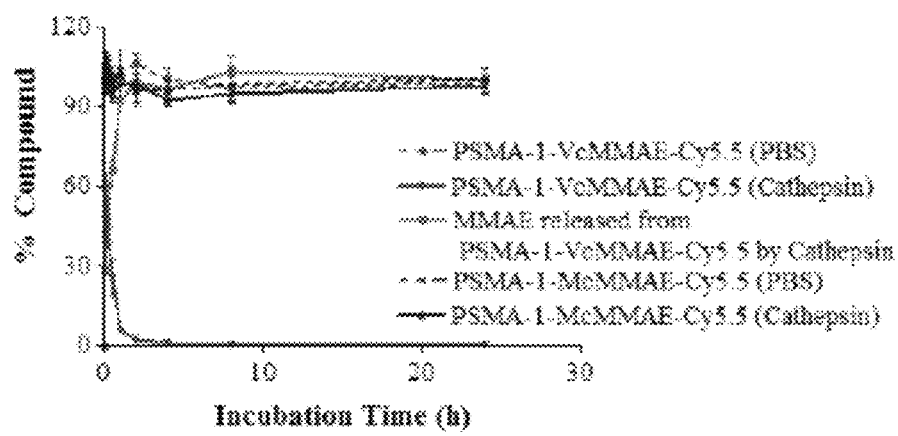

To investigate if PSMA-targeted drug conjugates were cleavable by cathepsin B, the two conjugates were incubated with or without the enzyme and chromatographed by HPLC. When the conjugates were incubated with PBS, both PSMA-1-VcMMAE-Cy5.5 and PSMA-1-McMMAE-Cy5.5 were stable (FIG. 11D). In the presence of cathepsin B, PSMA-1-VcMMAE-Cy5.5 degraded rapidly with a half-life at 0.33 h, releasing intact MMAE, while PSMA-1-McMMAE-Cy5.5 remained intact (FIG. 11D). The results demonstrated that PSMA-1-VcMMAE-Cy5.5 can be cleaved by cathepsin B, while PSMA-1-McMMAE-Cy5.5 is not cleavable by the protease.

Figure 11E:
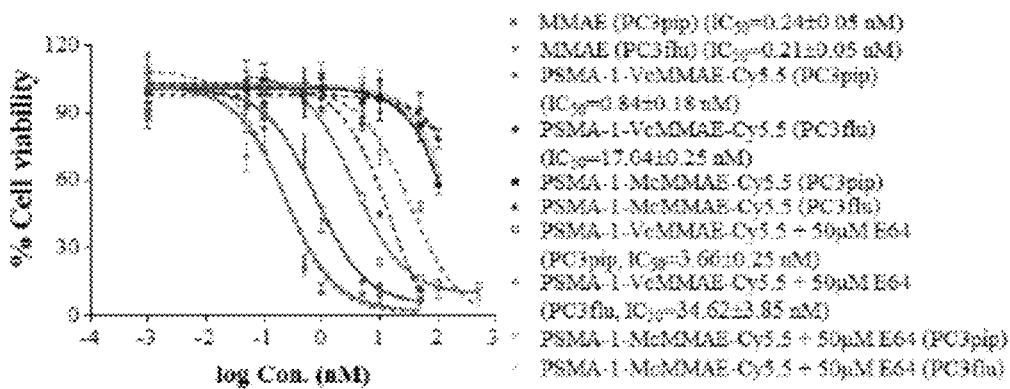

To test if PSMA-targeted drug conjugates could selectively kill PSMA-expressing cells, cytotoxicity studies were performed in both PSMA-positive PC3pip and PSMA-negative PC3flu cells. PSMA-1-VcMMAE-Cy5.5 was about 20-fold more potent at killing PSMA-positive PC3pip cells ($IC_{50}$=0.84 nM) than PSMA-negative PC3flu cells ($IC_{50}$=17.0 nM) (FIG. 11E), while the free drug MMAE showed no selectivity between PSMA positive and negative cells. In contrast, PSMA-1-McMMAE-Cy5.5 was much less potent in cell killing, no $IC_{50}$ values could be obtained for either PC3pip and PC3flu cells for the concentrations tested, suggesting PSMA-1-VcMMAE-Cy5.5 acts as a prodrug dependent on protease activation. To confirm protease dependent activation of PSMA-1-VcMMAE-Cy5.5, we performed in vitro cell killing studies including 50 µM of the protease inhibitor E64 (FIG. 11E). Co-incubation with 50 M of protease inhibitor E64 reduced the potency of PSMA-1-VcMMAE-Cy5.5, confirming that the conjugate worked as a prodrug.

Figure 12A:
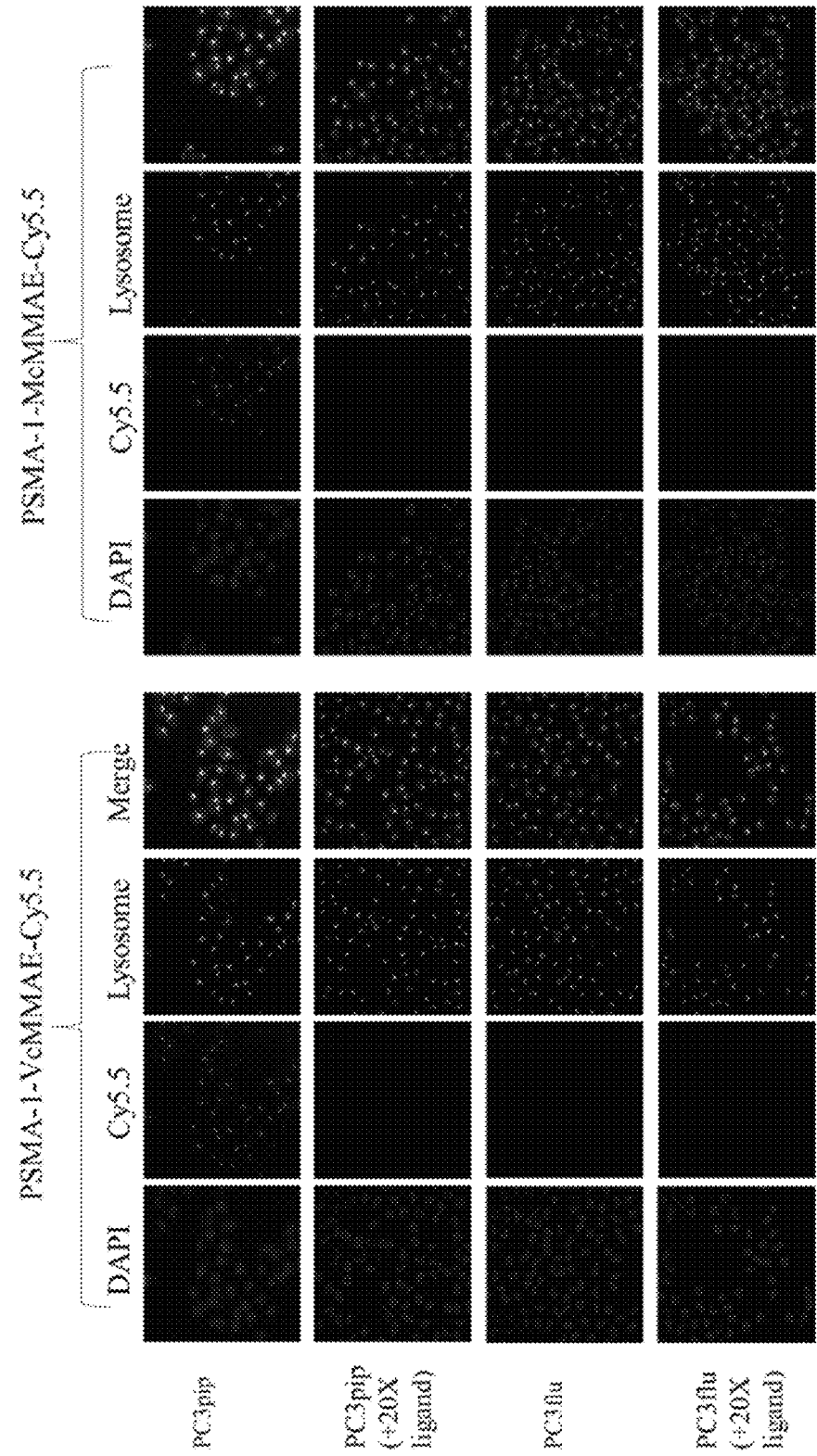
FIGS. 12(A-B) illustrate images showing in vitro fluorescence studies of PSMA-targeted drug conjugates. (A) In vitro cellular uptake results of PSMA-targeted drug conjugates. Cells were incubated with 50 nM of drug conjugates for 4 hour. Nuclei are false colored blue, lysosomes are false colored green and drug conjugates are false colored red. Selective uptake was observed only in PC3pip cells and the conjugates were mainly located in lysosomes. Specificity of drug conjugates for PSMA binding was evaluated by including 1 mM of unlabeled PSMA-1 ligand during incubations. Signal in PC3pip cells was significantly competed by PSMA-1, suggesting the binding is specific. Images are taken at 40×. Representative images are shown from three independent experiments. (B) Immuno-detection of α-tubulin. Cells were treated with 5 nM of drugs for 24 hours then fixed and immunofluorescence stained by Alex-488-labeled α-tubulin antibody. Selective disruption in PC3pip cells was only observed when cells were treated with PSMA-1-VcMMAE-Cy5.5. Images were taken at 40×. Representative images are shown from three independent experiments.

To determine if PSMA-targeted drug conjugates would result in selective cellular binding and uptake, in vitro uptake studies were performed. Similar levels of fluorescence uptake into PC3pip cells was observed after treatment with either PSMA-1-VcMMAE-Cy5.5 or PSMA-1-McMMAE-Cy5.5 and was localized to the lysosomal compartment of the cells (FIG. 12A). Competition studies indicated that binding of the two conjugates was selective and specific for the PSMA receptor expressed on the PC3pip cells.

Figure 12B:
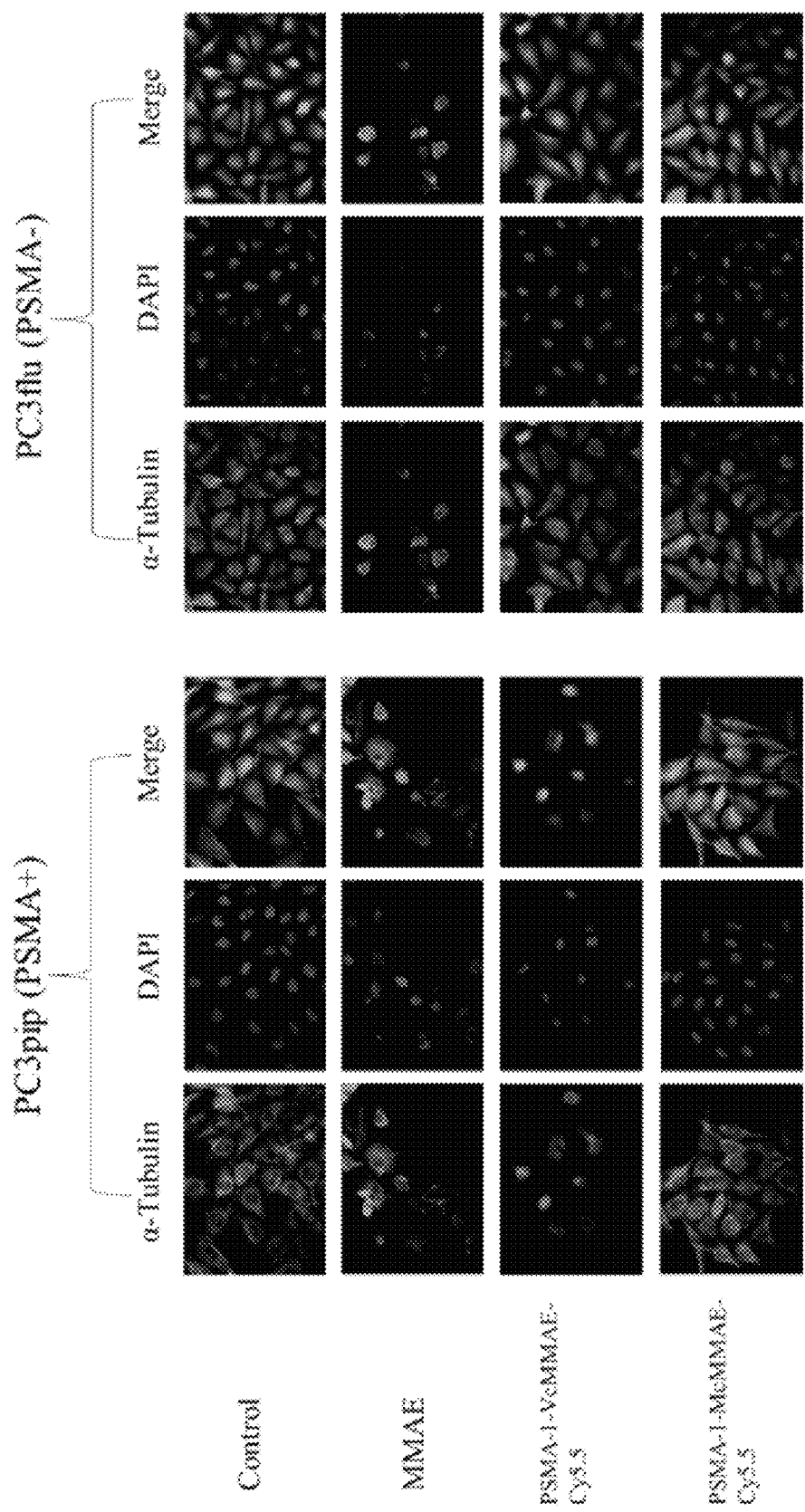

It is known that MMAE inhibits cell division by destabilization of α-tubulin. To further validate the biological consequence of MMAE-conjugate treatment, in vitro immunofluorescence staining of α-tubulin was performed (FIG. 12B). Incubation with free MMAE led to non-selective tubulin disruption of the microtubule network in both PC3pip and PC3flu cells, causing them to round up and lose the spindle structure. PSMA-1-VcMMAE-Cy5.5 showed selective disruption of tubulin in PC3pip cells but not in PC3flu cells. In contrast, no obvious disruption of tubulin was observed in PC3pip or PC3flu cells when treated with the same concentration of the non-cleavable PSMA-1-McMMAE-Cy5.5.

To demonstrate selective tumor uptake in vivo, mice bearing both PC3flu and PC3pip tumors were injected with 40 nmol/kg of PSMA-1-VcMMAE-Cy5.5 or PSMA-1-McMMAE-Cy5.5 and uptake monitored via fluorescence imaging over time (FIG. 13). Similar selective uptake was observed in PC3pip tumors for both conjugates, peaking at 24-hour post-injection followed by a prolonged clearance. At 24-h post-injection there was little to no detectable uptake in PSMA-negative PC3flu tumors (FIGS. 13A-B). Ex vivo imaging of tissues at 72-hour post-injection showed that fluorescence was mainly retained in the PSMA-expressing tumor; no/minimal fluorescence was detected in other organs (FIG. 13C).

Figure 13A:
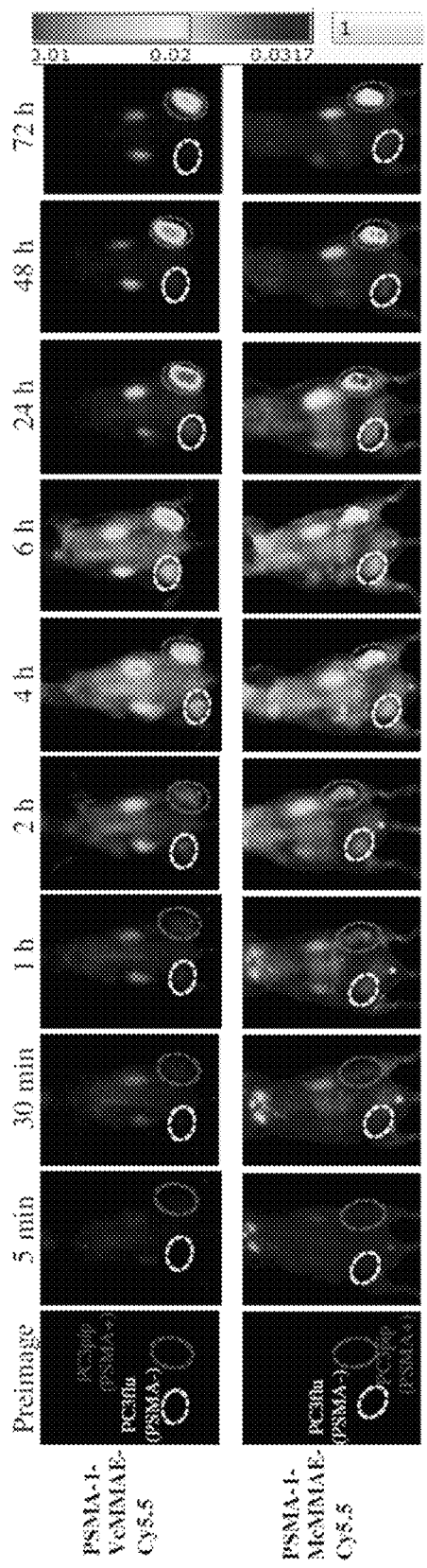
FIGS. 13(A-C) illustrate images and plots showing in vivo biodistribution and antitumor activity studies. (A) In vivo Maestro imaging of a typical mouse bearing heterotopic PC3pip and PC3flu tumors treated with 40 nmol/kg of drug conjugates through i.v. injection. Representative images are shown of n=5. Selective uptake was observed in PC3pip tumors. (B) Quantification of fluorescent signal intensity in PC3pip and PC3flu tumors. Values are mean±SD of 5 animals. (C) Ex vivo imaging of mouse organs at 72-hour post-injection. Fluorescent signal in PC3pip tumor was significantly higher than in other organs. Representative images are shown of n=5. (D) In vivo tumor inhibition of PSMA-targeted drug conjugates using heterotopic PC3pip tumors. Mice received 160 nmol/kg of either PSMA-1-VcMMAE-Cy5.5 or PSMA-1-McMMAE-Cy5.5 every 4 days with a total of 5 doses. Significant tumor regression was only observed in mice treated with PSMA-1-VcMMAE-Cy5.5. Values represent mean±SD of 5 animals. (*, PSMA-1-VcMMAE-Cy5.5 vs PBS, P<0.05; #, PSMA-1-VcMMAE-Cy5.5 vs PSMA-1-McMMAE-Cy5.5, P<0.05).
Figure 13B:
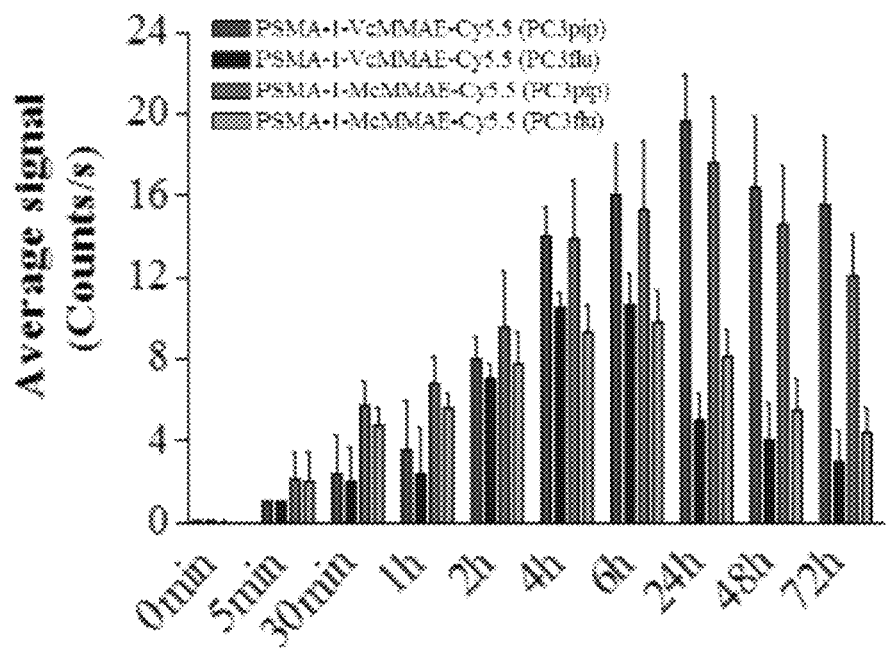
Figure 13C:
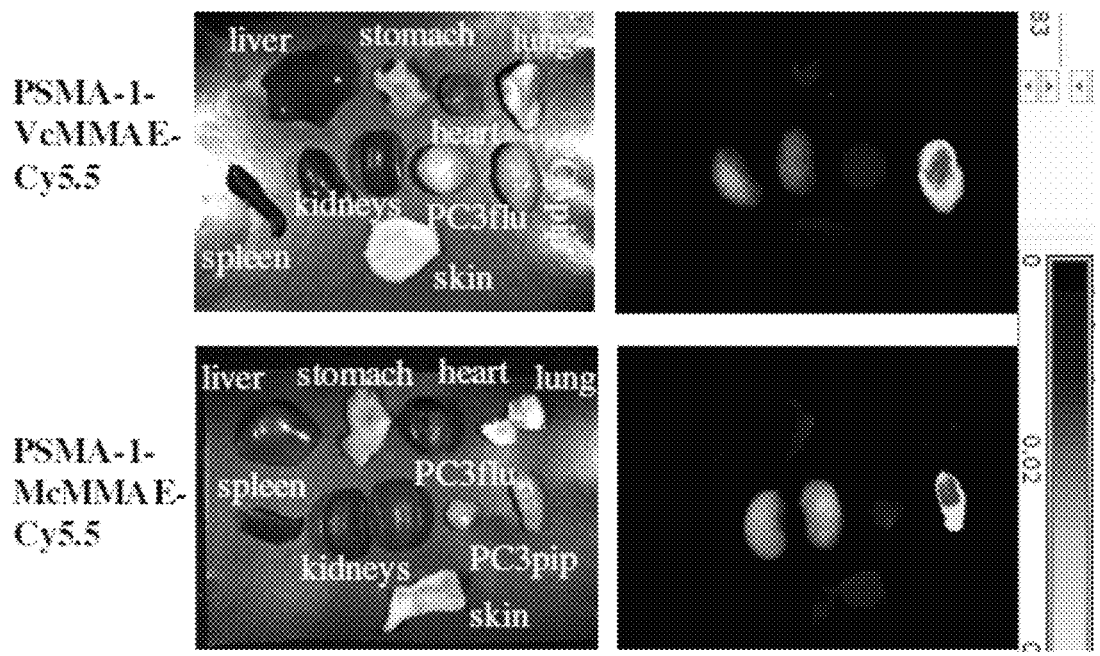
Figure 13D:
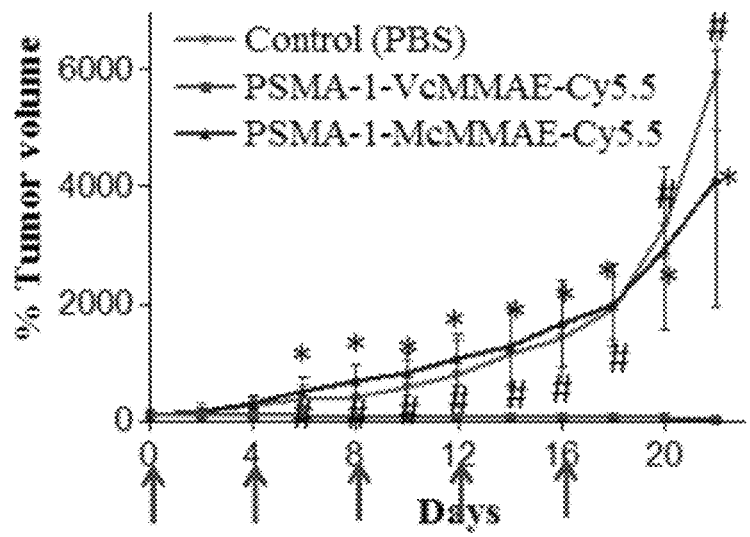

We next compared the antitumor activity of the two conjugates in mice bearing a flank PC3pip tumor. Each animal received 160 nmol/kg of PSMA-1-VcMMAE-Cy5.5 or PSMA-1-McMMAE-Cy5.5 through tail vein injection every four days with a total of 5 doses. (Dosing was based on previously published dose and schedules for antibody-drug conjugates). Mice were then imaged and tumors were measured by caliper. Untreated PC3pip tumor grew rapidly achieving a 50-fold increase in size by day 22 (FIG. 13D). Quantitative Maestro imaging showed that the average fluorescence signal in PC3pip tumors was similar for each theranostic injected and peaked in PC3pip tumors 24-hour after each injection (day 1, day 5, day 9, day 13 and day 17). Mice treated with the non-cleavable conjugate, PSMA-1-McMMAE-Cy5.5, showed similar growth rate as that measured for untreated mice. In contrast, administration of PSMA-1-VcMMAE-Cy5.5 effectively inhibited tumor growth as early as day 6 after the initial dose, indicating that prodrug strategy with cleavable linker is imperative for the antitumor activity of the conjugates. The changes in body weight were similar between mice receiving PBS or targeted drug conjugates, suggesting that the drug treatment is not very toxic to the animals.

Efficacy of PSMA-Targeted Prodrug Conjugates In Vitro

Figure 14A:
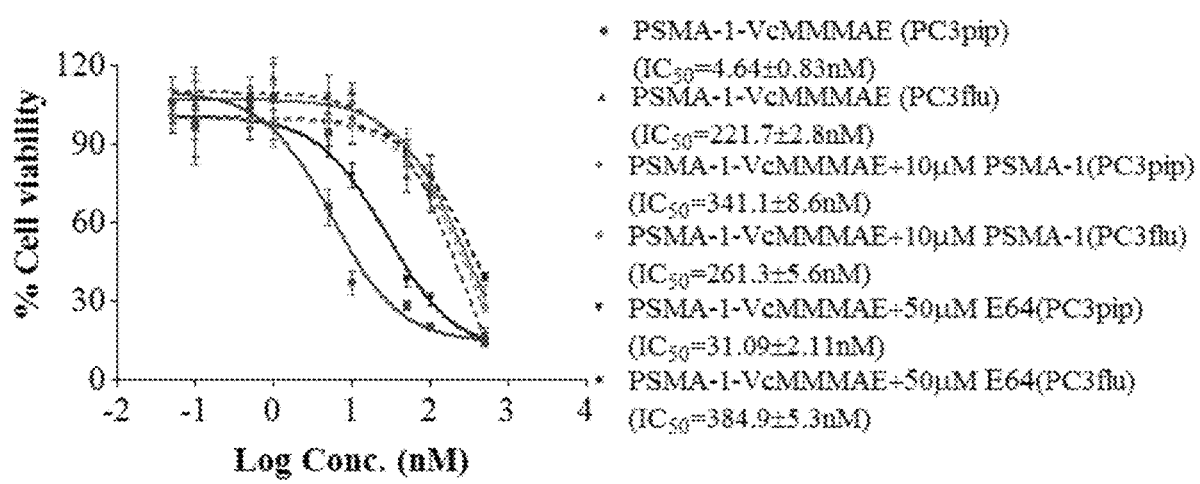
FIGS. 14(A-B) illustrate plots showing in vitro cytotoxicity studies of PSMA-1-VcMMAE (A) and PSMA-1-VcMMAE-Cy5.5. (B) Cells were incubated with various concentration of drugs for 72 hours, then cell viability was determined by CCK8 assay. Both conjugates showed the ability to selectively kill PC3pip cells. In the presence of 10 μM of PSMA-1 ligand, their potency to kill PC3pip cells was reduced to the same as PC3flu cells, indicating the killing is selective for PSMA expression. Presence of cathepsin B inhibitor E64 also reduced the activity of PSMA-1-VcMMAE, suggesting the conjugate functioned as prodrug. Values are mean±SD of 6 replicates.
Figure 14B:
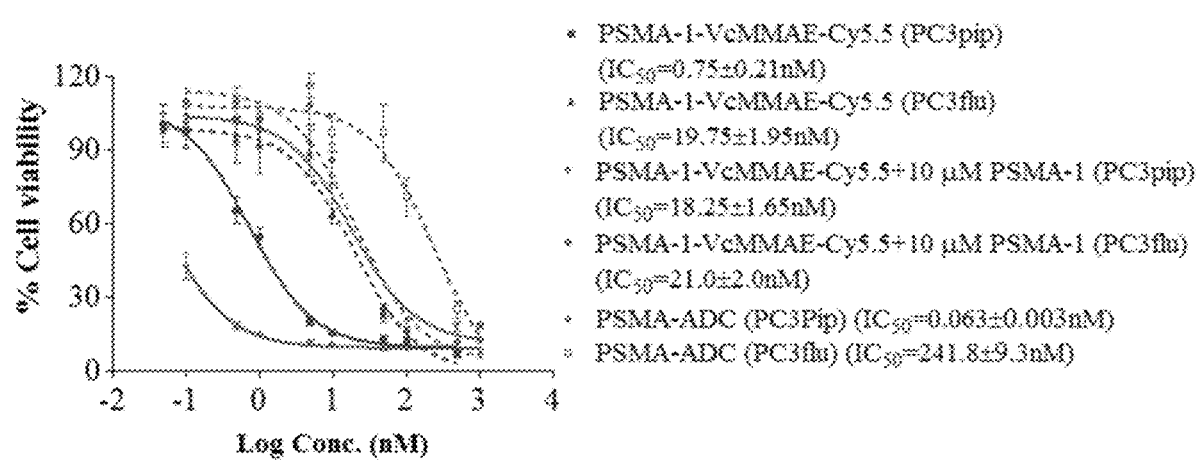

Having confirmed that prodrug strategy is crucial for the antitumor activity, we performed studies to further explore the antitumor activity of PSMA-1-VcMMAE and PSMA-1-VcMMAE-Cy5.5 (FIG. 11A) in vitro and in vivo (FIG. 14). The incorporation of Cy5.5 will not only provide information of tumor response to the treatment, but, we have demonstrated, will also modulate blood retention. Both PSMA-1-VcMMAE (FIG. 14A) and PSMA-1-VcMMAE-Cy5.5 (FIG. 14B) selectively killed PC3pip cells with $IC_{50}$'s of 4.64 and 0.75 nM, respectively. Removal of the Cy5.5 moiety, however, increased the $IC_{50}$ of PSMA-1-VcMMAE by 6.2-fold against PC3pip cells and 11.1-fold against PC3flu cells, suggesting a reduction in absolute efficacy. For PSMA-1-VcMMAE the ratio of $IC_{50}$'s between PC3pip and PC3flu cells increased to 48.2, compared to a ratio of 26.3 for PSMA-1-VcMMAE-Cy5.5, suggesting that removal of Cy5.5 increased the selectivity of the probe for PSMA-expressing cells. In the presence of 10 µM of PSMA-1, the potency to kill PC3pip cells for both agents was reduced to the same potency to kill PC3flu cells, again indicating that the killing is dependent on PSMA binding. PSMA-1-VcMMAE activity was also susceptible to E64 protease inhibition suggesting that it also worked as a prodrug, FIG. 14A. We next compared the cytotoxicity of these agents with antibody-conjugated MMAE (PSMA-ADC), which entered clinical trials but failed due to toxicity. It was found that PSMA-ADC was the most potent ($IC_{50}$=0.063 nM), followed by PSMA-1-VcMMAE-Cy5.5 ($IC_{50}$=0.75 nM), and PSMA-1-VcMMAE ($IC_{50}$=4.64 nM). PSMA-ADC had better selectivity defined by differential cytotoxicity ratio between PC3pip and PC3flu cells of 3838-fold compared to PSMA-1-VcMMAE (48-fold) and PSMA-1-VcMMAE-Cy5.5 (26-fold). PSMA-ADC ($IC_{50}$=241.8 nM) and PSMA-1-VcMMAE ($IC_{50}$=221.7 nM) had similar potency to kill non-PSMA expressing PC3flu cells, suggesting the antibody's greater affinity resulted in efficacy differences against PC3pip cells.

In Vivo Studies of Toxicity and Efficacy

The maximum tolerated dose (MTD) was determined in tumor-free athymic nude mice to determine the toxicity of the conjugates. Loss of 20% body weight or any overt signs of toxicity was used as an end point. We compared the MTD of free drug MMAE, PSMA-targeted drug conjugates and PSMA-ADC. MTDs of single dose i.v. injection of MMAE, PSMA-1-VcMMAE, PSMA-1-VcMMAE-Cy5.5 and PSMA-ADC were 700 nmol/kg, 7640 nmol/kg, 480 nmol/kg and 640 nmol/kg, respectively, highlighting the superior safety (10-fold or greater) of PSMA-1-VcMMAE compared to all the other drug derivatives.

For in vivo antitumor activity, we first studied in vivo potency of PSMA-1-VcMMAE in nude mice bearing heterotopic PC3pip tumors. Mice received drugs intravenously every 4 days with a total of 5 doses. In PBS control groups the tumor grew rapidly resulting in animal death within 30 days. In contrast treatment with PSMA-1-VcMMAE showed the ability to inhibit tumor growth and prolong animal survival in a dose dependent manner. At the highest dose tested (3820 nmol/kg, ½ of its MDT), all 5 mice survived the 90-day experimental time and 3 out of 5 mice were tumor free resulting in 60% cure. No body weight loss was observed even at the highest dose tested. It was also found that PSMA-1-VcMMAE was significantly more effective at inhibiting PSMA-positive PC3pip tumor growth than PSMA-negative PC3flu tumor growth when used at a lower dose of 955 nmol/kg (P=0.0493). We then administered PSMA-1-VcMMAE in mice bearing orthotopic PC3pip tumors, which mimic human prostate cancer in a more realistic way. Inhibition of tumor growth and extension of animal survival time were observed in the orthotopic PC3pip tumor models, and significant differences were observed at the dose of 1910 (P=0.0449) and 3860 nmol/kg (P=0.0019) when compared to the PBS control, with 1 mouse that was tumor free at the dose of 3860 nmol/kg. Initial changes in body weight were similar among the tested groups.

We have reported that Cy5.5 can change the pharmacokinetics of the conjugate drastically. We therefore tested antitumor activity of PSMA-1-VcMMAE-Cy5.5 and also included equimolar doses of free MMAE and PSMA-ADC as controls in the study. Free MMAE was relatively ineffective at inhibiting tumor growth, even at the dose of 160 nmol/kg, all mice died within 36 days. In contrast, PSMA-1-VcMMAE-Cy5.5 effectively inhibited tumor growth, and expanded animal survival times. Significantly at 160 nmol/kg of PSMA-1-VcMMAE-Cy5.5 the tumors were completely eliminated in every case for a period of time and resulted in a cure rate (no tumors at end of study) of 60% for the 90-day experimental period. Changes in body weight were similar in each regimen and control group in the first 16 days, however, increased body weight was observed in PSMA-1-VcMMAE-Cy5.5 treated groups due to reduced disease burden. Compared to PSMA-1-VcMMAE-Cy5.5, all animals treated with 160 nmol/kg of PSMA-ADC survived the 90-day experimental time with 40% cure, the difference between the two groups was not significant (P=1.000).

We then tried PSMA-1-VcMMAE-Cy5.5 in orthotopic PC3pip tumor. No significant body weight loss was observed in mice treated with PSMA-1-VcMMAE-Cy5.5 while the PBS control mice lost body weight due to increased tumor burden. Tumor volume in PSMA-1-VcMMAE-Cy5.5 treated animals was significantly reduced and animal survival were dramatically extended (P=0.0026) with 40% of cure at day 90.

The mortality of prostate cancer is mainly due to metastasis and metastatic castration resistant prostate cancer is the most deadly and difficult form of the disease to treat. To test the effectiveness of PSMA-1-MMAE-Cy5.5 against metastatic disease, we developed a metastatic prostate cancer model using intracardiac injection of GFP-expressing PC3pip cells. We then used this model to assess the effectiveness of our drug conjugate. Treatment was initiated 1 week after cardiac injection of tumors cells, and mice received 160 nmol/kg of PSMA-1-VcMMAE-Cy5.5 every 4 days with a total of 5 doses. After treatment, no significant body weight loss was observed. The control mice died with 28 days. Maestro images of control mice showed GFP signal in tibia, spine, liver, spleen, kidney and testis, indicating tumors had metastasized to these sites. In contrast, all 5 treated mice survived the 90-day experimental period, and no GFP signal was observed in throughout the mice body, indicating a 100% response. PSMA-1-VcMMAE was also found to have the ability to prolong animal survival time with no body weight loss in the metastatic PC3pip model.

To show versatility of the antitumor activity of PSMA-1-VcMMAE-Cy5.5, we tested it in mice bearing heterotopic C4-2 tumors, which are androgen-independent prostate cancer cells endogenously expressing PSMA. PSMA-1-VcMMAE-Cy5.5 showed the ability to successfully inhibit C4-2 tumor growth with no weight loss and prolonged animal survival significantly (P=0.0018) with a 40% cure rate.

The targeted delivery of potent cytotoxic agents has emerged as a promising strategy for the treatment of cancer. In this study, we demonstrate that targeted delivery of MMAE can be more efficacious and less toxic than MMAE. More remarkably, PSMA-1-MMAE has an improved therapeutic index compared to PSMA-ADC.

Prodrug Strategy is Vital for Antitumor Activity

Targeted strategies require three components: the targeting ligand which can be an antibody, small molecular ligand or apatamer; the cytotoxic payload; and the linker. PSMA is a well-established biomarker for prostate cancer. We used our PSMA-1 ligand to target and deliver the potent microtubule polymerization inhibitor, MMAE, to PSMA-expressing prostate cancer cells. For linker selection, there are two types of linker—cleavable and non-cleavable linkers. To determine which linker would be most suitable, we tried both the cathepsin cleavable maleimido-caproyl-Val-Cit-PABC linker (Vc) (PSMA-1-VcMMAE-Cy5.5) (FIG. 11A) and the noncleavable maleimido-caproyl linker (Mc) (PSMA-1-McMMAE-Cy5.5) (FIG. 11B). It was found that although both conjugates selectively accumulated in PC3pip cells in vitro (FIG. 12) and in vivo (FIG. 13), effective antitumor activity was only observed with conjugates using the self-immolative cleavable "Vc"-linker, which concurs with the report that MMAE is most effective in its natural form and therefore not suitable for derivatization with non-cleavable linkers. Once entering the cells, the conjugates located mainly in the lysosomes (FIG. 12A), where cathepins are highly expressed and active. Inclusion of protease inhibitors diminished drug efficacy indicating that lysosomal accumulation and protease activation of PSMA-1-VcMMAE-Cy5.5 liberated free MMAE resulting in disruption of α-tubulin and cancer cell death (FIG. 11E).

Targeting Improves the Therapeutic Profile of MMAE

MMAE is a favored drug payload for ADCs, with many in clinical trials, and is usually conjugated to the antibody through a cathepsin B cleavable Vc linker, exploiting the ability to release drug intracellularly. Here, we replaced the antibody with a PSMA targeting ligand (PSMA-1) and developed a small-molecule-drug conjugate to reduce the cost and shorten the circulation time, potentially reducing the off-target toxicities resulting from longer blood half-lives. In vitro comparison of the cytotoxicity of free MMAE (FIG. 11E) with PSMA-ADC and our PSMA-1-drug conjugates (FIG. 14) showed that free MMAE killed both PC3pip and PC3flu cells with no selectivity. In contrast, PSMA-ADC and PSMA-1-drug conjugates selectively killed PC3pip cells with PSMA-ADC being the most potent and selective. The improved potency and selectivity of PSMA-ADC maybe due to its significantly higher affinity for PSMA (picomolar) than the PSMA-1 ligand used (nanomolar). PSMA-1-VcMMAE-Cy5.5 was found to be more potent than PSMA-1-VcMMAE in vitro, but less selective. The Cy5.5 renders greater hydrophobicity to PSMA-1-VcMMAE-Cy5.5. It has been reported that higher hydrophobicity can lead to increased cellular uptake and therefore higher cytotoxicity, which may explain the higher cytotoxicity of PSMA-1-VcMMAE-Cy5.5. Further increased hydrophobicity may have increased non-selective drug uptake into PC3flu cells, contributing to the decreased selectivity of PSMA-1-VcMMAE-Cy5.5.

Comparing the maximum tolerated dose (MTD) of MMAE, PSMA-ADC and PSMA-1-drug conjugates, PSMA-1-VcMMAE was more than 10-fold better than MMAE. This is likely due to targeted drug delivery. Interestingly, the MTD for PSMA-ADC was much lower than our lower affinity small molecule conjugate PSMA-1-VcMMAE, but very similar to PSMA-1-VcMMAE-Cy5.5. Although the MTDs of PSMA-ADC and PSMA-1-VcMMAE-Cy5.5 were lower than MMAE itself, their in vivo effective doses were disproportionately better. At the dose of 160 nmol/kg, PSMA-1-VcMMAE-Cy5.5 and PSMA-ADC potently inhibited PC3pip tumor growth leading to significant prolonged survival time, while MMAE did not show any effectiveness at the same dose. No significant difference in animal survival time was observed between PSMA-1-VcMMAE-Cy5.5 and PSMA-ADC treatment groups (P=1.000), suggesting that PSMA-1-VcMMAE-Cy5.5 has similar efficacy to PSMA-ADC. Compared to PSMA-ADC and PSMA-1-VcMMAE-Cy5.5, PSMA-1-VcMMAE needed a higher dose to achieve the same treatment effect when given at the same dosing schedule, which is likely attributed to differences in pharmacokinetic characteristics. Our previous studies have shown that the hydrophobicity/hydrophilicity of conjugated dyes can dramatically impact the pharmacokinetics of the conjugates, with more hydrophilic conjugates resulting in a shorter time-to-peak accumulation in tumors and shorter circulation times. It may be that integration of hydrophobic Cy5.5 in PSMA-1-VcMMAE-Cy5.5 provided elongated circulation of the drug conjugate in vivo, maximizing antitumor activity. The difference in pharmacokinetics may contribute to the different MTDs of PSMA-1-VcMMAE, PSMA-1-VcMMAE-Cy5.5 and PSMA-ADC. Future pharmacokinetic studies are required to confirm our hypothesis and optimize these agents. It was noticed that animals treated by the drug conjugates showed no body weight loss due to the treatment, indicating low toxicity of the drug conjugates. Biodistribution studies using PSMA-1-VcMMAE-Cy5.5 showed that the fluorescence from the conjugate was associated with PC3pip tumors with minimal signals observed in the liver, spleen, lungs etc. This may indirectly indicate the low toxicity of the conjugate in other organs. However, MMAE will be detached from Cy5.5 in vivo, the information obtained from fluorescence imaging may not be directly correlated to the biodistribution of the drug. Detailed biodistribution and toxicity studies are still needed.

Notably, PSMA-1-VcMMAE and PSMA-1-VcMMAE-Cy5.5 showed the ability to significantly prolong the survival time of animals in metastatic PC3pip tumor model. In spite of the fact that the treatment initiated one week after tumor inoculation, before the metastasis was detectable using imaging, it is encouraging that it exhibited the ability to successfully prevent tumor metastasis. As a significant percentage of patients with prostate cancer die from the metastatic form of the disease due to lack of effective treatment options, it is critical to develop potent treatments that can effectively eradicate cancer cells and control metastatic tumors. We also found that both PSMA-1-VcMMAE and PSMA-1-VcMMAE-Cy5.5 greatly inhibited tumor growth when given every 7 days.

PSMA-1-VcMMAE utilizes the same targeting strategy as PSMA-ADC, but has shorter circulation time due to its smaller size and can be easily excreted from the body leading to reduced toxicity. PSMA-1-VcMMAE effectively inhibited tumor growth starting at the dose of 191 nmol/kg, and its' MTD was at 7640 nmol/kg, resulting in a therapeutic index of 40. The TI of PSMA-1-VcMMAE-Cy5.5 is 480/80=6. PSMA-ADC was reported to be effective starting at 2.0-3.0 mg/kg (53 nmol/kg-80 nmol/kg), its MTD was at 640 nmol/kg resulting in its TI at 8-12. By replacing the antibody with our PSMA-1 ligand, PSMA-1-VcMMAE dramatically improved the therapeutic index. These characteristics will help it avoid the problems of PSMA-ADC found in clinical trials. A theranostic such as PSMA-1-VcMMAE-Cy5.5 will allow modification of pharmacokinetics and will play a key role in initial drug development by enabling visualization of drug-target engagement, tumor size, and providing feedback information on the therapy status. Even though after prodrug activation by proteases Cy5.5 is released and physically separated from MMAE, this theranostic molecule provides significant data about drug targeting and allows greater ease and less time for small animal optimization studies. It is the first example of combining targeted small molecules with therapeutics and fluorophores for a theranostic approach to develop targeted drugs for prostate cancer.

In summary, we have developed small-molecule-based prodrugs for the treatment of prostate cancer. Their antitumor activities were demonstrated not only in androgen independent PC3pip heterotopic, orthotopic and metastatic models but also in androgen independent C4-2 tumor models that endogenously express PSMA, with no toxicity observed.

All references cited herein, including patents, patent applications, papers, text books, and the like, and the references cited therein, to the extent that they are not already, are hereby incorporated herein by reference in their entirety. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

Having described the invention, we claim:
1. A method of treating a prostate specific membrane antigen (PSMA) expressing cancer comprising:
administering to a subject with PSMA expressing cancer a therapeutically effective amount of a pharmaceutical composition, the pharmaceutical composition comprising a PSMA targeted conjugate compound that includes general formula (I):

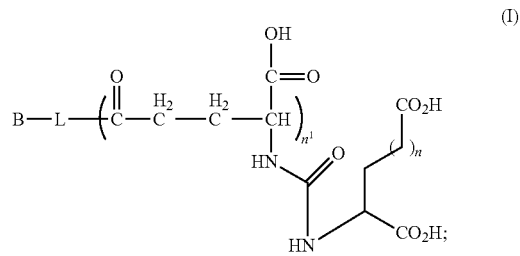

wherein n and $n^1$ are each independently 1, 2, 3, or 4;
L is an optionally substituted aliphatic or heteroaliphatic linking group;

B has the following formula:

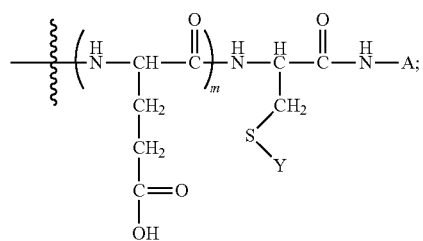

wherein m is 1, 2, 3, or 4, A is H or

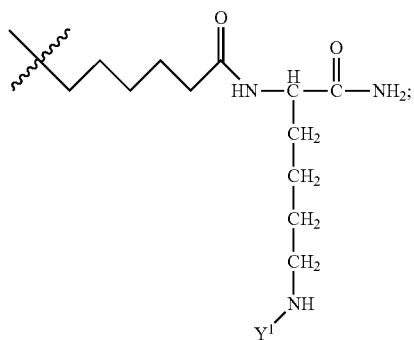

and Y and Y$^1$ are each independently selected from at least one of a therapeutic agent or a theranostic agent that is directly or indirectly linked to, respectively, the thiol group of B and the amine group of A.

2. The method of claim 1, wherein L includes at least one ring selected from the group consisting of an optionally substituted 4 to 7 membered nonaromatic heterocyclic ring and an optionally substituted C4-C7 cycloalkyl ring.

3. The method of claim 1, wherein B has the following formula:

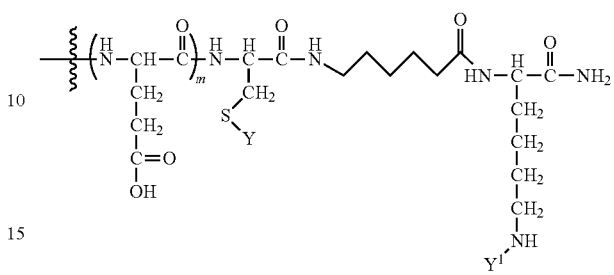

wherein m is 1, 2, 3, or 4; and Y and Y$^1$ are each independently selected from at least one of a therapeutic agent or a theranostic agent that is directly or indirectly linked to, respectively, the thiol group and the amine group.

4. The method of claim 3, wherein Y is a therapeutic agent and Y$^1$ is a detectable moiety.

5. The method of claim 1, wherein Y is therapeutic agent linked to B via a protease cleavable or acid-labile linker.

6. The method of claim 5, wherein the linker is selected from a MC-Val-Cit-PABC protease cleavable linker and a 4-(4-maleimidomethyl)cyclohexane-1-carboxyl hydrazide (MMCCH) acid-labile linker.

7. The method of claim 1, wherein the therapeutic agent is selected from doxorubicin and monomethyl auristatin E (MMAE).

8. The method of claim 1, comprising the general formula:

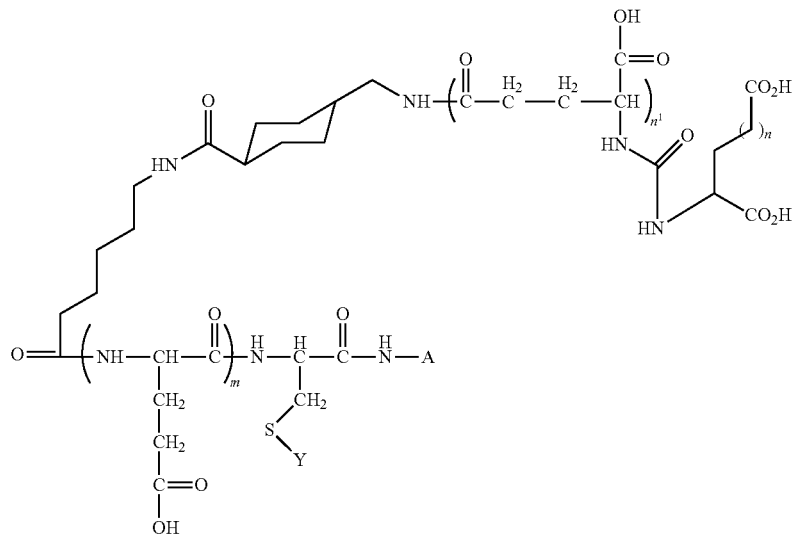

wherein m, n and n¹ are each independently 1, 2, 3, or 4;
A is H or

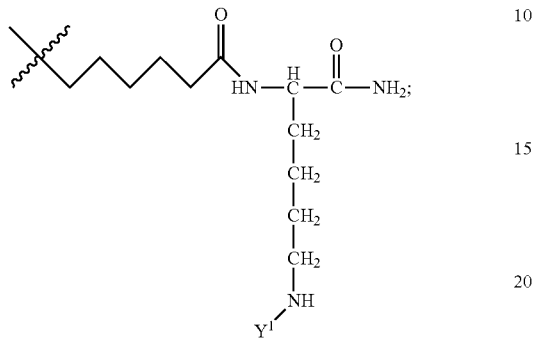

and Y and Y¹ are each independently selected from at least one of a therapeutic agent or a theranostic agent that is directly or indirectly linked to, respectively, the thiol group and the amine group.

9. The method of claim 1, the PSMA targeted conjugate compound having a formula selected from the group consisting of:

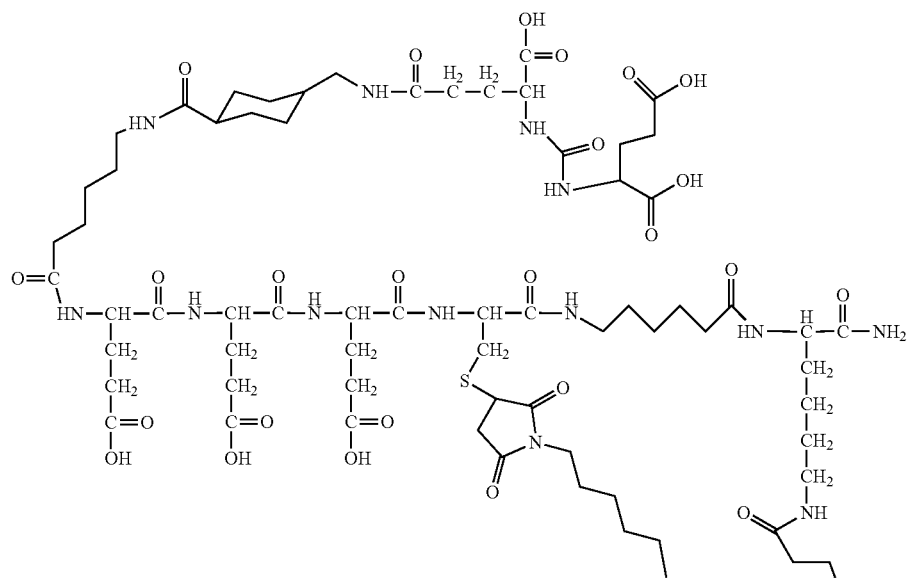

55
56
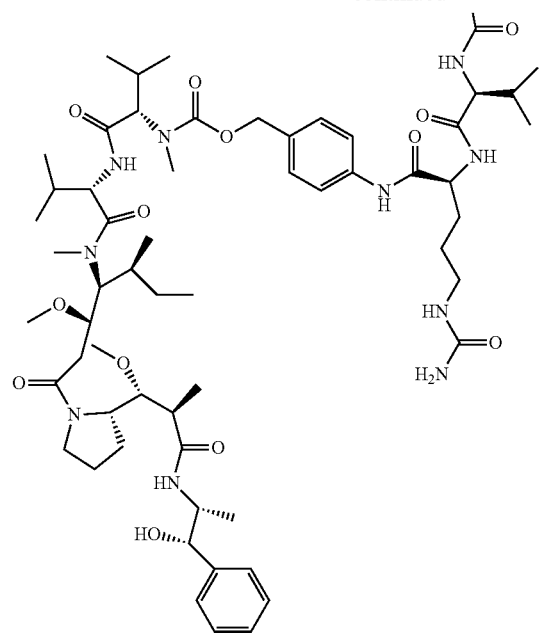
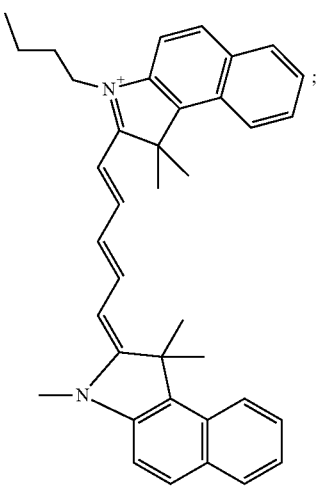
-continued
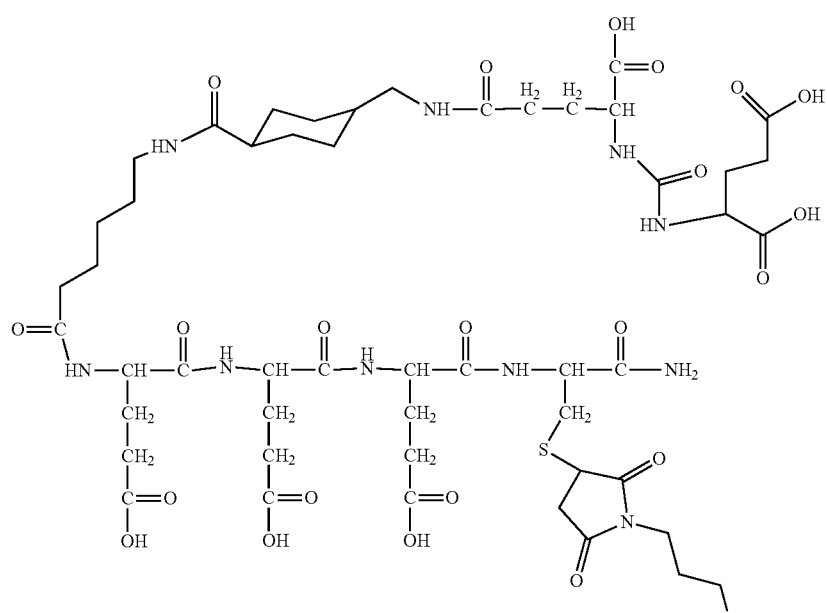

-continued
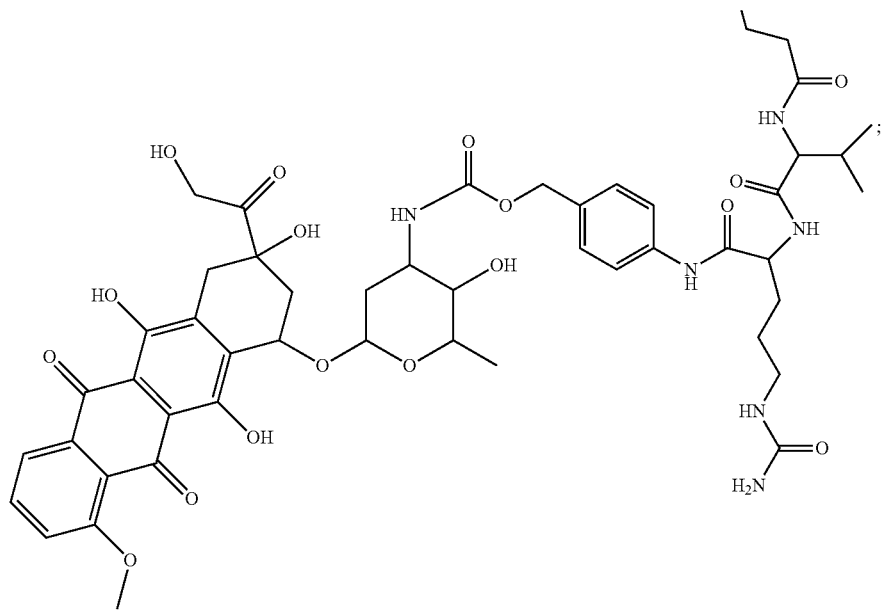
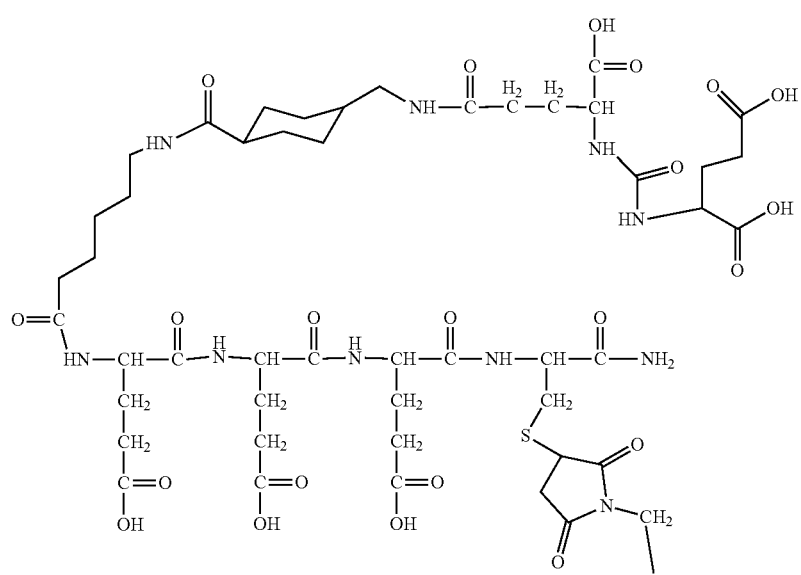

-continued

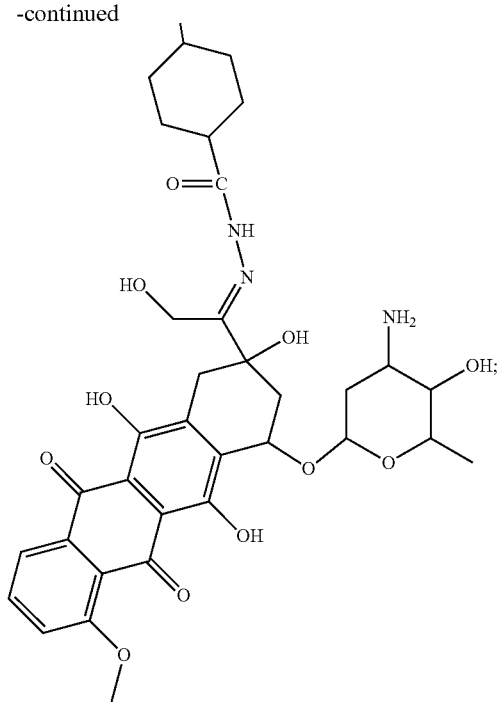

and pharmaceutical salts thereof.

10. The method of claim 1, wherein the pharmaceutical composition is administered by intravenous injection.

11. The method of claim 1, the pharmaceutical composition further comprising a pharmaceutically acceptable carrier.

12. The method of claim 1, wherein the PSMA expressing cancer is selected from the group consisting of renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma.

13. The method of claim 1, wherein the PSMA expressing cancer is metastatic prostate cancer.

14. A method of treating a prostate specific membrane antigen (PSMA) expressing prostate cancer comprising:
administering to a subject with PSMA expressing prostate cancer a therapeutically effective amount of a pharmaceutical composition, the pharmaceutical composition comprising a PSMA targeted conjugate compound that includes general formula (I):

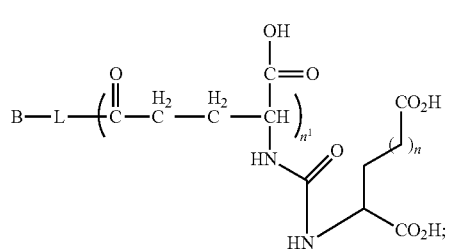

(I)

wherein n and $n^1$ are each independently 1, 2, 3, or 4;

L is an optionally substituted aliphatic or heteroaliphatic linking group;

B has the following formula:

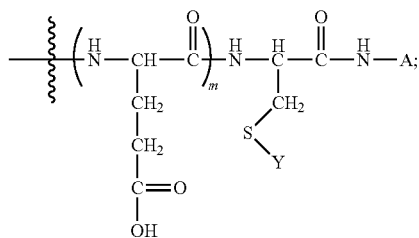

wherein m is 1, 2, 3, or 4, A is H or

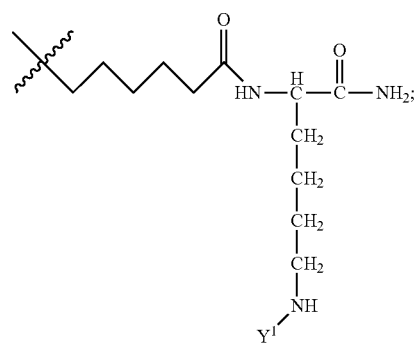

and Y and $Y^1$ are each independently selected from at least one of a therapeutic agent or a theranostic agent that is directly or indirectly linked to, respectively, the thiol group of B and the amine group of A.

15. The method of claim 14, wherein L includes at least one ring selected from the group consisting of an optionally substituted 4 to 7 membered nonaromatic heterocyclic ring and an optionally substituted C4-C7 cycloalkyl ring.

16. The method of claim 14, wherein B has the following formula:

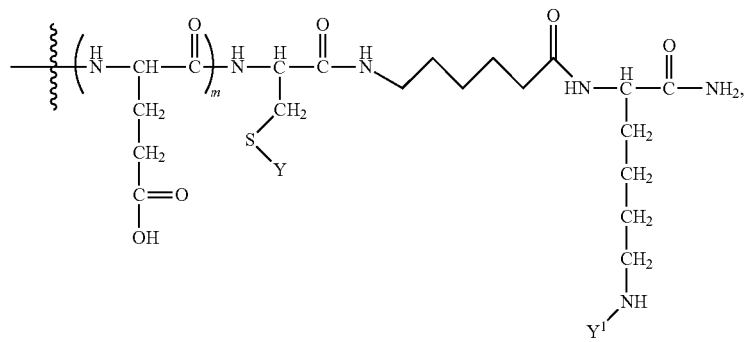

wherein m is 1, 2, 3, or 4; and Y and $Y^1$ are each independently selected from at least one of a therapeutic agent or a theranostic agent that is directly or indirectly linked to, respectively, the thiol group and the amine group.

17. The method of claim 16, wherein Y is a therapeutic agent and $Y^1$ is a detectable moiety.

18. The method of claim 14, wherein Y is therapeutic agent linked to B via a protease cleavable or acid-labile linker.

19. The method of claim 18, wherein the linker is selected from a MC-Val-Cit-PABC protease cleavable linker and a 4-(4-maleimidomethyl)cyclohexane-1-carboxyl hydrazide (MMCCH) acid-labile linker.

20. The method of claim 14, wherein the therapeutic agent is selected from doxorubicin and monomethyl auristatin E (MMAE).

21. The method of claim 14, comprising the general formula:

wherein m, n and $n^1$ are each independently 1, 2, 3, or 4; A is H or

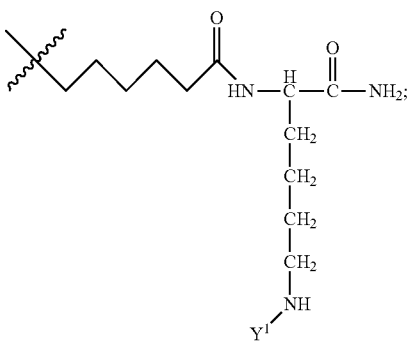

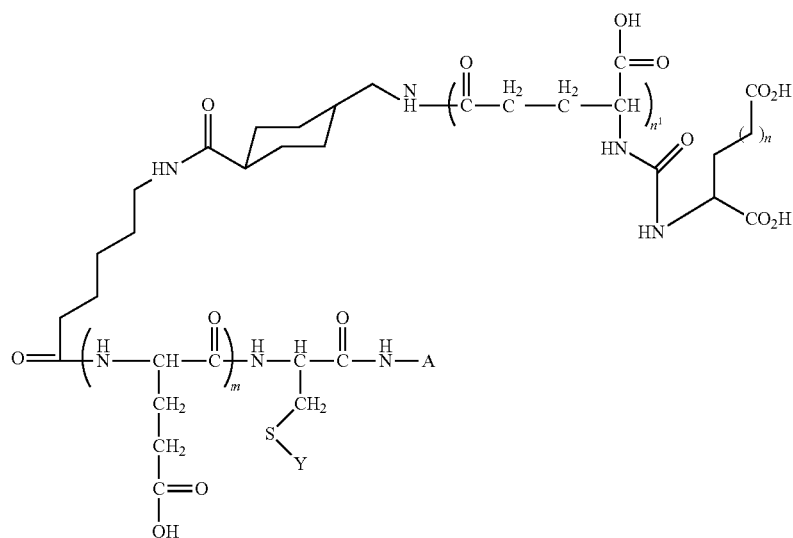

and Y and Y¹ are each independently selected from at least one of a therapeutic agent or a theranostic agent that is directly or indirectly linked to, respectively, the thiol group and the amine group.
22. The method of claim 14, the PSMA targeted conjugate compound having a formula selected from the group consisting of:
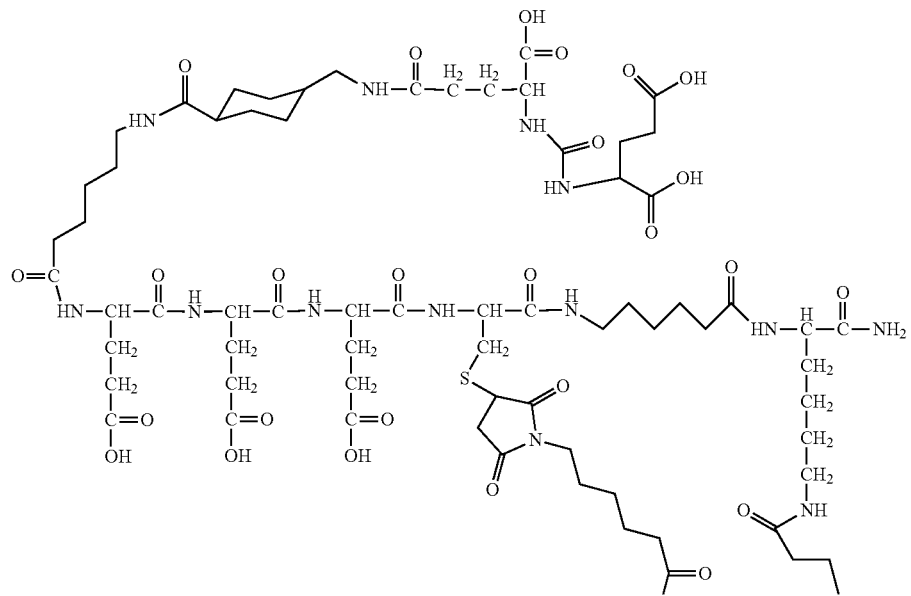
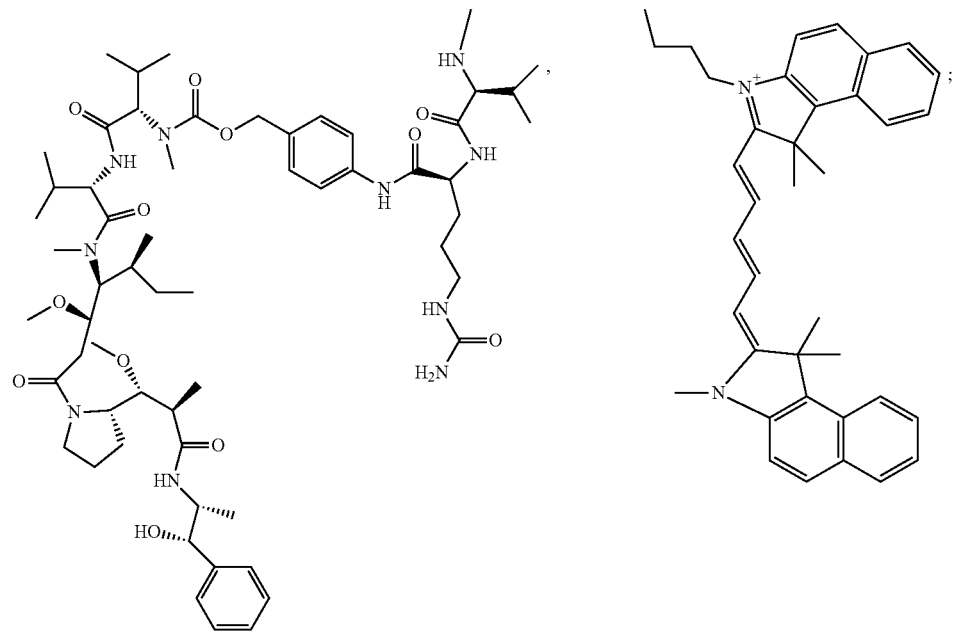

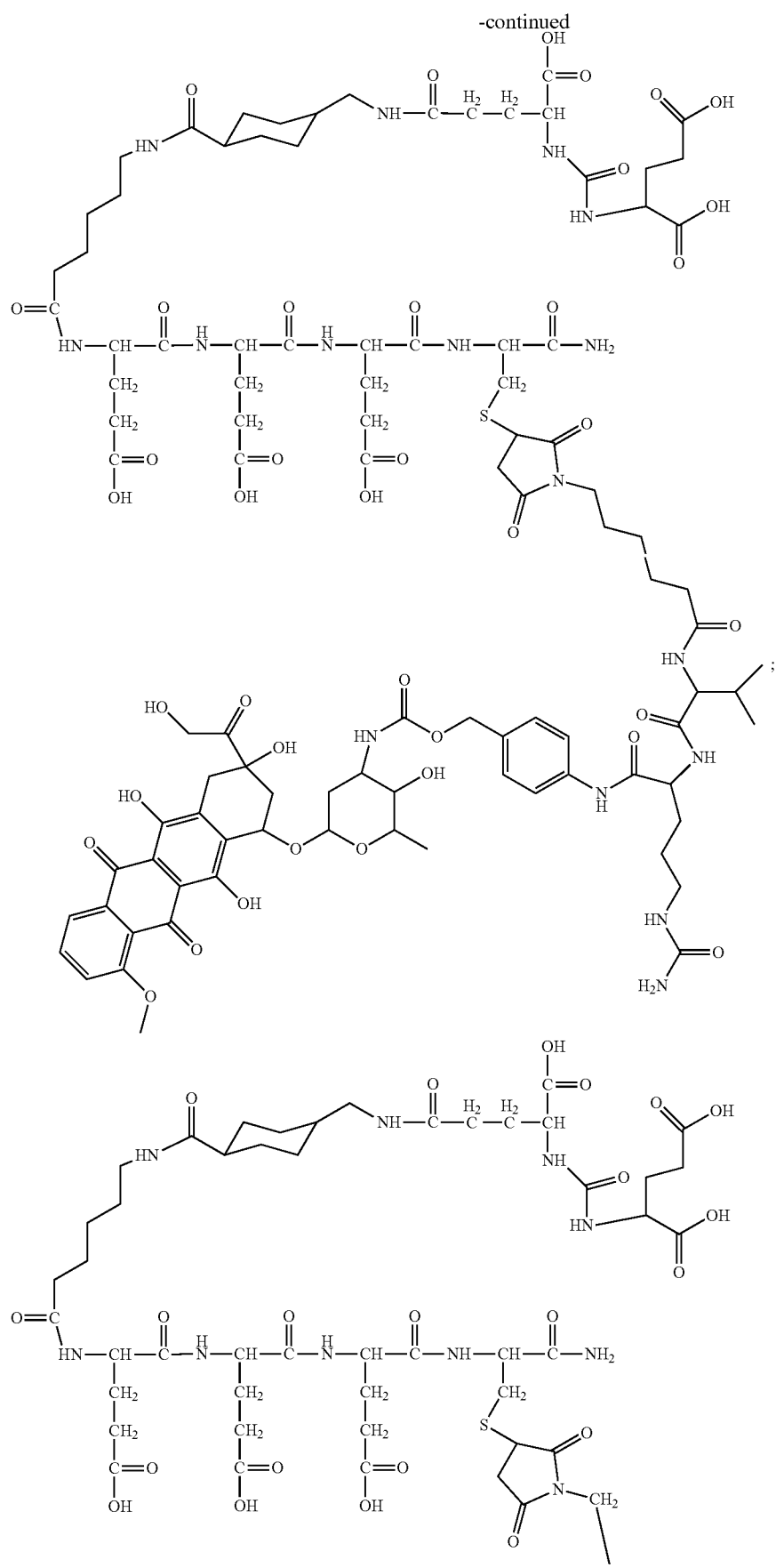

-continued
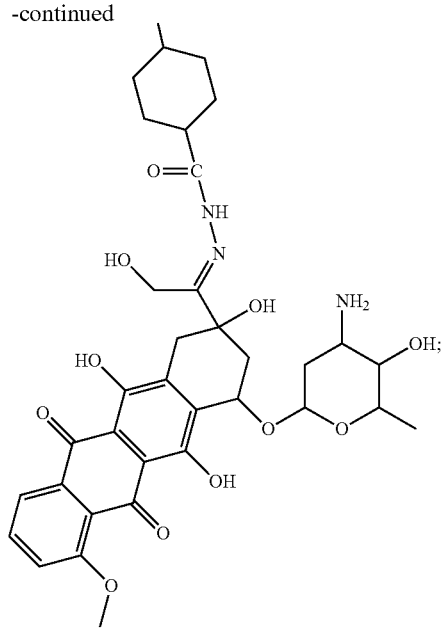
and pharmaceutical salts thereof.
23. The method of claim 14, wherein the pharmaceutical composition is administered by intravenous injection.
24. The method of claim 14, the pharmaceutical composition further comprising a pharmaceutically acceptable carrier.
25. The method of claim 14, wherein the PSMA expressing cancer is metastatic prostate cancer.
* * * * *